US012768832B2

(12) United States Patent
Zhang et al.

(10) Patent No.: US 12,768,832 B2
(45) Date of Patent: Oct. 20, 2026

(54) CHEMICAL COCKTAIL FOR INDUCING SENESCENCE IN HUMAN NEURONS TO PROMOTE DISEASE MODELING AND DRUG DISCOVERY

(71) Applicant: Wisconsin Alumni Research Foundation, Madison, WI (US)

(72) Inventors: Su-Chun Zhang, Waunakee, WI (US); Ali Fathi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1226 days.

(21) Appl. No.: 17/117,096

(22) Filed: Dec. 9, 2020

(65) Prior Publication Data

US 2021/0311023 A1 Oct. 7, 2021

Related U.S. Application Data

(60) Provisional application No. 62/945,386, filed on Dec. 9, 2019.

(51) Int. Cl.
*G01N 33/50* (2006.01)
*C12N 5/079* (2010.01)

(52) U.S. Cl.
CPC ....... *G01N 33/5058* (2013.01); *C12N 5/0618* (2013.01); *C12N 2501/065* (2013.01); *C12N 2501/724* (2013.01); *C12N 2501/727* (2013.01); *C12N 2501/734* (2013.01); *C12N 2503/02* (2013.01)

(58) Field of Classification Search
None
See application file for complete search history.

(56) References Cited

U.S. PATENT DOCUMENTS

2017/0038365 A1 2/2017 Lloyd et al.

FOREIGN PATENT DOCUMENTS

WO WO2010118419 A2 10/2010
WO WO2013178821 A1 12/2013
WO WO2014172507 A1 10/2014

OTHER PUBLICATIONS

Martinez- Cue et al.(Front Cell Neurosc 14: 1-22, 2020) (Year: 2020).*
Akay et al, (J. Neurovirol 20: 39-53, 2014) (Year: 2014).*
Vivithanaporn et al (AIDS 30: 543-552, 2016) (Year: 2016).*
Liu et al (J Cereb Blood Flow Metab 31: 680-692, 2011) (Year: 2011).*
Friedhelm et al, (Neural Regeneration Res 16: 1212-1213, 2021) (Year: 2021).*
Ha et al (Exp Opin Ther Pat 26: 1273-1289, 2016) (Year: 2016).*
Miller et al (Cell Stem Cell 13: 691-705, 2013) (Year: 2013).*
Arii et al (Sc Rep 10: 1-13, 2020) (Year: 2020).*
Odeleye et al (J Neurovirol 15: Supp 1: p. 68, Abstract P140, 2009) (Year: 2009).*
Chen et al, (Biomaterials 34: 10172-10181, 2013) (Year: 2013).*
Ossama et al (Cell Mol Life Sc 76: 1169-1183, Mar. 2019).*
Vivithanaporn et al (AIDS 30: 543-552, 2016).*
Gannon et al (J Neuroimmune Pharm 8: 417, 2013)—Conference abstract.*
Du et al (Autophagy 5: 663-675, 2009).*
Chen et al (Neurosci Lett 4828 264-8, 2010).*
Nakagawa et al (Oncol Lett 15: 1495-1502, 2018).*
Fabrizi et al (J Neural Transm 119: 1295-1305, 2012).*
Miller et al (Cell Stem Cell 13: 691-705, 2013).*
International Search Report and Written Opinion for PCT/US20/064138, mailed Apr. 14, 2021.
Anders et al. "Differential expression analysis for sequence count data." Genome Biology 11:R106 (Apr. 2010).
Bedford et al. "Depletion of 26S proteasomes in mouse brain neurons causes neurodegeneration and Lewy-like inclusions resembling human pale bodies." J Neurosci. 28(33):8189-98 (Aug. 2008).
Bilican et al. "Mutant induced pluripotent stem cell lines recapitulate aspects of TDP-43 proteinopathies and reveal cell-specific vulnerability." PNAS 109(15):5803-8 (Mar. 2012).
Boger et al. "Effects of brain-derived neurotrophic factor on dopaminergic function and motor behavior during aging." Genes Brain Behav. 10(2):186-98 (Oct. 2010).
Bonda et al. "The sirtuin pathway in ageing and Alzheimer disease: mechanistic and therapeutic considerations." Lancet Neurol. 10(3):275-9 (Mar. 2011).
Campos et al. "Accelerating neuronal aging in in vitro model brain disorders: a focus on reactive oxygen species." Front Aging Neurosci. 6:292 (Oct. 2014).
Chen et al. "Effects of aging on circadian patterns of gene expression in the human prefrontal cortex." Proc Natl Acad Sci USA 113(1):206-11 (Dec. 2015).
Chen et al. "Modeling ALS with iPSCs reveals that mutant SOD1 misregulates neurofilament balance in motor neurons." Cell Stem Cell 14(6):796-809 (Jun. 2014).
Chen et al. "Engineering Human Stem Cell Lines with Inducible Gene Knockout using CRISPR/Cas9." Cell Stem Cell 17(2):233-44 (Aug. 2015).
Dantuma et al. "The ubiquitin-proteasome system in neurodegenerative diseases: precipitating factor, yet part of the solution." Front Mol Neurosci. 7:70 (Jul. 2014).

(Continued)

*Primary Examiner* — Kimberly Ballard
*Assistant Examiner* — Aditi Dutt
(74) *Attorney, Agent, or Firm* — McDonnell Boehnen Hulbert & Berghoff LLP

(57) ABSTRACT

Provided herein are methods and compositions for inducing chemical senescence in neurons and methods of using chemically induced senescent neurons for modeling neurodegenerative disease and drug discovery. The methods include contacting human neurons with a culture medium comprising an inhibitor of DNA glycosylase 1, an autophagy inhibitor, and an HIV protease inhibitor to obtain an in vitro population of senescent neurons within about 4 days. When the neurons are obtained from a patient having a neurodegenerative disease, chemically induced senescent neurons obtained by these methods recapitulate cellular and subcellular phenotypes observed in individuals with the neurodegenerative disease.

8 Claims, 27 Drawing Sheets

Specification includes a Sequence Listing.

(56) References Cited

OTHER PUBLICATIONS

Dower et al. "Targeted Inhibition of ULK1 promotes apoptosis and Suppresses Tumor Growth and Metastasis in Neuroblastoma." Molecular Cancer Therapeutics 17(11): 2365-2376, (Aug. 2018).
Dreesen et al. "Accelerated aging syndromes, are they relevant to normal human aging?" Aging (Albany, NY) 3(9):889-95 (Sep. 2011).
Du et al. "Generation and expansion of highly pure motor neuron progenitors from human pluripotent stem cells." Nat Commun. 6:6626 (Mar. 2015).
Flex et al. "Aberrant Function of the C-Terminal Tail of HIST1H1E Accelerates Cellular Senescence and Causes Premature Aging." Am J Hum Genet. 105(3):493-508, (Sep. 2019).
Fujimori et al. "Modeling sporadic ALS in iPSC-derived motor neurons identifies a potential therapeutic agent." Nat Med. 24 (10):1579-89, (Aug. 2018).
Gevry et al. "p21 transcription is regulated by differential localization of histone H2A.Z." Genes Dev. 21(15):1869-81, (Aug. 2007).
He et al. "Autophagy in ageing and ageing-associated diseases." Acta Pharmacol Sin. 34(5):605-11, (May 2013).
Hernandez-Segura et al. "Hallmarks of Cellular Senescence." Trends Cell Biol. 28(6):436-53 (Jun. 2018).
Ihara et al. "The Ubiquitin-Proteasome System and the Autophagic-Lysosomal System in Alzheimer Disease." Cold Spring Harb Perspect Med. 2(8): a006361, (Aug. 2012).
Jacobs et al. "Inhibition of DNA Glycosylases via Small Molecule Purine Analogs." PLoS One. 8(12): e81667 (Dec. 2013).
Kim et al. "Mitochondrial Aging Defects Emerge in Directly Reprogrammed Human Neurons due to Their Metabolic Profile." Cell Rep. 23(9):2250-8 (May 2018).
Klim et al. "ALS-implicated protein TDP-43 sustains levels of STMN2, a mediator of motor neuron growth and repair." Nat Neurosci. 22(2):167-79 (Feb. 2019).
Konar et al. "Age-associated Cognitive Decline: Insights into Molecular Switches and Recovery Avenues." Aging Dis. 7(2):121-9, (Mar. 2016).
Kouroupi et al. "Defective synaptic connectivity and axonal neuropathology in a human iPSC-based model of familial Parkinson's disease." PNAS 114(18):E3679-E3688 (2017).
Kumar et al. "Age-related expression of Neurexin1 and Neuroligin3 is correlated with presynaptic density in the cerebral cortex and hippocampus of male mice." Age (Dordr). 37(2):17 (Apr. 2015).
Kyng et al. "Gene expression profiling in Werner syndrome closely resembles that of normal aging." PNAS 100(21):122259-64 (Oct. 2003).
Ladewig et al. "Small molecules enable highly efficient neuronal conversion of human fibroblasts." Nat Methods. 9(6):575-8 (Apr. 2012).
Leandro et al. "The Impact of Base Excision DNA Repair in Age-Related Neurodegenerative Diseases." Mutat Res. 776:31-9 (Jun. 2015).
Lo Sardo et al. "Influence of donor age on induced pluripotent stem cells." Nat Biotechnol. 35(1):69-74 (Dec. 2016).
Lopez-Otin et al. "The Hallmarks of Aging." Cell. 153(6):1194-217 (Nov. 2013).
Lozano-Torres et al. "The chemistry of senescence." Nature Reviews Chemsitry 3(7):426-441, (Jun. 2019).
Ma et al. "SQSTM1/p62: A Potential Target for Neurodegenerative Disease." ACS Chem Neurosci. 10(5):2094-114 (Jan. 2019).
Madabhushi et al. "DNA damage and its links to neurodegeneration." Neuron. 83(2):266-82, (Jul. 2014).
Maynard et al. "DNA Damage, DNA Repair, Aging, and Neurodegeneration." Cold Spring Harb Perspect Med. 5(10) (2015).
Mazucanti et al. "Longevity Pathways (mTOR, SIRT, Insulin/IGF-1) as Key Modulatory Targets on Aging and Neurodegeneration." Curr Top Med Chem. 15(21):2116-38 (2015).
Mertens et al. "Directly Reprogrammed Human Neurons Retain Aging-Associated Transcriptomic Signatures and Reveal Age-Related Nucleocytoplasmic Defects." Cell Stem Cell 17(6):705-18 (Oct. 2015).
Miller et al. "Human iPSC-Based Modeling of Late-Onset Disease via Progerin-Induced Aging." Cell Stem Cell 13(6):691-705, (Dec. 2013).
Mishima et al. "Modeling Parkinson's Disease and Atypical Parkinsonian Syndromes Using Induced Pluripotent Stem Cells." Int J Mol Sci. 19(12):3870, (Dec. 2018).
Monzio Compagnoni et al. "Mitochondrial Dysregulation and Impaired Autophagy in iPSC-Derived Dopaminergic Neurons of Multiple System Atrophy." Stem Cell Reports 11(5):1185-98 (Oct. 2018).
Ossama et al. "Cellular senescence is associated with reorganization of the microtubule cytoskeleton." Cellular and Molecular Life Sciences 76(6): 1169-1183, (Mar. 2019).
Pan et al. "The role of autophagy-lysosome pathway in neurodegeneration associated with Parkinson's disease." Brain 131(8):1969-78 (Jan. 2008).
Paramanik et al. "Role of CREB signaling in aging brain." Arch Ital Biol. 151(1):33-42, (Mar. 2013).
Qi et al. "Combined small-molecule inhibition accelerates the derivation of functional, early-born, cortical neurons from human pluripotent stem cells." Nat Biotechnol. 35(2):154-63, (Feb. 2017).
Reinhardt et al. "Genetic correction of a LRRK2 mutation in human iPSCs links parkinsonian neurodegeneration to ERK-dependent changes in gene expression." Cell Stem Cell 12(3):354-67, (Mar. 2013).
Robinson et al. "edgeR: a Bioconductor package for differential expression analysis of digital gene expression data." Bioinformatics. 26(1):139-40 (Nov. 2009).
Rubinsztein et al. "Autophagy and aging." Cell 146(5):682-95, (Sep. 2011).
Satoh et al. "The brain, sirtuins, and ageing." Nat Rev Neurosci. 18(6):362-74, (May 2017).
Sanchez-Danes et al. "Disease-specific phenotypes in dopamine neurons from human iPS-based models of genetic and sporadic Parkinson's disease." EMBO Mol Med. 4(5):380-95 (May 2012).
Sanjana et al. "Improved vectors and genome-wide libraries for CRISPR screening." Nat Methods 11(8):783-4 (Aug. 2014).
Scotter et al. "Differential roles of the ubiquitin proteasome system and autophagy in the clearance of soluble and aggregated TDP-43 species." J Cell Sci. 127(6):1263-78, (Jan. 2014).
Shalem et al. "Genome-scale CRISPR-Cas9 knockout screening in human cells." Science. 343(6166):84-87, (Dec. 2013).
Silhol et al. "Age-related changes in brain-derived neurotrophic factor and tyrosine kinase receptor isoforms in the hippocampus and hypothalamus in male rats." Neuroscience. 132(3):613-24 (2005).
Stewart et al. "Comparative RNA-seq Analysis in the Unsequenced Axolotl: The Oncogene Burst Highlights Early Gene Expression in the Blastema." PLoS Comput. Biol. 9(3):e1002936 (Mar. 2013).
Sykora et al. ""Base excision repair in the mammalian brain: Implication for age relatedneurodegeneration."" Mech Ageing Dev. 134(10): 440-8 (May 2013).
Petrova et all. "Small molecule compounds that inudce cellular senescence." Aging Cell 15(6): 999-1017, (Sep. 2016).
Thomson et al. "Embryonic stem cell lines derived from human blastocysts." Science 282: 1145-1147 (Nov. 1998).
Tong et al. "Effects of senescence on the expression of BDNF and TrkB receptor in the lateral geniculate nucleus of cats." Dongwuzue Yanjiu 36(1):48-53 (Jan. 2015).
Van Tijn et al. "Dose-dependent inhibition of proteasome activity by a mutant ubiquitin associated with neurodegenerative disease." J Cell Sci. 120(9):1615-23 (Apr. 2007).
Vijayaraghavan et al. "Inhibiting CDK in Cancer Therapy: Current Evidence andFuture Directions." Target Oncol. 13(1):21-38, (Feb. 2018).
Von Bohlen Und Halbach. ""Involvement of BDNF in age-dependent alterations in thehippocampus."" Front Aging Neurosci. 2:36 (Aug. 2010).
Wyss-Coray. "Ageing, neurodegeneration and brain rejuvenation." Nature 539(7628):180-6 (Nov. 2016).

(56) References Cited

OTHER PUBLICATIONS

Yang et al. "One-step generation of mice carrying reporter and conditional alleles by CRISPR/Cas-mediated genome engineering." Cell 154(6): 1370-79 (Aug. 2013).
Yu et al. "Induced pluripotent stem cell lines derived from human somatic cells." Science 318(5858): 1917-1920 (Nov. 2007).
Zhang et al. "The role of ubiquitin proteasomal system and autophagy-lysosome pathway in Alzheimer's disease." Rev Neurosci. 28(8):861-8 (Nov. 2017).
Zheng et al. "Failure of Ubiquitin Proteasome System: Risk for Neurodegenerative Diseases." Neurodegener Dis. 14(4):161-75 (Nov. 2014).

* cited by examiner

FIG. 5 (continued)

F

Overrepresented pathways in SLO

| Term | Overlap | P-value |
|---|---|---|
| Cytoplasmic Ribosomal Proteins WP477 | 49/89 | 2.40E-31 |
| Histone Modifications WP2369 | 22/67 | 2.67E-09 |
| BDNF signaling pathway WP2380 | 28/144 | 4.63E-06 |
| Translation Factors WP107 | 15/52 | 5.61E-06 |
| The effect of progerin on the involved genes in Hutchinson-Gilford Progeria Syndrome WP4320 | 12/37 | 1.29E-05 |

Underrepresented pathways in SLO

| Term | Overlap | P-value |
|---|---|---|
| Calcium Regulation WP536 | 35/149 | 2.62E-11 |
| NO/cGMP/PKG mediated Neuroprotection WP4008 | 16/47 | 2.39E-08 |
| GABA receptor Signaling WP4159 | 13/31 | 2.73E-08 |
| Pathways in Drug Addiction WP2636 | 15/42 | 3.12E-08 |
| Hippo Signaling WP4540 | 23/98 | 6.65E-08 |
| BDNF signaling pathway WP2380 | 27/144 | 6.78E-07 |

A

B

| STR Locus | STR Genotype Repeat # | STR Genotype |
|---|---|---|
| FGA | 16–18, 18.2, 19, 19.2, 20, 20.2, 21, 21.2, 22, 22.2, 23, 23.2, 24, 24.2, 25, 25.2, 26–30, 31.2, 43.2, 44.2, 45.2, 46.2 | 19, 21 |
| TPOX | 6-13 | 9, 11 |
| D8S1179 | 7-18 | 10, 12 |
| vWA | 10-22 | 17, 17 |
| Amelogenin | X, Y | X, Y |
| Penta D | 2.2, 3.2, 5, 7-17 | 11, 12 |
| CSF1PO | 6-15 | 10, 13 |
| D16S539 | 5, 8-15 | 9, 11 |
| D7S820 | 6-14 | 8, 12 |
| D13S317 | 7-15 | 11, 12 |
| D5S818 | 7-16 | 11, 14 |
| Penta E | 5-24 | 7, 16 |
| D18S51 | 8-10, 10.2, 11-13, 13.2, 14-27 | 12, 16 |
| D21S11 | 24, 24.2, 25, 25.2, 26-28, 28.2, 29, 29.2, 30, 30.2, 31, 31.2, 32, 32.2, 34, 34.2, 35, 35.2, 36-38 | 30, 31 |
| TH01 | 4-9, 9.3, 10-11, 13.3 | 6, 9.3 |
| D3S1358 | 12-20 | 15,15 |

C

*TDP43 G298S iPSC#13*

*Total Counted: 20*
*Total Analyzed: 8*
*Total Karyogrammed: 4*
*Band Resolution: 400 - 500*

*TDP43 G298G iPSC#18*

*Total Counted: 20*
*Total Analyzed: 8*
*Total Karyogrammed: 4*
*Band Resolution: 475 - 550*

FIG. 11

| Name | Function | Working Con. | Name | Function | Working Con. |
|---|---|---|---|---|---|
| **WZ4003** | AMPK inhibitor | 2uM | **SirReal2** | Sirt2 inhibitor | 1uM |
| **MHY1485** | mTOR activator | 2uM | **Rucaparib** | PARP1 inhibitor | 1uM |
| **Fumonisin B1** | AKT activators | 5uM | **Temozolomide** | DNA alkylation | 100 uM |
| **Sirtinol** | Sirtuin inhibitors | 5uM | **Lactacystin** | irreversible proteasome inhibitor | 100 nM |
| **SBI-0206965** | Autophagy inhibitor | 10uM | **KU-60019** | ATM inhibitor | 100nM |
| **Romidepsin** | HDAC1,2 inhibitor | 10pM | **5-AZA-20-DEOXYCYTIDINE** | DNA methyltransferase inhibitor | 1uM |
| **Etoposid** | Topo II inhibitor | 2uM | **Actinomycin D** | inhibiting DNA-primed RNA synthesis | 10 nM |
| **Lomeguatrib-O6BTG** | MGMT inhibitor | 10nM | **Cisplatin** | Topo I,II inhibitor | 10 uM |
| **O151** | DNA Glycosylase-1 inhibitor | 1uM | **SCR-7** | Ligase V inhibitor | 5 uM |
| **Palbociclib** | CDK4/6 inhibitor | 1uM | **Phosphoramidon** | metalloendopeptidase inhibitor | 1uM |
| **Apo866** | NAD biosynthesis inhibitor | 10nM | **Lopinavir** | HIV protease inhibitor | 1uM |
| **Hydroxyurea** | DNA synthesis stress inducer | 500uM | **GGTI298** | geranylgeranyltransferase I (GGTase I) inhibitor. | 1uM |
| **EX-527** | Sirt1 inhibitor | 100nM | **Sodium Butyrate** | histone deacetylase inhibitor I, II | 100 uM |

CHEMICAL COCKTAIL FOR INDUCING SENESCENCE IN HUMAN NEURONS TO PROMOTE DISEASE MODELING AND DRUG DISCOVERY

CROSS-REFERENCE TO RELATED APPLICATIONS

This patent application claims the benefit of priority of U.S. Provisional Patent Application No. 62/945,386, filed Dec. 9, 2019, which is incorporated herein by reference in its entirety.

SEQUENCE LISTING STATEMENT

A computer readable form of the Sequence Listing is filed with this application by electronic submission and is incorporated into this application by reference in its entirety. The Sequence Listing is contained in the ASCII text file created on May 26, 2021, having the file name "20-1405-US_Sequence-Listing_ST25.txt" and is 1,000 bytes in size.

STATEMENT REGARDING FEDERALLY SPONSORED RESEARCH OR DEVELOPMENT

Not applicable.

BACKGROUND

Human pluripotent stem cells (hPSCs) are a potential tool for modeling diseases and for testing drugs. An advantage of the hPSC platform is an ability to capture the human genetic background by establishing patient specific iPSCs or by introducing disease-related mutations into naïve hES or hiPS cells. However, the iPSC reprogramming process re-sets the age of the somatic donor cells and hPSC-derived somatic cells match the stage of fetal development based on transcriptional and functional profiling.

Age is the leading risk factor for neurodegenerative diseases like Amyotrophic lateral sclerosis (ALS), Parkinson's disease (PD) and Alzheimer's disease (AD). Hence, modeling degenerative diseases using hPSC-derived cells, including neurons, is very difficult. One approach is to introduce expression of progerin to induce gaining of the hPSC-derived neurons, thus triggering age-related phenotypes in iPSC-derived neurons. Such a strategy adds complexity to the model system by altering the genetic background and making deciphering phenotypes difficult. Another alternative is using direct reprogramming of somatic cells like fibroblast cells to neurons, which is possible for small scale efforts but it is not feasible in large scale; moreover, the resultant neurons are limited to specific glutamatergic neurons. Therefore, there is a need to create a non-genetic means to systematically and reproducibly induce "aging" in neurons.

Thus, there is an ongoing need for non-genetic methods and compositions to systematically and reproducibly induce "aging" in hPSC-derived neurons for disease modeling and drug discovery.

BRIEF SUMMARY

Described herein are methods, compositions, and kits that address the aforementioned drawbacks of conventional differentiation and "aging" protocols to model neurodegenerative diseases in senescent neurons.

In a first aspect, provided herein is an in vitro method for inducing cellular senescence in human neurons. The method can comprise contacting human neurons in vitro to a culture medium comprising one or more agents selected from an inhibitor of DNA glycosylase 1, an autophagy inhibitor, and an HIV protease inhibitor; and culturing the contacted neurons in the presence of the culture medium for about two to about four days to generate a population of chemically induced senescent (CIS) neurons. Exemplary but not limiting agents include SBI-0206965, Lopinavir, and O151. The culture medium can further comprise sodium butyrate and, optionally, SCR-7. The CIS neurons can express senescence-associated biomarkers including β-galactosidase and exhibit decreased expression of one or more of H3k9Me3, Lap2β, and HP1γ relative to control neurons. These neurons can be human pluripotent stem cell (hPSC)-derived neurons, primary neurons, or induced neurons (iNs). hPSC-derived neurons can be derived from human embryonic stem cells (ESCs) or human induced pluripotent stem cells (iPSCs). Human iPSCs can be obtained by reprogramming a somatic cell of an individual having a neurodegenerative disease, whereby the CIS neurons exhibit one or more morphological features characteristic of the neurodegenerative disease. The neurodegenerative disease can be ALS, Alzheimer's disease (AD), Parkinson's disease (PD), and age-related macular degeneration. The neurodegenerative disease can be Amyotrophic lateral sclerosis (ALS) and the morphological features can include axonal swelling, axonal degeneration, reduced expression of H3K9Me9 and Lap2β, increased expression of phosphorylated neurofilament, and increased protein aggregation relative to control neurons. The culture medium can be a neuron maturation medium comprising N2, B27, GDNF, BDNF, dibutyryl cAMP, doxycycline, and laminin.

In another aspect, provided herein is a substantially pure population of chemically induced senescent neurons obtained according to a method of this disclosure.

In a further aspect, provided herein is a composition comprising O151, SBI-0206965, and Lopinavir. In some embodiments, the composition is formulated as a cell culture medium.

In a further aspect, provided herein is a composition comprising O151, SBI-0206965, and Sodium Butyrate. In some embodiments, the composition is formulated as a cell culture medium.

In another aspect, provided herein is a method for in vitro screening of a test substance. The method can comprise contacting a test substance to chemically induced senescent (CIS) neurons obtained according to a method of this disclosure; and detecting an effect of the test substance agent on the contacted CIS neurons. The method can comprise detecting at least one effect of the agent on morphology, proliferation, or life span of contacted neurons, whereby an agent that reduces axonal swelling, axonal degeneration, increases expression of H3K9Me9 and Lap2β, reduces expression of phosphorylated neurofilament, and reduces protein aggregation relative to control is identified as having therapeutic activity for treating a neurodegenerative disease.

In another aspect, provided herein is use of chemically induced senescent (CIS) neurons obtained according to a method of this disclosure in a drug discovery screen.

These and other features, objects, and advantages of this invention will become better understood from the description that follows. In the description, reference is made to the accompanying drawings, which form a part hereof and in which there is shown by way of illustration, not limitation, embodiments of the invention. The description of preferred embodiments is not intended to limit the invention and to cover all modifications, equivalents and alternatives. Reference should therefore be made to the claims recited herein for interpreting the scope of the invention.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

This invention will be better understood and features, aspects and advantages other than those set forth above will become apparent when consideration is given to the following detailed description thereof. Such detailed description makes reference to the following drawings, wherein:

FIG. 11 is a table listing small molecules used in the studies presented herein.

Figure 1:
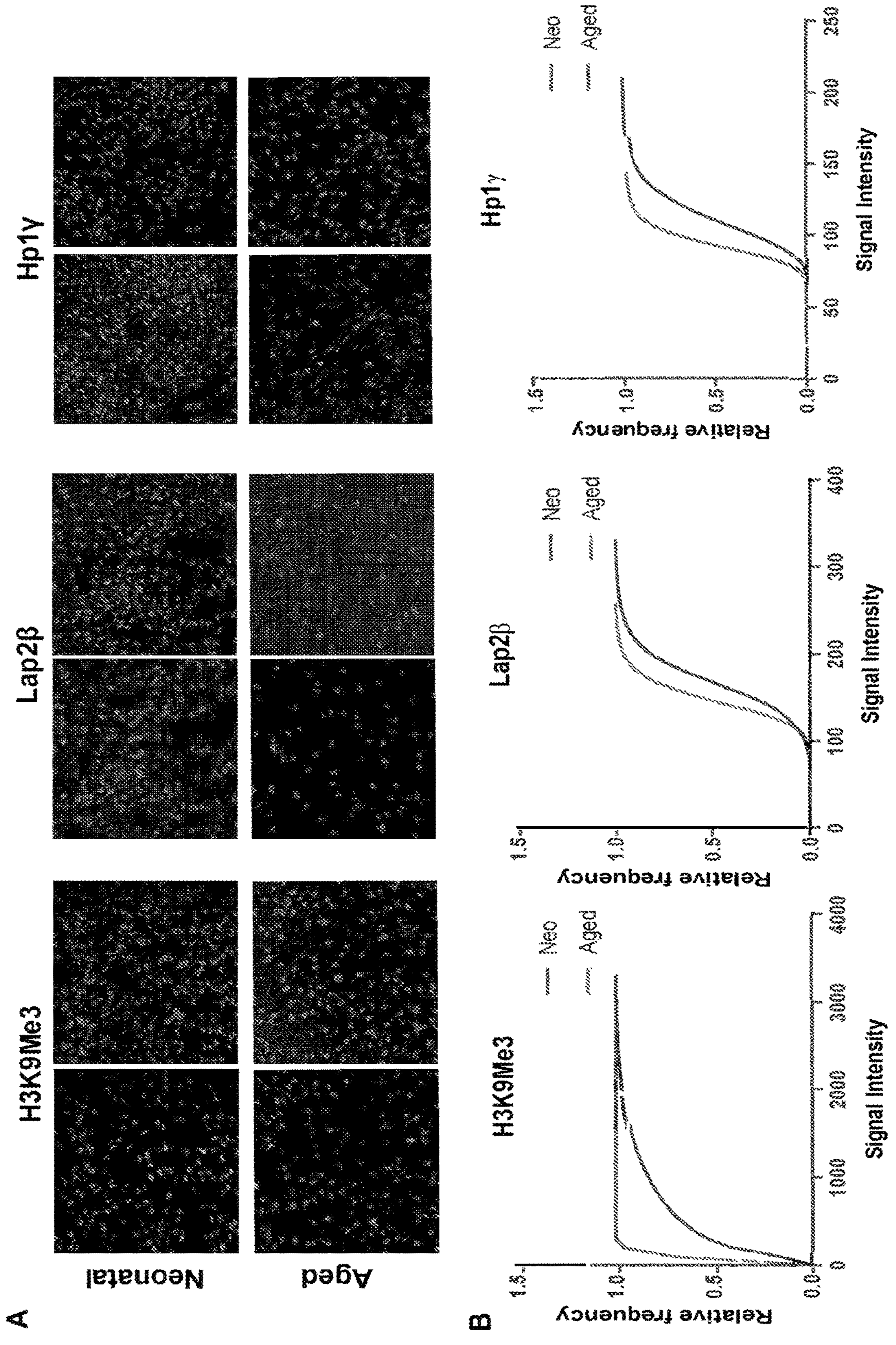
FIGS. 1A-1D demonstrate establishing senescence markers in the human neonatal and aged fibroblasts and inducing senescence in neonatal fibroblasts using small molecules. Immunostaining imaging of H3k9Me3, Lap2β and Hp1γ proteins for both neonatal and aged fibroblasts (FIG. 1A). Frequency distribution analysis for different bins of signal intensity in high content imaging for H3k9Me3, Lap2β and Hp1γ proteins in male neonatal and aged (72 years old) fibroblasts (FIG. 1B). Frequency distribution analysis for H3k9Me3, Lap2β and Hp1γ protein expression in male neonatal fibroblasts treated with different small molecules, dashed red line is control and top seven molecules for each protein showed in the graph (FIG. 1C). Mean difference for signal intensity of all 25 small molecules depicted as mean±95% confidence Intervals compared to the DMSO control group. The zero line means no difference compare to control and if difference in the mean not touching the reference line then changes in expression are significant (FIG. 1D).
Figure 1:
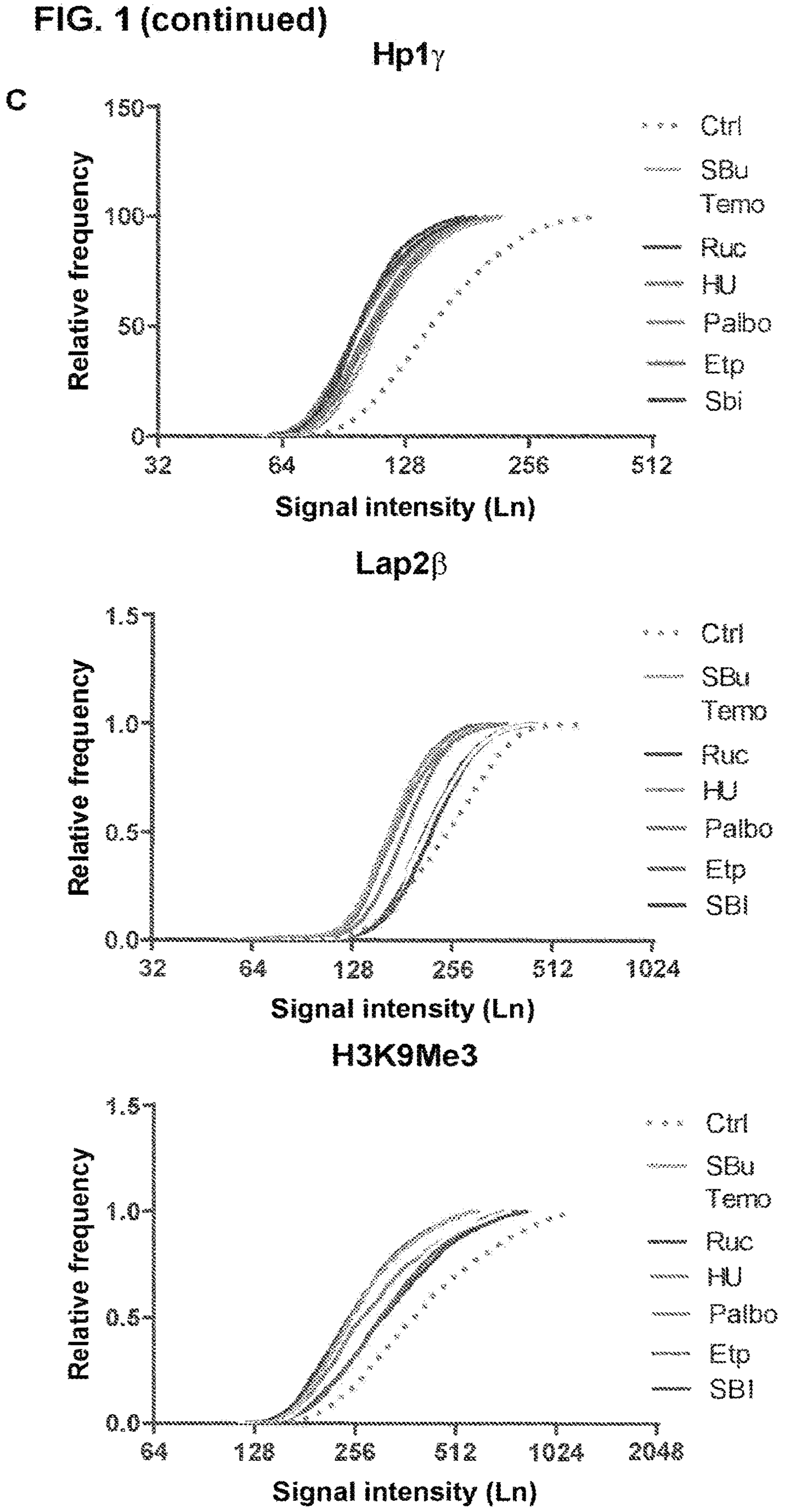
Figure 1:
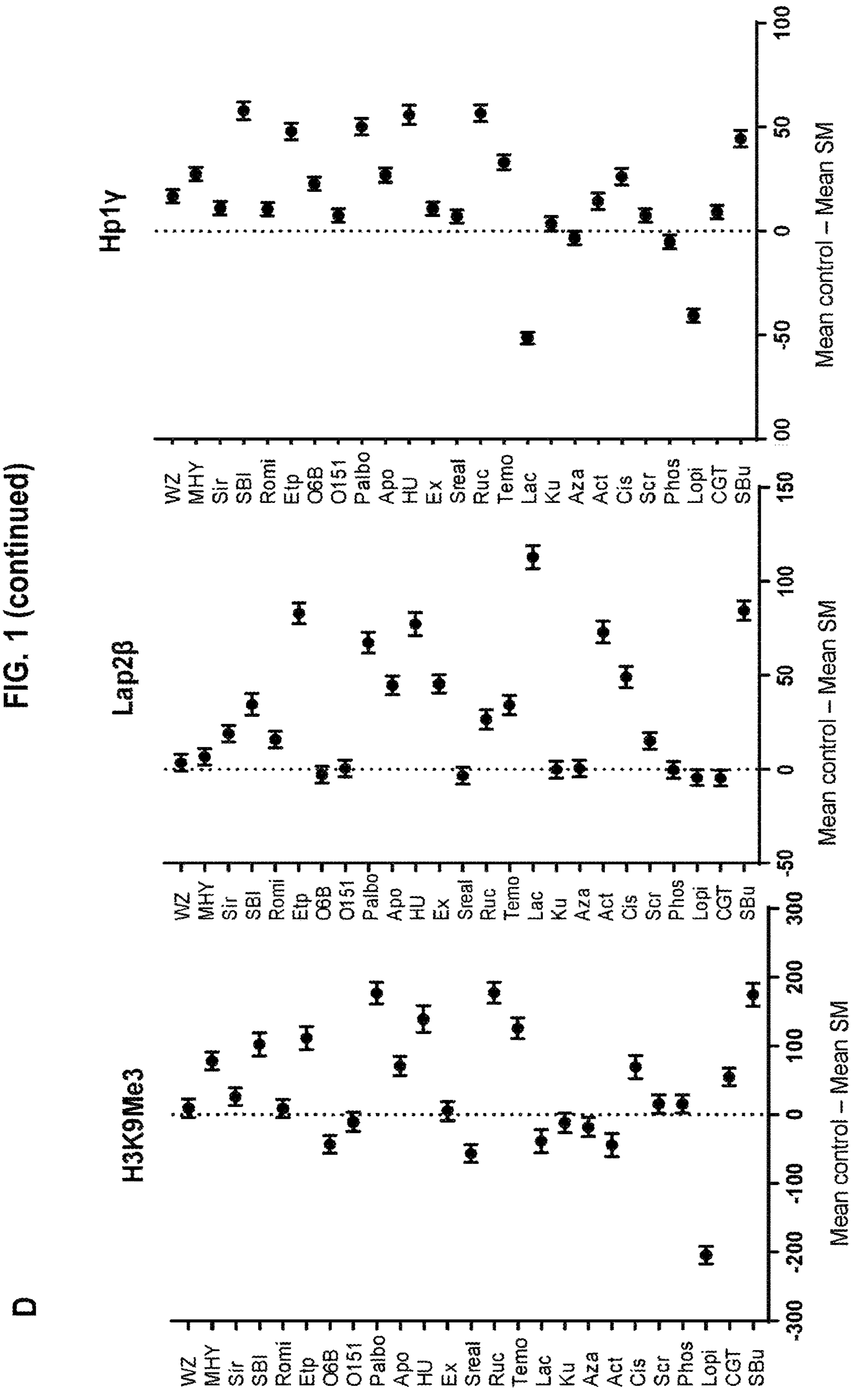

While this invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

This invention relates to development of a cocktail of chemical molecules that induce cellular senescence in embryonic fibroblasts and multiple types of hPSC-derived neurons in less than a week. As demonstrated in this disclosure, this senescence cocktail was developed through systematic chemical screening and validated in both fibroblasts and different neuronal types for its ability to induce cellular senescence. Validation studies demonstrated that the senescence cocktail results in chemically induced senescence (CIS) in cortical neurons (those affected in Alzheimer's disease), midbrain dopamine neurons (those affected in Parkinson's disease) and motor neurons (those affected in ALS). Using motor neurons derived from ALS patient-derived iPSCs, it was demonstrated that the cocktail-treated neurons manifested disease related phenotypes earlier and more consistently. The methods and compositions described herein permit unprecedented modeling of neurological diseases and enable human stem cell-based drug testing, for example using iPSCs from individuals having degenerative diseases. This development represents a significant advancement over current state-of-the-art methods. In particular, the methods make it possible to induce senescence phenotypes in differentiated neurons without modifying the cell's genetic background. The ability of their cocktail to 'age' primary cells, stem cell-derived cells, and neurons generated via direct conversion from fibroblasts (i.e., without going through a progenitor cell stage) has been validated as set forth herein. Accordingly, the cocktail can be used widely across many cell types, regardless of their history or pluripotency. The methods are scalable and yield more predictable results than existing techniques.

Accordingly, in a first aspect, this disclosure provides methods inducing cellular senescence in human neurons and for generating chemically induced senescent neurons that are age-appropriate for various applications including, for example, modeling neurodegenerative disease and particularly age-associated neurodegenerative disease. In particular, this disclosure provides in vitro methods to chemically induce senescence in neurons including, without limitation, primary, induced, and hPSC-derived cortical, midbrain dopamine, and motor neurons. As used herein, the term "chemically induced senescence" refers to cells that have been treated with one or more small molecules and, as a result of the treatment, the cells remain in cell cycle arrest in which cells are metabolically active and adopt characteristic phenotypic changes. The phenotypic changes include, without limitation, morphological changes, changes in gene expression (including expression of senescent biomarkers), changes in functional activity, and secretion of senescence-associated growth factors, chemokines, and cytokines. Senescence in a cell can be indicated by changes in the cell that can include, as compared with a reference cell (e.g., a cell not treated/contacted to a chemical composition described herein), reduction in proliferation of a cell, accumulation of lipofuscin, increase in β-galactosidase activity, increase in mitochondrial reactive oxygen species, or a combination thereof.

In exemplary embodiments, these methods comprise contacting human neurons in vitro to a chemical cocktail comprising one or more agents that can include an inhibitor of DNA glycosylase 1, an autophagy inhibitor, and an HIV protease inhibitor, and culturing the contacted neurons in the presence of this chemical cocktail in a culture medium for about two to about four days to generate a population of chemically induced senescent (CIS) neurons. In some embodiments, the inhibitor of DNA glycosylase 1, autophagy inhibitor, and HIV protease inhibitor are small molecules, inter alia, that are listed in FIG. 11. Advantageously, the agents are SBI-0206965, Lopinavir, and O151 (referred to as the "SLO" cocktail" in the Examples). In some embodiments, the chemical cocktail further comprises sodium butyrate. In other embodiments, the agents are SBI-0206965, sodium butyrate, and O151 (referred to as the "SSO" cocktail" in the Examples).

Other inhibitors of 8-oxoguanine DNA glycosylase (OGG1) appropriate for use according to these methods include, without limitation, SU0268, CGP-74514A, NCGC000188618, NCGC000188616, NCGC000188617, NCGC000188619, 3,4-Dichlorobenzo[b]thiophene-2-carbohydrazide (08), O1, O40, O105, O159, O154, O167, O151-Hy, O155, O156, O158, O179, and O181. See Jacobs A C et al. PLoS One. 8(12): e81667 (2013); Lloyd R S et al. US20170038365.

Other autophagy inhibitors appropriate for use according to these methods include, without limitation, Autophinib, Nimodipine, SBI-0206965, MRT68921, MRT 68921 dihydrochloride, Liensinine, LYN-1604, PHY34, Spautin-1, ROC-325, PIK-III, ULK-101, EAD1, CA-5f, Lucanthone, IITZ-01, MHY1485, Lys05, DC661, Hydroxychloroquine Sulfate, Chloroquine diphosphate, and 3-Methyladenine.

Other HIV protease inhibitors appropriate for use according to these methods include, without limitation, GGT1298, GGT12147, Phosphoramidon Disodium Salt, FTI 277 HCl, Tipifarnib (R115777), LB42708, AG1343 (Nelfinavir mesylate), Lonafarnib, stavudine, tipranavir, Darunavir, Saquinavir mesylate, Ritonavir, and other endopeptidase inhibitors that target the gene Zinc Metallopeptidase STE24 (ZMPSTE24).

In some embodiments, the agents described herein are contacted to neurons in a culture medium. An inhibitor of DNA glycosylase 1 can be present in the culture medium at a concentration between about 0.1 μM and about 10 μM (e.g., 0.1 μM, 0.2 μM, 0.3 μM, 0.4 μM, 0.5 μM, 1 μM, 1.5 μM, 2 μM, 2.5 μM, 3 μM, 3.5 μM, 4 μM, 4.5 μM, 5 μM, 6 μM, 7 μM, 8 μM, 9 μM, 10 μM). Advantageously, the inhibitor of DNA glycosylase 1 is O151 and is present at a concentration of about 1 μM.

An autophagy inhibitor can be present in the culture medium at a concentration between about 1 μM and about 20 μM (e.g., 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM). Advantageously, the autophagy inhibitor is SBI-0206965 and is present at a concentration of about 10 μM.

An HIV protease inhibitor can be present in the culture medium at a concentration between about 0.1 μM and about 10 μM (e.g., 0.1 μM, 0.2 μM, 0.3 μM, 0.4 μM, 0.5 μM, 1 μM, 1.5 μM, 2 μM, 2.5 μM, 3 μM, 3.5 μM, 4 μM, 4.5 μM, 5 μM, 6 μM, 7 μM, 8 μM, 9 μM, 10 μM). Advantageously, the HIV protease inhibitor is Lopinavir and is present at a concentration of about 1 μM.

As described in this disclosure, the CIS neurons express senescence associated-biomarkers such as 3-Gal and exhibit decreased expression of one or more of H3k9Me3, Lap2β, and HP1γ relative to control neurons. When the CIS neurons are obtained from neurons derived from a patient having a neurodegenerative disease, those CIS neurons also exhibit morphological features characteristic of the neurodegenerative disease. For example, CIS neurons derived from a patient having Amyotrophic lateral sclerosis (ALS), or neurons having a genetic mutation associated with ALS, exhibit morphological features such as axonal swelling, axonal degeneration, reduced expression of H3K9Me9 and Lap2β, increased expression of phosphorylated neurofilament, and increased protein aggregation relative to control neurons. In this manner, chemically induced senescent neurons obtained by these methods can recapitulate cellular and subcellular phenotypes observed in individuals with the neurodegenerative disease.

Neurons for use with the methods and compositions described herein can be obtained from a variety of sources. In some embodiments, the neurons are primary neurons. In other embodiments, the neurons are induced neurons or "iNs." Induced neurons (iNs) are neurons obtained by direct in vitro conversion of differentiated somatic cells (e.g., fibroblasts) to functional neurons without reversion to a progenitor cell stage. Induced neurons are non-proliferating, present an alternative to induced pluripotent stem cells for obtaining patient- and disease-specific neurons, and have been shown to retain the senescence phenotype (or "age") of the fibroblasts from which they are converted. Methods for direct conversion of fibroblasts to functional human neurons are known and generally involve vector-based delivery of neural conversion factors into the fibroblasts. The particular combination of neural conversion factors used depends on the desired neuronal subtype. In some embodiments, the iNs are obtained using differentiated cells such as fibroblasts obtained from an individual having or suspected of having a neurodegenerative disease such as, for example, ALS, Alzheimer's disease (AD), Parkinson's disease (PD), or age-related macular degeneration.

In some embodiments, the neurons are generated by differentiation of stem cells including from human embryonic stem cells (hESCs), induced pluripotent stem cells (iPSCs), multipotent stem cells, unipotent stem cells, or combinations thereof, according to any appropriate differentiation protocol. For example, in some embodiments, the neurons are human pluripotent stem cell-derived neurons. As used herein, "pluripotent stem cells" appropriate for use according to a method of the invention are cells having the capacity to differentiate into cells of all three germ layers. Suitable pluripotent cells for use herein include human embryonic stem cells (hESCs) and human induced pluripotent stem (iPS) cells. As used herein, "embryonic stem cells"

or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60 andTRA-1-81, and appear as compact colonies having a high nucleus-to-cytoplasm ratio and prominent nucleolus. ESCs are commercially available from sources such as WiCell Research Institute (Madison, Wis.). As used herein, "induced pluripotent stem cells" or "iPS cells" mean a pluripotent cell or population of pluripotent cells that can vary with respect to their differentiated somatic cell of origin, that can vary with respect to a specific set of potency-determining factors, and that can vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007).

Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60 or Tra-1-81, but not SSEA-1). Induced pluripotent stem cells, however, are not immediately derived from embryos. As used herein, "not immediately derived from embryos" means that the starting cell type for producing iPS cells is a non-pluripotent cell, such as a multipotent cell or terminally differentiated cell, such as somatic cells obtained from a post-natal individual.

Subject-specific somatic cells for reprogramming into induced pluripotent stem cells can be obtained or isolated from a target tissue of interest by biopsy or other tissue sampling methods. For example, subject-specific cells can be expanded, differentiated, genetically modified, contacted to polypeptides, nucleic acids, or other factors, cryo-preserved, or otherwise modified prior to reprogramming into reprogramming into induced pluripotent stem cells and aging according to the methods of this disclosure.

In some embodiments, the cells can be autologous or allogeneic cells (relative to a subject to be treated or who can receive the cells). Thus, somatic cells or adult stem cells can be obtained from a mammal suspected of having or developing a neurodegenerative condition or neuropathic disease (e.g., ALS, Alzheimer's disease (AD), Parkinson's disease (PD), age-related macular degeneration), and the cells so obtained can be reprogrammed into in vitro derived neurons for chemically induced senescence using the compositions and methods described herein.

Prior to culturing hPSCs (e.g., hESCs or hiPSCs) under conditions that promote differentiation into neurons, hPSCs can be cultured in the absence of a feeder layer (e.g., a fibroblast layer) on a substrate suitable for proliferation of hPSCs, e.g., MATRIGEL™, vitronectin, a vitronectin fragment, or a vitronectin peptide, or Synthemax®. In some embodiments, the hPSCs are passaged at least 1 time to at least about 5 times in the absence of a feeder layer. Suitable culture media for passaging and maintenance of hPSCs include, but are not limited to, mTeSR® and E8™ media. In some embodiments, the hPSCs are maintained and passaged under xeno-free conditions, where the cell culture medium is a chemically defined medium such as E8 or mTeSR, but the cells are maintained on a completely defined, xeno-free substrate such as human recombinant vitronectin protein or Synthemax® (or another type-of self-coating substrate). In one embodiment, the hPSCs are maintained and passaged in E8 medium on human recombinant vitronectin or a fragment thereof, a human recombinant vitronectin peptide, or a chemically defined self-coating substrate such as Synthemax®.

Any appropriate method can be used to detect expression of biological markers characteristic of cell types described herein. For example, the presence or absence of one or more biological markers (e.g., neural markers) can be detected using, for example, RNA sequencing, immunohistochemistry, polymerase chain reaction, qRT-PCR, or other technique that detects or measures gene expression. Suitable methods for evaluating the above-markers are well known in the art and include, e.g., qRT-PCR, RNA-sequencing, and the like for evaluating gene expression at the RNA level. Differentiated cell identity is also associated with downregulation of pluripotency markers such as NANOG and OCT4 (relative to human ES cells or induced pluripotent stem cells). Quantitative methods for evaluating expression of markers at the protein level in cell populations are also known in the art. For example, flow cytometry is typically used to determine the fraction of cells in a given cell population that express (or do not express) a protein marker of interest (e.g., neural markers).

Drug Discovery Methods

In another aspect, this invention provides methods for producing and using chemically induced senescent neurons for high throughput screening of candidate test substances and identifying agents having therapeutic activity to slow, stop, and/or reverse progression of a neurodegenerative disease. Such agents can be used to treat neurodegenerative disease in subjects in need thereof.

In exemplary embodiments, the methods employ chemically induced senescent neurons of this disclosure for screening pharmaceutical agents, small molecule agents, or the like. For example, chemically induced senescent neurons can be contacted with a test substance and the contacted CIS neurons can be studied to detect a change in a biological property of the neurons in response to exposure to the test substance.

As described herein, the methods of this disclosure are advantageous over conventional in vitro and in vivo methodologies for drug discovery screening. In particular, the methods described herein provide sensitive, reproducible, and quantifiable methods for screening test substances. Using these methods it is possible to rapidly screen test substances for therapeutic activity on neurons that exhibit cellular and subcellular phenotypes associated with a neurodegenerative disease without having to wait for the disease to manifest in a human subject and with more reproducibility and predictability than screens using non-senescent neurons. Indeed, these in vitro screening methods can be conducted without the need for a human subject or animal models. The methods can be conducted economically (e.g., using multi-well plates that require minimal amounts of a test substance) and are readily adapted to high throughput methods (e.g., using robotic or other automated procedures). The methods are better alternatives to in vivo animal assays that are quantifiable assays but are error-prone, require a large number of animals, and are not easily standardized between laboratories or scalable for high-throughput screening. Shortcomings of animal-based assays have prompted regulatory agencies, including the Food and Drug Administration (FDA) and the United States Department of Agriculture, to promote the development of cell-based models comprising more physiologically relevant human cells and having the sensitivity and uniformity necessary for large-scale, quantitative in vitro modeling and screening applications (National Institutes of Health, 2008).

Following exposure to the test substance, a change in a biological property of the senescent neurons treated with the test substance is then detected. Such a change in a biological property includes, for example, a change in morphology or life span, a change in protein aggregation, a change in expression of phosphorylated neurofilament and other biological markers (e.g., a DNA, RNA, protein) associated with neurodegenerative disease.

The manner in which a test compound has an effect on a particular biological activity of cells in the senescent neurons will depend on the nature of the test compound and the particular biological activity being assayed. However, methods of this invention will generally include steps for culturing senescent neurons as provided herein in the presence of a test substance, assaying a selected biological property or activity of the senescent neurons, and comparing values determined in the assay to the values of the same assay performed using the senescent neurons but cultured in the absence of the test substance and/or in the presence of appropriate controls.

A change in a biological property can be detected, for example, by the following non-limiting methods. Expression of DNAs, RNAs (including microRNAs, siRNAs, tRNAs, snRNAs, mRNAs, and non-coding RNAs), proteins, peptides, and metabolites can be assessed by conventional expression assessment methods. In some embodiments, detecting comprises performing a method selected from the group consisting of RNA sequencing, gene expression profiling, transcriptome analysis, cell proliferation assays, metabolome analysis, detecting reporter or sensor, protein expression profiling, Forster resonance energy transfer (FRET), metabolic profiling, and microdialysis. In some embodiments, the agent can be screened for an effect on gene expression, and detecting such effects can comprise assaying for differential gene expression relative to uncontacted neurons.

In exemplary embodiments, detecting and/or measuring a positive or negative change in a level of expression of at least one gene following exposure (e.g., contacting) of a test compound to senescent neurons comprises whole transcriptome analysis using, for example, RNA sequencing. In such embodiments, gene expression is calculated using, for example, data processing software programs such as Light Cycle, RSEM (RNA-Seq by Expectation-Maximization), Excel, and Prism. See Stewart et al., *PLoS Comput. Biol.* 9:e1002936 (2013). Where appropriate, statistical comparisons can be made using ANOVA analyses, analysis of variance with Bonferroni correction, or two-tailed Student's t-test, where values are determined to be significant at $P<0.05$. Any appropriate method can be used to isolate RNA or protein from neural constructs. For example, total RNA can be isolated and reverse transcribed to obtain cDNA for sequencing.

As used herein, "test substances" can include, but are not limited to, single compounds such as natural compounds, organic compounds, inorganic compounds, proteins, antibodies, peptides, and amino acids, as well as compound libraries, expression products of gene libraries, cell extracts, cell culture supernatants, products of fermenting microorganisms, extracts of marine organisms, plant extracts, prokaryotic cell extracts, unicellular eukaryote extracts, and animal cell extracts. These can be purified products or crude purified products such as extracts of plants, animals, and microorganisms. Test compounds can include FDA-approved and non-FDA-approved drugs (including those that failed in late stage animal testing or in human clinical trials) having known or unknown toxicity profiles. Test substances can be isolated from natural materials, synthesized chemically or biochemically, or prepared by genetic engineering. "Test substances" also encompass mixtures of the above-mentioned substances.

Test compounds can be dissolved in a solvent such as, for example, dimethyl sulfoxide (DMSO) prior to contacting CIS neurons as described herein. In some embodiments, identifying agents comprises analyzing the contacted CIS neurons for positive or negative changes in biological activities including, without limitation, gene expression, protein expression, cell viability, and cell proliferation. For example, microarray methods can be used to analyze gene expression profiles prior to, during, or following contacting the plurality of test compounds to the expanded population. In some embodiments, methods of this invention further comprise additional analyses such as metabolic assays and protein expression profiling.

Pharmaceutical agents selected as having therapeutic activity to treat a neurodegenerative disease accordingly to the screening methods of this disclosure can be further screened as necessary by conducting additional drug effectiveness tests and safety tests, and further conducting clinical tests in human patients.

Article of Manufacture

In another aspect, this disclosure provides kits for chemically inducing senescence in human neurons. Components of these kits can include a composition comprising one or more agents such as an inhibitor of DNA glycosylase 1, an autophagy inhibitor, and an HIV protease inhibitor. In some embodiments, the agents are SBI-0206965, Lopinavir, and O151. In some embodiments, the kit further comprises instructions for using chemically induced senescent neurons for screening test substances to identify those that exert a particular effect on the senescent neurons.

Unless defined otherwise, all technical and scientific terms used herein have the same meaning as commonly understood by one of ordinary skill in the art to which the invention pertains. Although any methods and materials similar to or equivalent to those described herein can be used in the practice or testing of this invention, the preferred methods and materials are described herein.

In the specification and in the claims, the terms "including" and "comprising" are open-ended terms and should be interpreted to mean "including, but not limited to . . . ." These terms encompass the more restrictive terms "consisting essentially of" and "consisting of." As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising," "including," "characterized by," and "having" can be used interchangeably.

As used herein, "a medium consisting essentially of" means a medium that contains the specified ingredients and those that do not materially affect its basic characteristics.

As used herein, "about" means within 5% of a stated concentration range, density, temperature, or time frame. Alternatively, and particularly in biological systems, the terms "about" and "approximately" can mean values that are within an order of magnitude, advantageously within 5-fold and more advantageously within 2-fold of a given value. Numerical quantities given herein are approximate unless stated otherwise, meaning that the term "about" or "approximately" can be inferred when not expressly stated.

The invention will be more fully understood upon consideration of the following non-limiting Examples.

EXAMPLES

Example 1—Chemically Induced Senescence in Neurons Promotes Phenotypic Presentation of Neurodegeneration This example describes development and validation of a chemical cocktail to induce senescence of pluripotent stem cell-derived neurons. Small molecules were screened to identify those that induce embryonic fibroblasts to exhibit age-related features as presented by aged fibroblasts. Next, a cocktail of small molecules was selected for the ability to induce senescence in fibroblasts and cortical neurons without causing apoptosis. The utility of the "aging cocktail" was validated in motor neurons derived from ALS patient induced pluripotent stem cells (iPSCs). In the presence of the "aging cocktail," ALS patient iPSC-derived motor neurons exhibited protein aggregation and axonal degeneration substantially earlier than those without the treatment with the cocktail. The "aging cocktail" will improve the manifestation of disease-related phenotypes in neurons derived from iPSCs in a range of neurological disorders in a consistent manner, enabling the generation of reliable drug discovery platforms.

Results

Identification of small molecules that induce senescence in neonatal fibroblasts: Primary human fibroblasts retain age-related marks depending on the age of the individual from which the cells are isolated (22). These cells are thus appropriate reference for studying cellular senescence (CS). Neonatal fibroblasts were compared with those from 72-year and 62-year old donors by examining the expression of age-related markers H3k9Me3 (Histone 3 lysine 9 trimethylation), Lap2β (Lamina-associated polypeptide 2β), and HP1γ (heterochromatin protein 1γ). We found that neonatal fibroblasts expressed a higher level of H3k9Me3, Lap2β, HP1γ than old fibroblasts (72 years). In contrast, the old fibroblasts expressed the senescence associated β-Gal (FIGS. 1A-1B, FIG. 7A). These findings are consistent with previous observations (Miller J D et al. *Cell Stem Cell* 13(6):691-705 (2013)), suggesting that these markers are reliable readouts for assessing CS.

Figure 7:
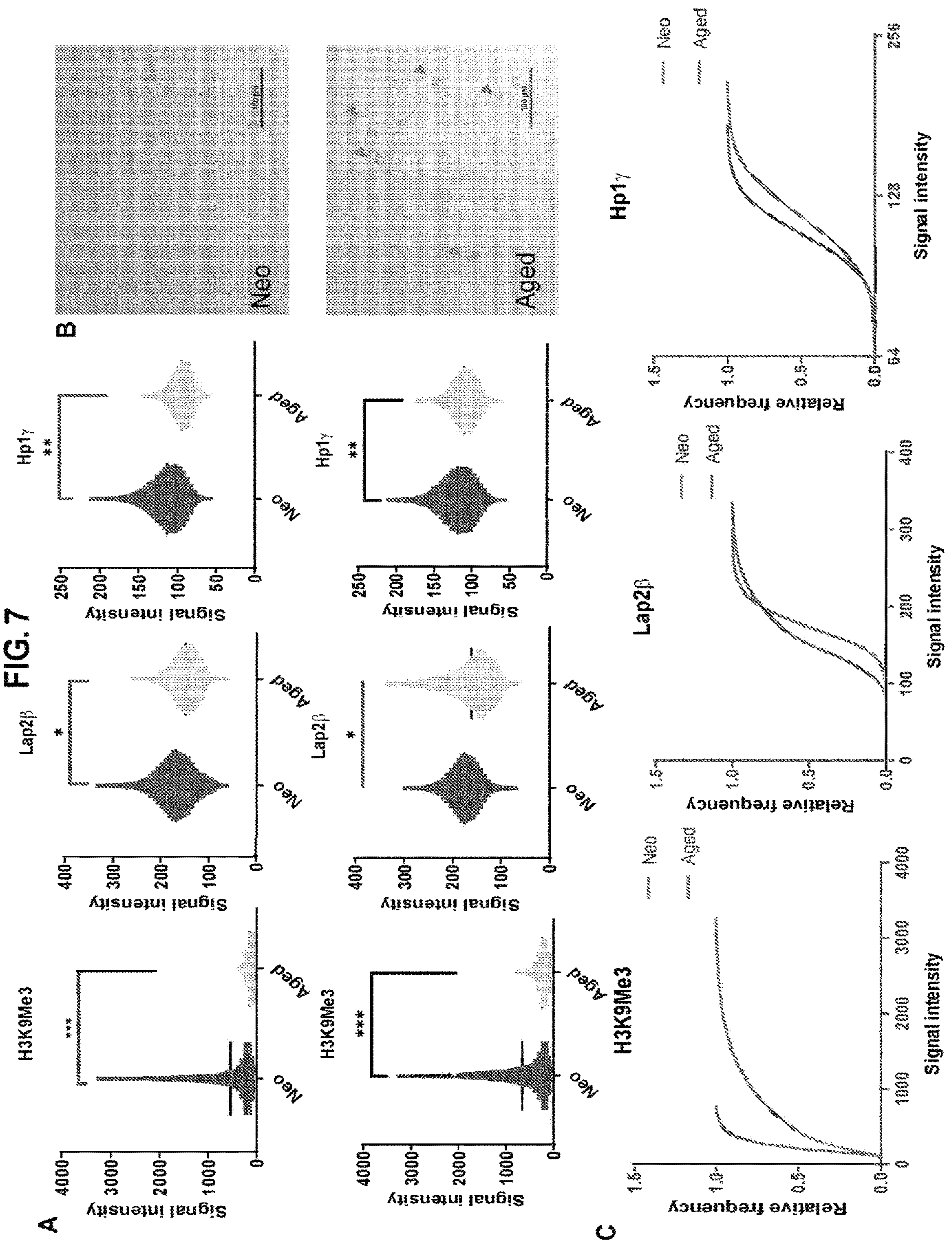
FIGS. 7A-7E (which are related to FIGS. 1A-1D) present individual values for H3k9Me3, Lap2β and Hp1γ expressions in both male (upper panel) and female (lower panel) fibroblast cells (FIG. 7A) and phase contrast images of senescence associated β-Galactosidase staining for both neonatal and aged (female 62 years old) fibroblasts (FIG. 7B). Frequency distribution analysis of results from high content imaging for H3k9Me3, Lap2β and Hp1γ proteins in female neonatal and aged (62 years old) fibroblasts (FIG. 7C). Cell toxicity assay for small molecules in the used concentration in actual experiment compared to the DMSO control neonatal fibroblasts (FIG. 7D). Phase contrast images of senescence associated β-Galactosidase staining for top seven molecules that induced senescence in neonatal fibroblast (FIG. 7E), and quantification results for percentage of positive cells (all numbers across replicates pooled) and divided to high expression and moderate expression classes based on intensity of staining (FIG. 7F). (*: $p<0.05$, : $p<0.01$, *:$p<0.001$ one-way ANOVA with Dunnett's multiple comparison test).
Figure 7:
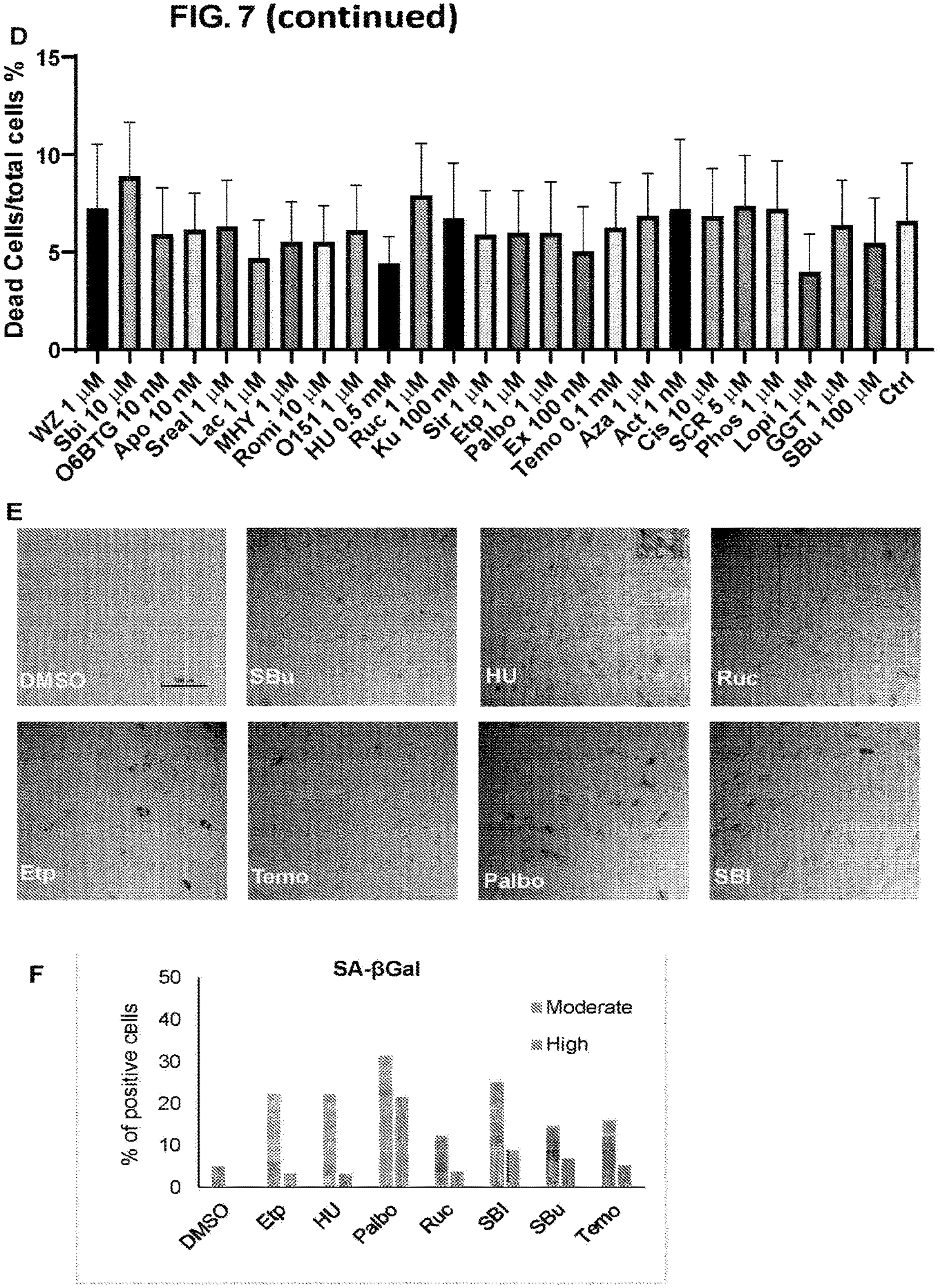

Molecules that could induce senescence phenotypes in the neonatal fibroblasts were then identified, from 25 small molecules known to affect pathways involved in CS, including those that trigger autophagy, activate Akt signaling, and inhibit mTOR, HDAC, ZMPSTE24, and Sirtuin signaling (23) (FIG. 11). Toxicity of these molecules in their minimum effective concentrations was evaluated, based on previous studies using calcein AM and ethidium homodimer (EthD-1) fluorescent dyes to distinguish live versus dead cells. None of the small molecules induced cell death beyond the DMSO control (5-10% cell death) (FIG. 7). By culturing the neonatal fibroblasts in the presence of the small molecules at an effective dose for 5 consecutive days and examining the expression of the above aging markers, it was found that more than half of the molecules (13 molecules, $p \leq 0.001$, Table 1) significantly decreased expression of all three readouts (FIGS. 1C, 1D). Among the 13 molecules, seven also induced the expression of β-Gal, another consensus marker for CS (FIGS. 7E, 7F). Thus, a set of small molecules that induce senescence phenotypes in neonatal fibroblasts was identified.

Figure 2:
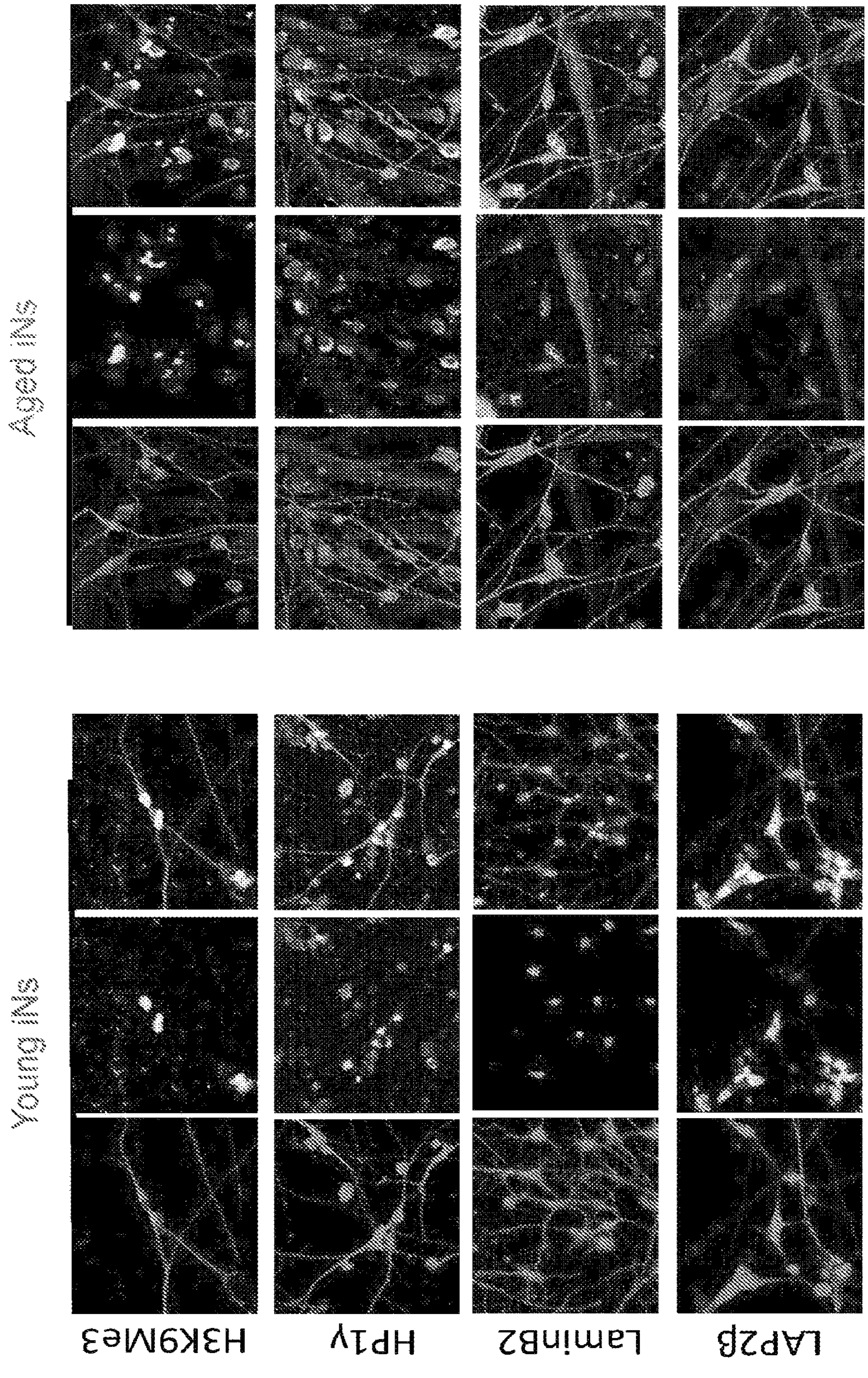
FIGS. 2A-2G demonstrate that cellular senescence marks are preserved during direct conversion of fibroblasts to neurons ("induced neurons" or "iNs)". Immunostaining for H3k9Me3, LaminB2, Lap2β, and Hp1γ co-stained with TUJ1 (red) in induced neurons (iNs) derived from fibroblasts from both neonatal and 72 years age donor individuals (FIG. 2A). Quantification results for percentage of TUJ1 positive neurons (FIG. 2B), and mean signal intensity for H3k9Me3, Lap2β, LaminB2, and Hp1γ (FIG. 2C). Quantification results for Hoechst signal intensity (FIG. 2D), Nucleus roundness (FIG. 2E), Nucleus ratio (FIG. 2F) and Nucleus area (FIG. 2G) for both young and aged iNs. (ns: not significant, *: $p<0.05$, : $p<0.01$, *:$p<0.001$ unpaired t-test).
Figure 2:
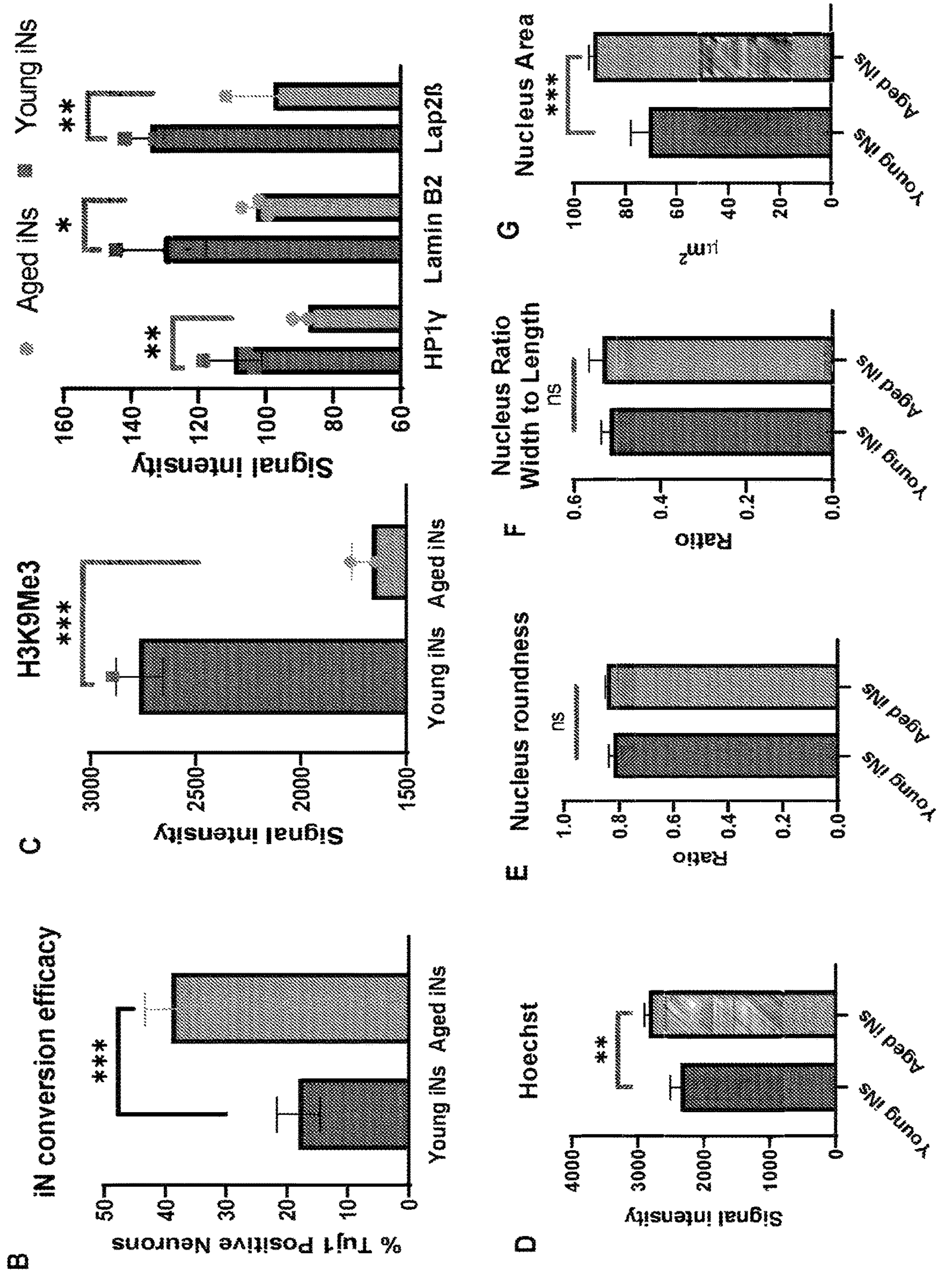

Identifying small molecule cocktails that enhance neuronal senescence: Epigenetic marks, including those associated with aging, are largely erased during reprogramming to iPSCs (6, 24). Consequently, cells differentiated from iPSCs, including neurons, behave like those in embryonic development. In contrast, neurons directly converted from fibroblasts by forced expression of transcription factors retain much of the age-related signatures in their parental somatic cells (13). To validate this phenomenon and to establish CS readouts in neurons, both young and old human fibroblasts were reprogrammed to neurons using combination of gene overexpression and small molecules. Mertens J et al. *Cell Stem Cell* 17(6):705-18 (2015). Both neonatal and aged fibroblasts were transduced with lentiviral particles for Eto and XTP-Ngn2:2A:Ascl1 (N2A) and expanded in the presence of G418 and puromycin for at least three passages. After 3 weeks of DOX treatment, about 50% of the cells became induced neurons (iNs), exhibiting polarized morphology and expressing neuronal proteins like β-III tubulin (FIG. 2A). Importantly, iNs from old fibroblasts showed a reduction in the epigenetic mark H3K9Me3 and expression of nuclear structural protein Lamin B2, Lap2β and reduction in the heterochromatin protein HP1γ (FIG. 2C). Neonatal iNs also had lower Hoechst (nuclear) intensity and smaller nucleus area compared to aged iNs (FIGS. 2D-2G). These results confirmed that the iNs from aged fibroblasts retained age-related signatures from their parental cells, setting a reference for examining the effects of small molecules on CS in embryonic neurons.

Figure 3:
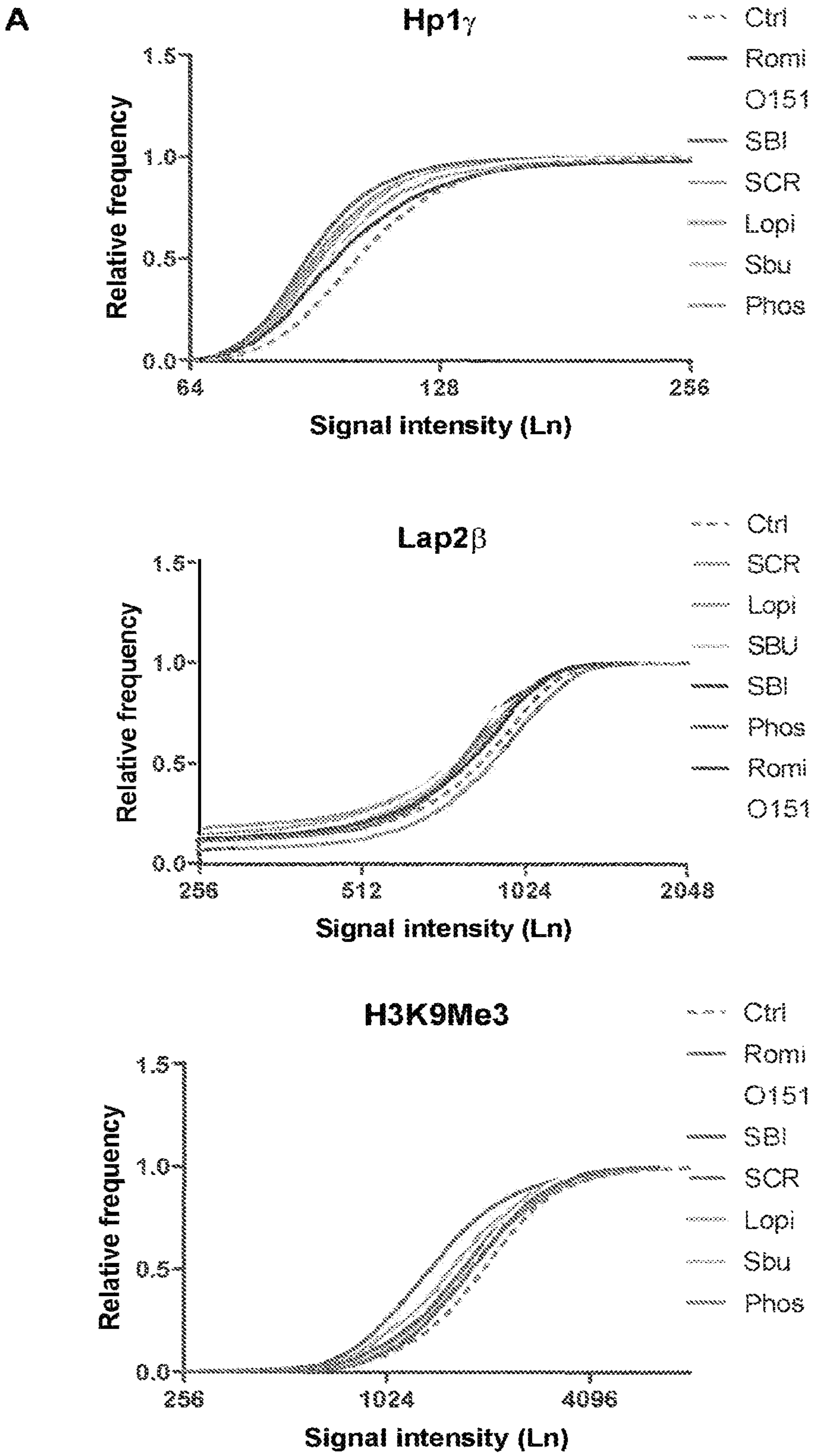
FIGS. 3A-3D demonstrate chemically induced senescence in cortical neurons derived from hESCs. Frequency distribution analysis of high content imaging data for H3k9Me3, Lap2β, and Hp1γ proteins for cortical neurons, dashed red line is control and top seven molecules for each protein showed in the graph (FIG. 3A). Mean difference for signal intensity of all 25 small molecules depicted as mean±95% confidence Intervals compared to the DMSO control cortical neurons. The zero line means no difference compare to the control and if difference in the mean not touching the reference line then changes in expression is significant (FIG. 3B). Confocal images of phospho-Histone H2A.X (Serine 139) in the H9-GFP cortical neurons treated with Etoposide, Actinomycin D and DMSO as control (FIG. 3C). Quantification results for the number of positive foci for phospho-Histone H2A.X (Serine 139) per nuclei in cortical neurons treated with different small molecules (FIG. 3D).
Figure 3:
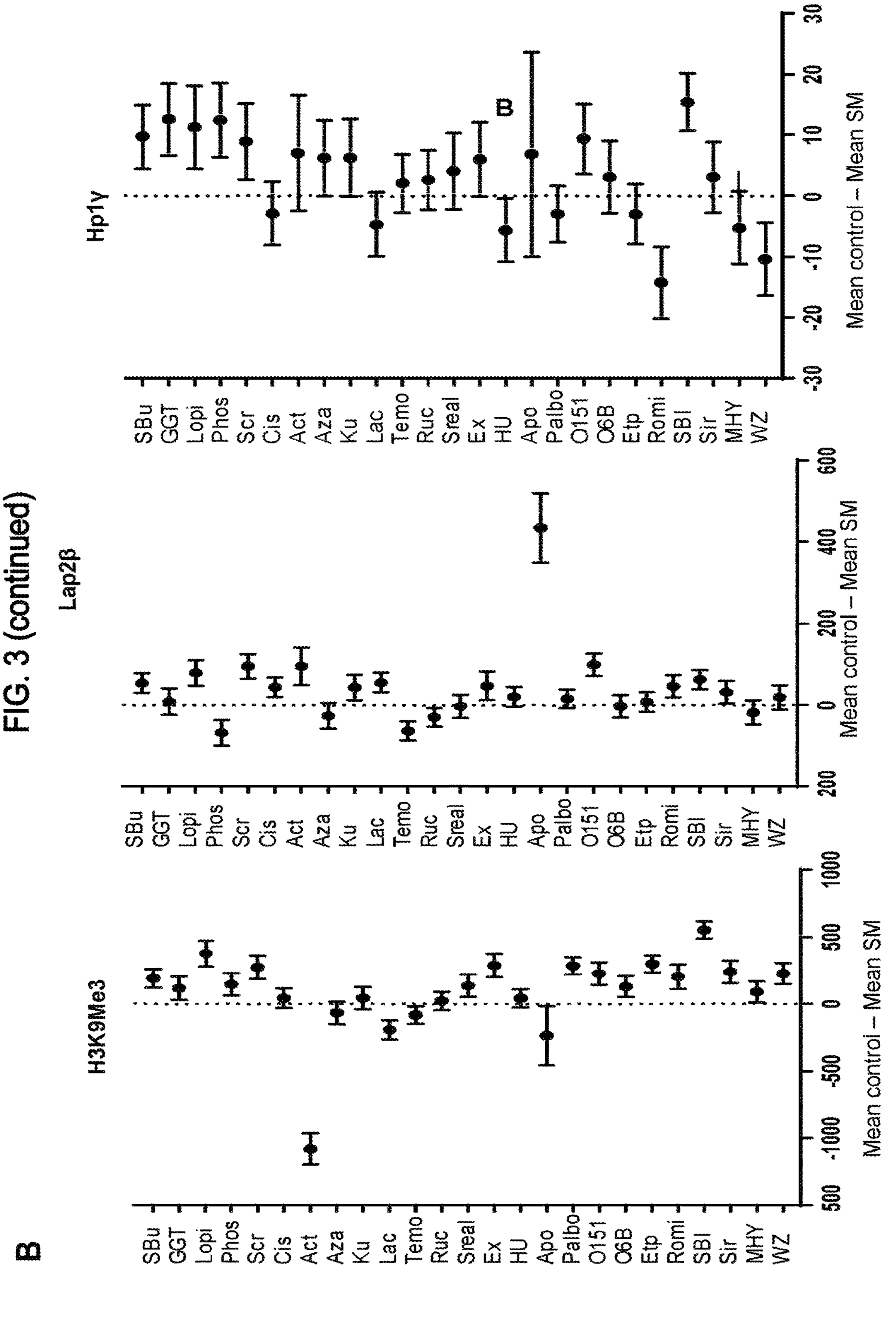
Figure 3:
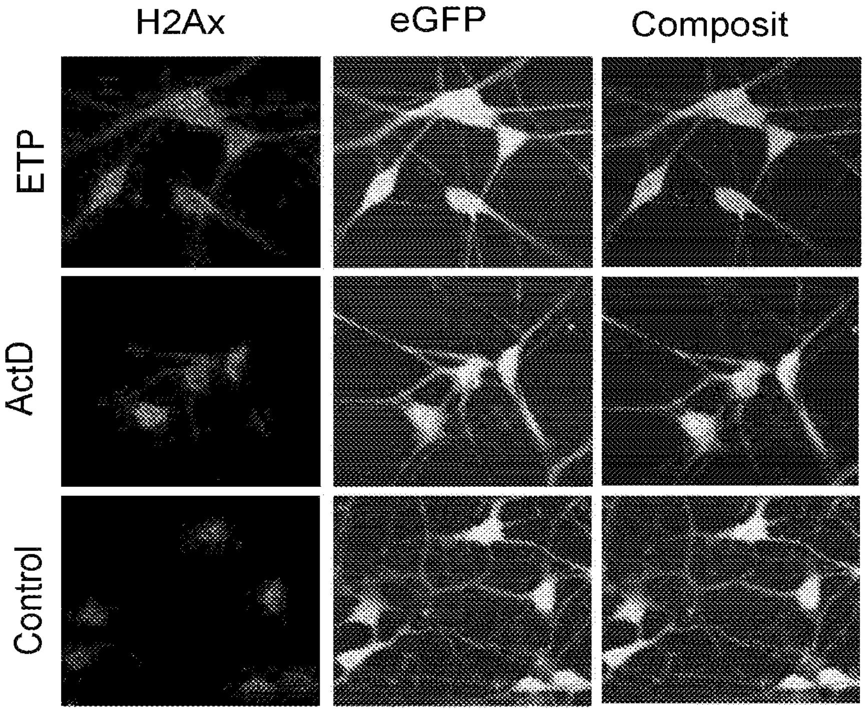
Figure 3:
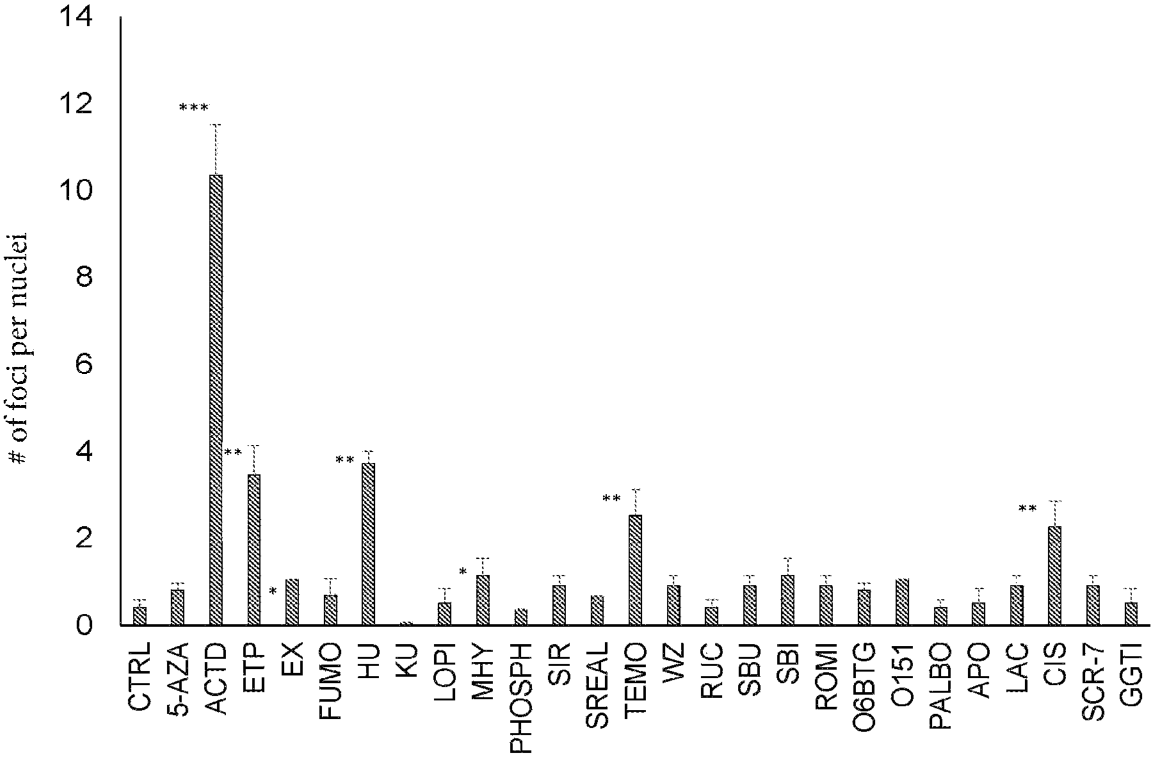
Figure 8:
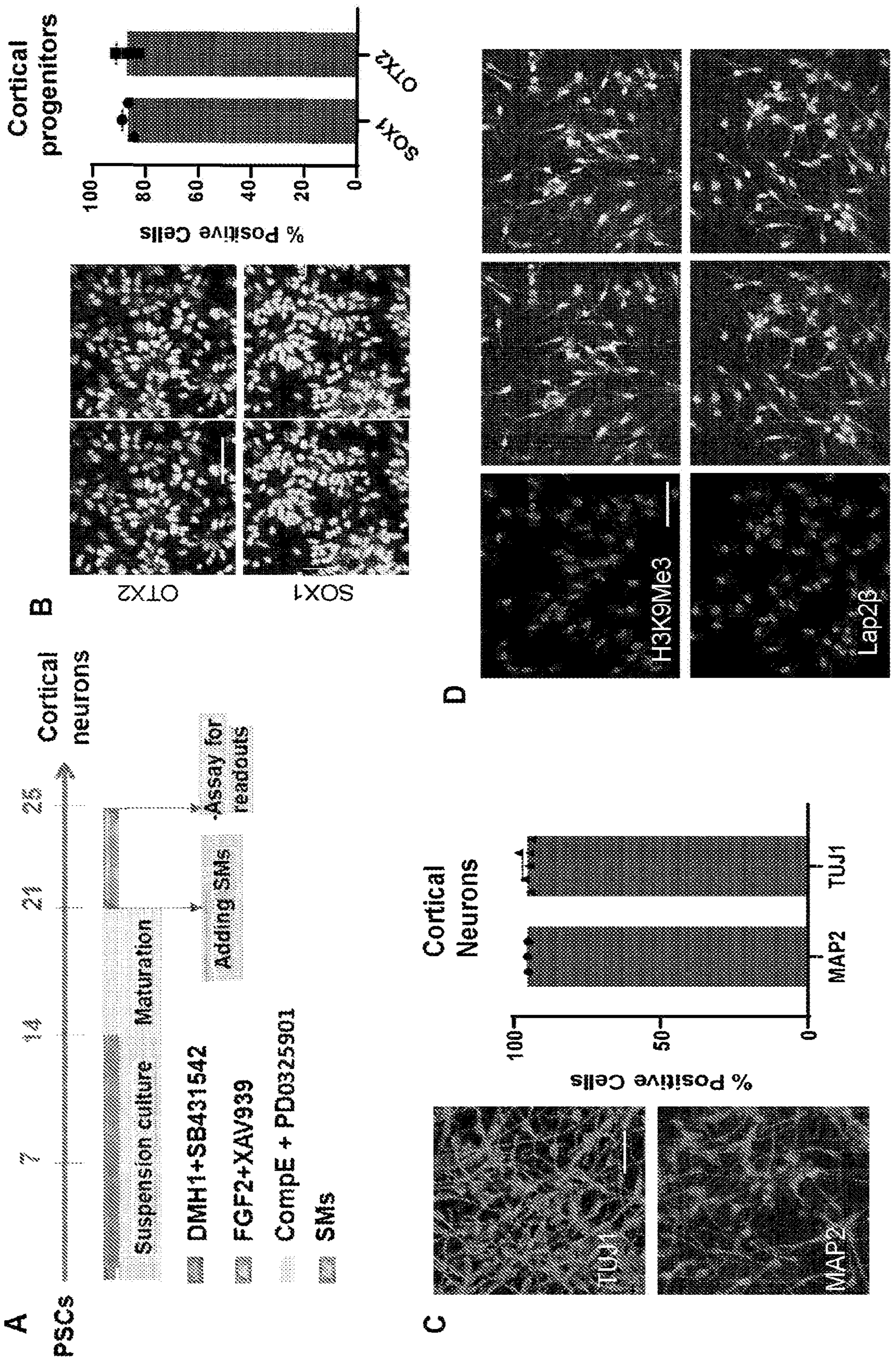
FIGS. 8A-8E (which are related to FIGS. 3A-3D) demonstrate differentiation of cortical neurons from H9-GFP ESCs and characterization for expression of neuronal markers. Differentiation protocol used for generating cortical neurons from H9-GFP stem cells containing molecules and growth factors used for differentiation (FIG. 8A). Immunostaining images for day 14 cortical progenitors expressing SOX1 and OTX2 proteins and quantification for number of positive cells (FIG. 8B). Representative Immunostaining images for day 21 cortical neurons expressing TUJ1 (TUBB3) and MAP2 proteins in red and nucleus stained with Hoechst in blue, and quantification for percentage of positive neurons (FIG. 8C). Immunostaining images for day 21 GFP labeled cortical neurons expressing H3K9Me3 and Lap2β proteins (FIG. 8D). Cell toxicity assay for different doses of 25 small molecules with cortical neurons (FIG. 8E). (ns: not significant, *: $p<0.05$, : $p<0.01$, *:$p<0.001$ one-way ANOVA with Dunnett's multiple comparison test).
Figure 8:
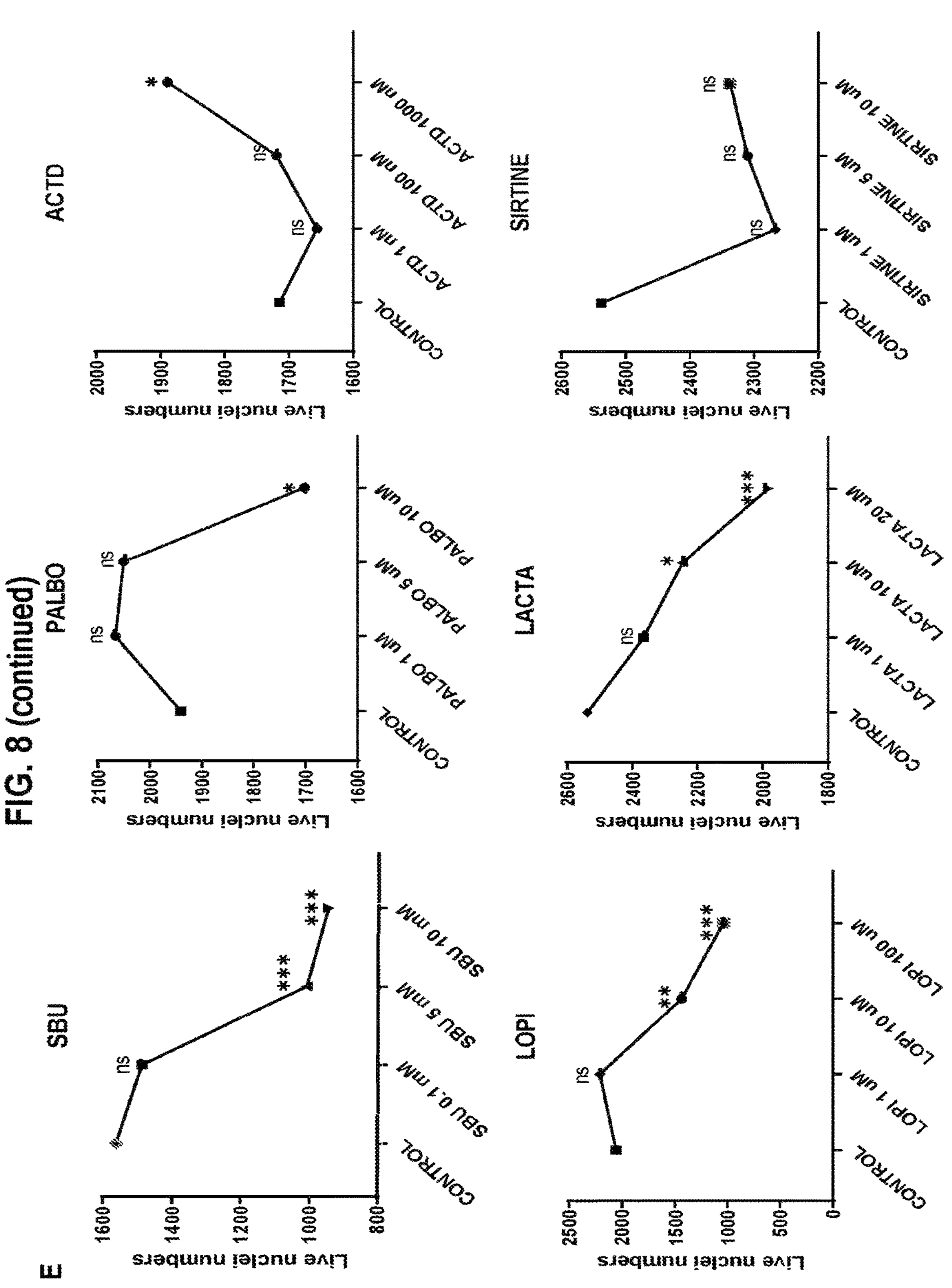
Figure 8:
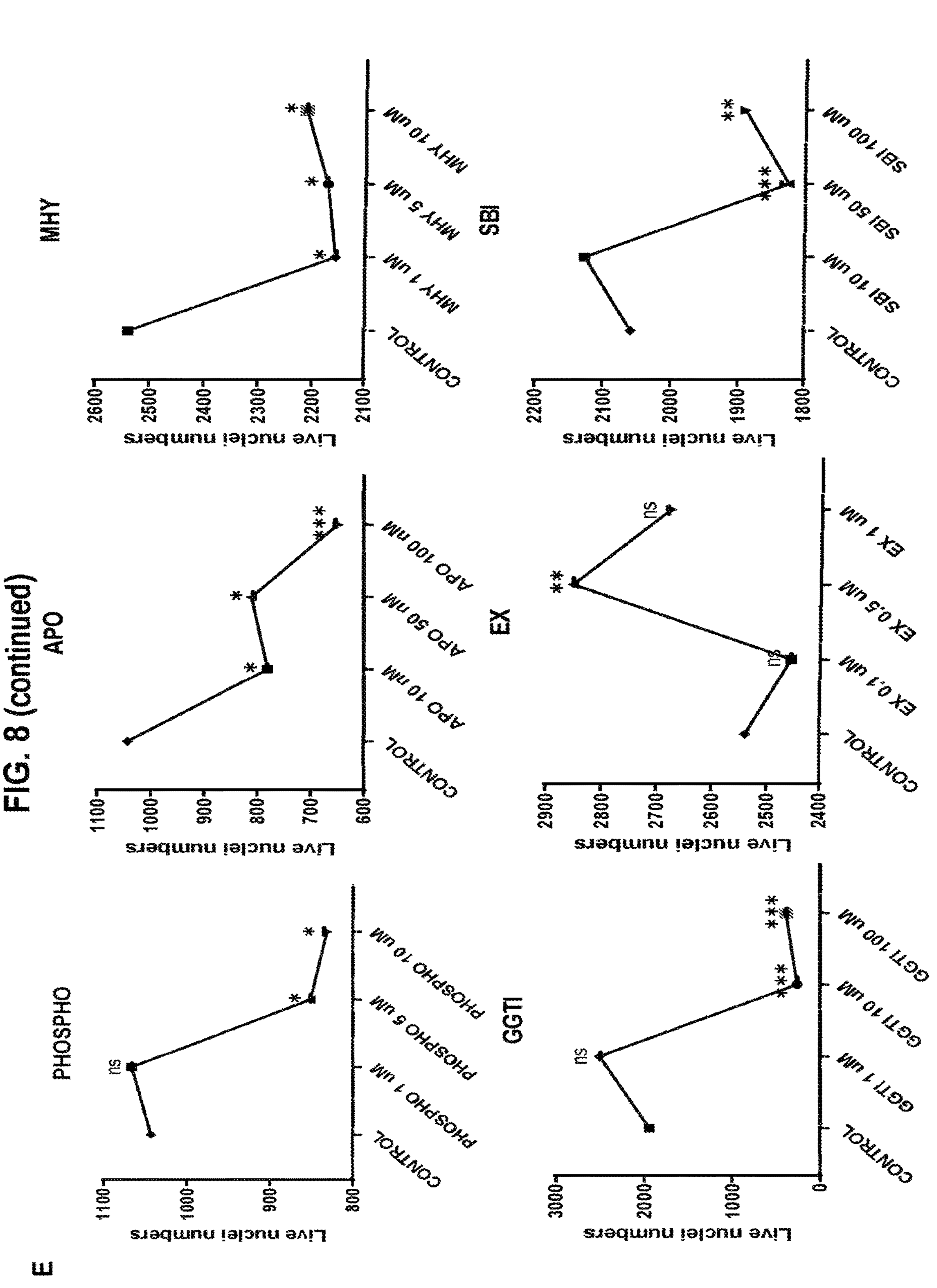
Figure 8:
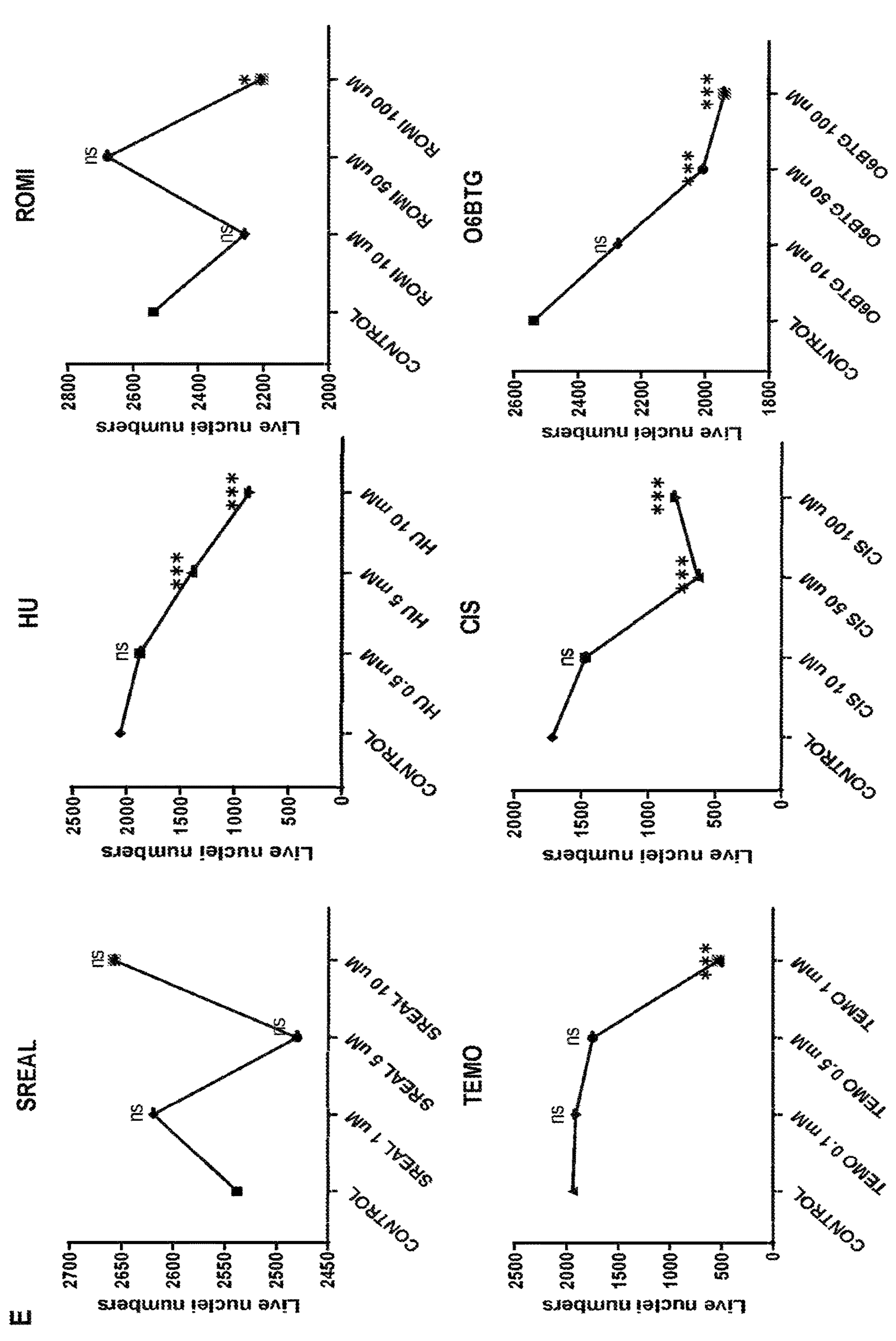
Figure 8:
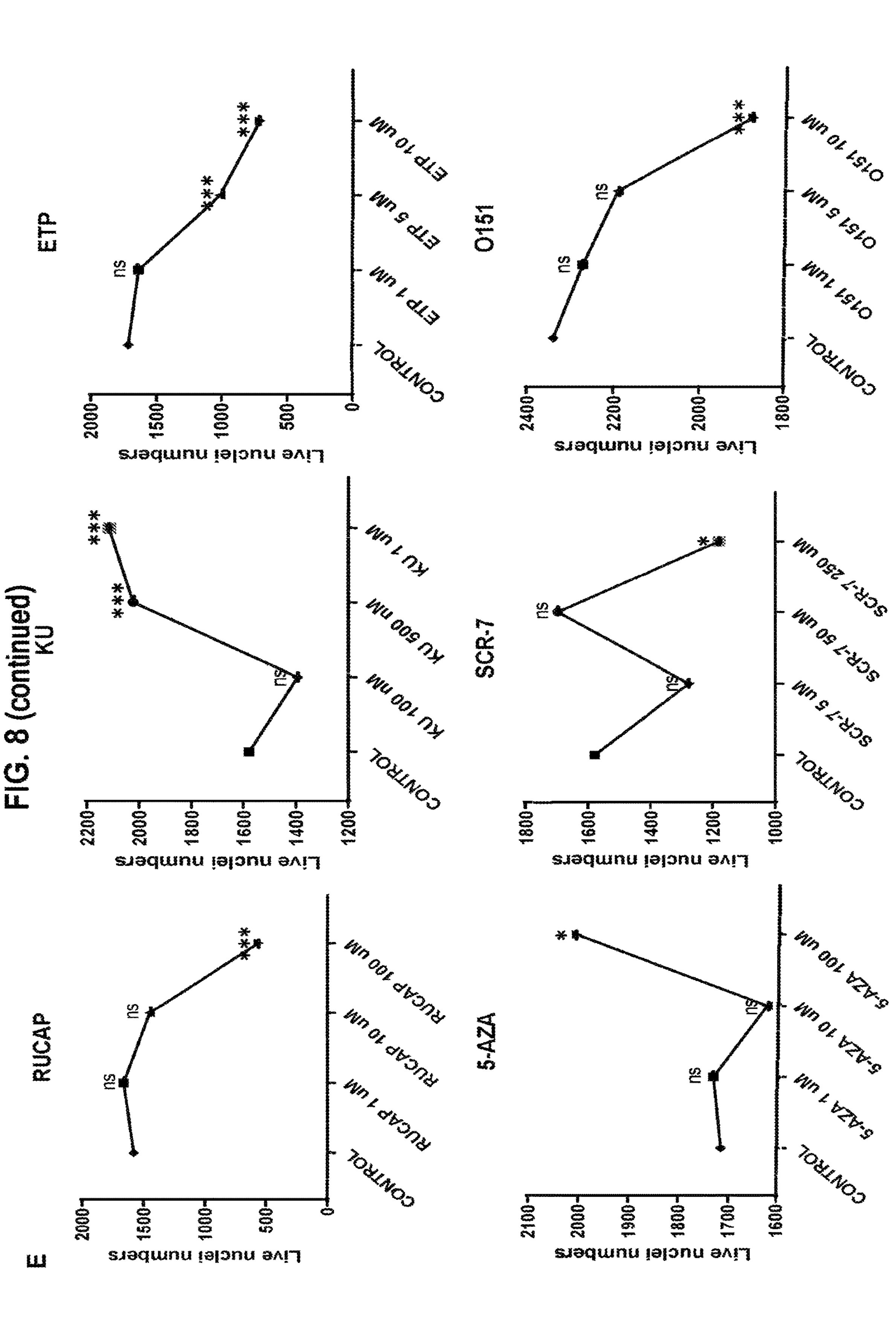
Figure 8:
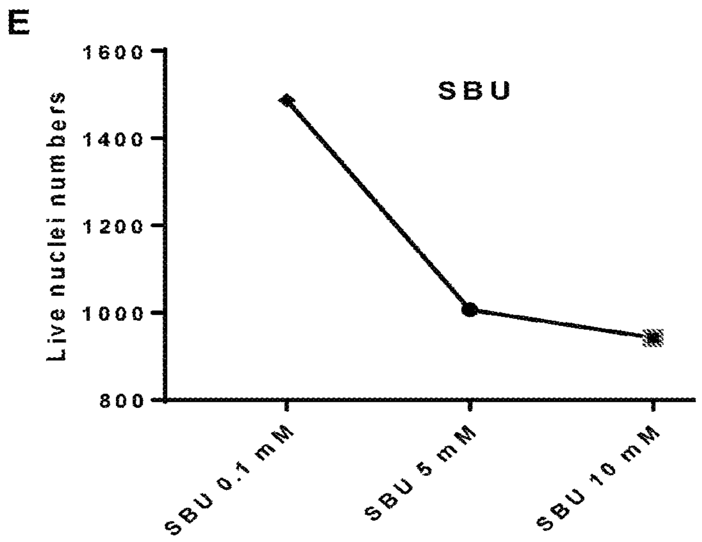
Figure 9:
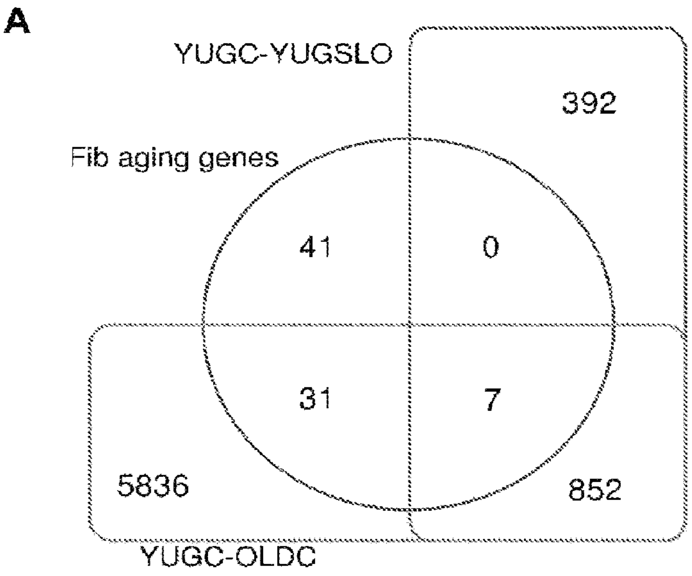
FIGS. 9A-9E (which are related to FIGS. 5A-5F) present RNA-seq data for fibroblast cells treated with SLO and comparison to aged fibroblasts. Venn diagram of transcripts that differentially expressed in SLO treated (YUGSLO) compared to young fibroblasts (YUGC) and aged fibroblasts (OLDC), and their comparison with reported aging genes in the literature (FIG. 9A). Unsupervised multidimensional scaling (MDS) plot of principle components analysis for control and aged fibroblasts (FIG. 9B) and SLO treated samples (FIG. 9C). All DEGs with a p-value <0.05 are selected and tested for over- or under-representation of pathways in the gene list. Any significantly enriched KEGG pathways are ordered from most to least significant and the size of circles related to number of transcripts in that cluster for aged fibroblasts (FIG. 9D) and SLO treated young (Neonatal) fibroblasts (FIG. 9E).
Figure 9:
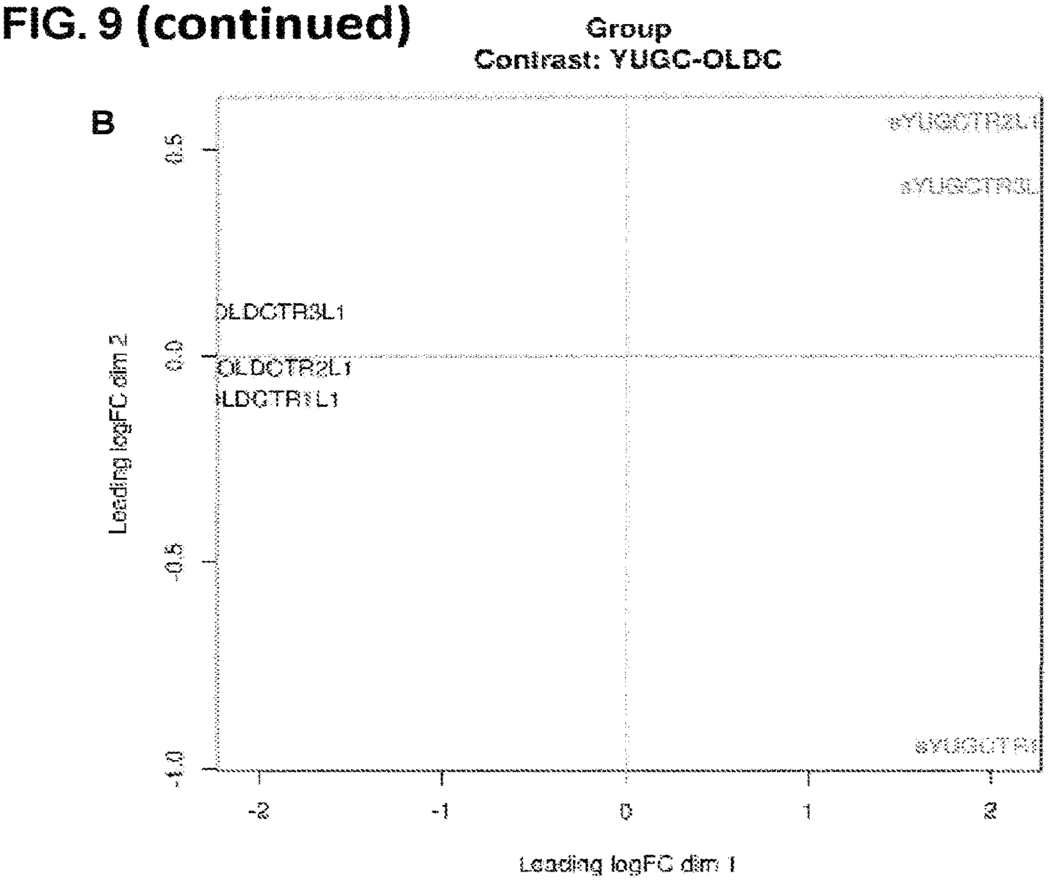
Figure 9:
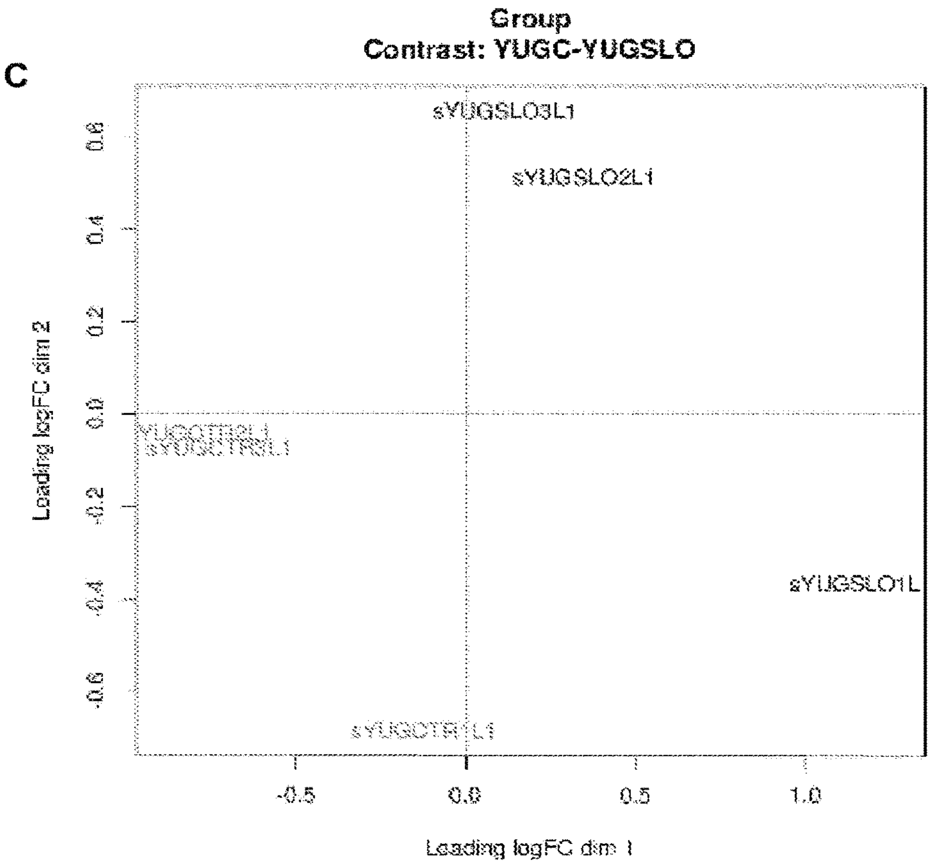
Figure 9:
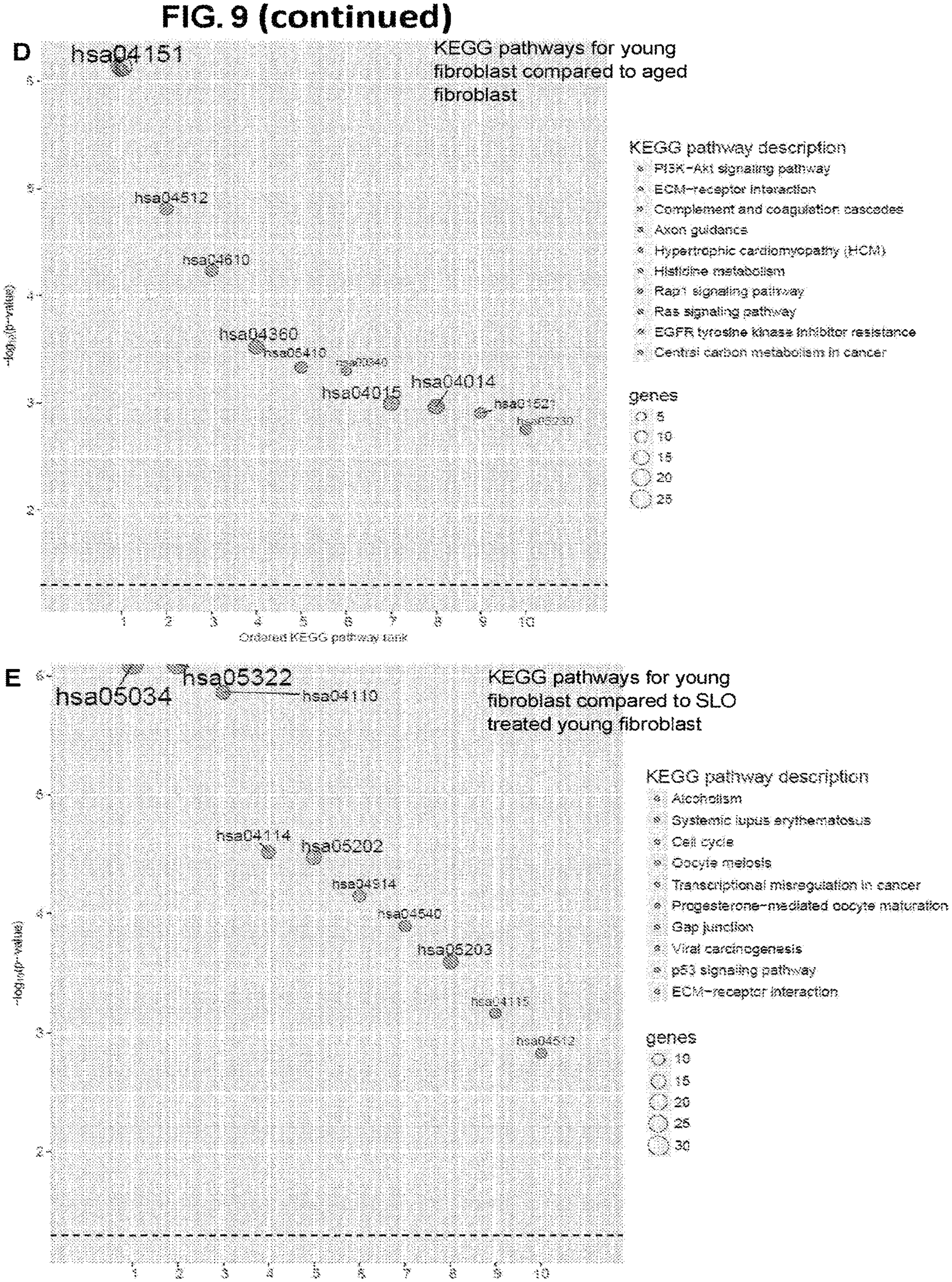

Neurons differentiated from ESCs and iPSCs resembled those during embryonic development. To identify small molecules that induce CS in the embryonic neurons, cerebral cortical neurons from GFP-expressing hESCs (H9, WA09) were generated according to an established protocol (Qi Y et al. *Nat Biotechnol.* 35(2):154-63 (2017)) (FIG. 8). ESC-derived cortical progenitors at day 14 expressed SOX1 (86.7%) and OTX2 (87%), markers of forebrain progenitors. When differentiated to mature neurons in the presence of compound E (that inhibits notch signaling and MEK inhibitor PD0325901 at day 21), the majority of these cells expressed neuronal markers (MAP-2b 95%, TUBB3 95%) (FIG. 8). Neuronal cultures were then treated with these small molecules for 4 consecutive days and assayed for CS hallmarks (FIG. 8). The criteria for positive molecules were expression of CS markers without inducing obvious DNA damage and cell death. By using three different concentrations based on the half maximal inhibitory concentrations ($IC_{50}$s) for each small molecule, a concentration that did not cause cell death (FIG. 9) was identified. Romidepsin, O151, SBI-0206965, Lopinavir, Sodium Butyrate, SCR-7 and Phosphoramidon had a significant impact on the expression of all three readouts H3k9Me3 (Mean±SEM 1980±22, 1957±19, 1632±15, 1806±27, 1990±18, 1908±23, 2037±24, respectively, compared to 2183±14 in control), Lap2β (742±6.4, 688±6, 726±5, 709±8, 734±5, 693±7.7, 855±7.5, , respectively, compared to 789±4 in control) and HP1γ (122±3.6, 98±0.5, 92±0.3, 96±0.64, 98±0.5, 99±0.5, 95±0.5, respectively, compared to 108±0.5 in control) (FIG. 3A, FIG. 11). Romidepsin induced a greater expression of HP1γ and Phosphoramidon induced greater Lap2β expression compared to the mean expression in the control group and were excluded from further experiments (FIG. 11). Among the remaining molecules, neurons treated with Actinomycin D, Etoposide, Temozolomide and Hydroxy-urea showed higher H2A.x expression compared to the control group (FIG. 3B), suggesting these molecules caused significant DNA damage; accordingly, these molecules were excluded from further screenings. Five molecules were selected for further analysis (O151, SBI-0206965, Lopinavir, Sodium Butyrate, SCR-7).

Figure 4:
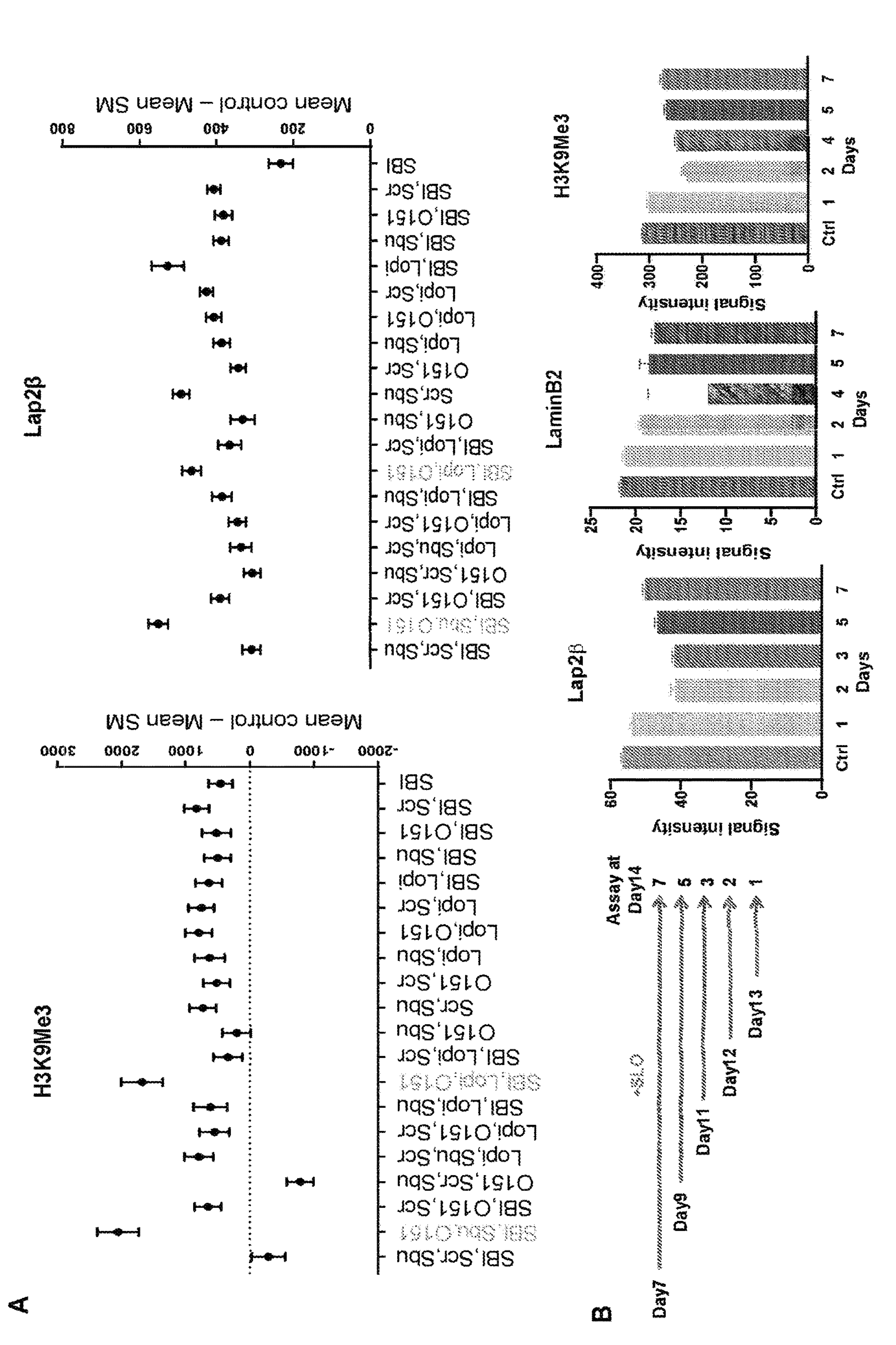
FIGS. 4A-4E demonstrate that combinatorial effects of different synergistically enhanced the senescence phenotype presentation in cortical neurons. Different combination of five most effective molecules (O151, SBI-0206965, Lopinavir, Sodium Butyrate, SCR-7) tested on cortical neurons and mean expression of H3k9Me3 and Lap2β in treatment groups compared to SBI-0206965 (FIG. 4A). Stability test for SLO combination performed by treating neurons for different duration of time and assayed for expression of Lap2β, LaminB2 and H3k9Me3 at day 14 after maturation (FIG. 4B). Relative frequency distribution analysis of different bins of signal intensity for Lap2β, LaminB2 and H3k9Me3 in cortical neurons treated with different small molecules (FIG. 4C). Immunostaining images of H9-GFP cortical neurons treated with MG-132 (proteasome inhibitor), SLO (SBI-0206965, Lopinavir and O151) and SSO (SBI-0206965, Sodium Butyrate and O151) and stained for Lamp2A (Lysosome membrane associated protein) and Proteostat dye for detection of protein aggregation (FIG. 4D), and quantification of images for positive area of neuron for Lamp2A and Proteostat (FIG. 4E). (ns: not significant, *: $p<0.05$, : $p<0.01$, *:$p<0.001$ one-way ANOVA with Dunnett's multiple comparison test).
Figure 4:
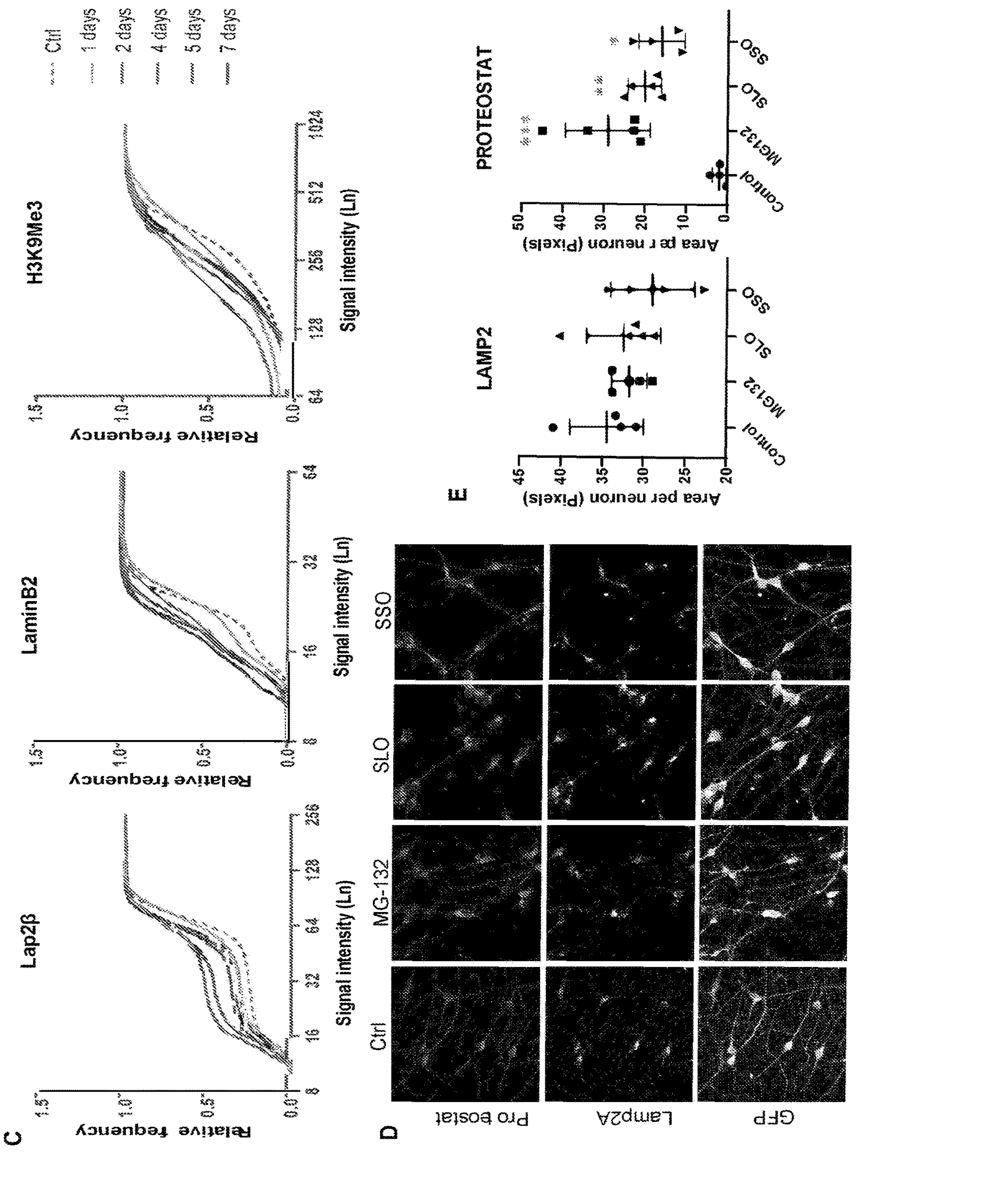

To determine whether any combination of these five small molecules induced CS in neurons, the cells were treated with SBI-0206965 (autophagy inhibitor) alone as a reference because this molecule showed greater performance in modulating all three readouts during initial screenings. In this set of experiments, 50% of the concentration that was used for the first set of experiments for molecules used in pairs and 70% reduction in triple combination to minimize cell toxicity. Results showed that most of the combinations had greater or similar effect as SBI (FIG. 4A). Two of the combinations, SLO (SBI-0206965, Lopinavir, O151) and SSO (SBI-0206965, Sodium Butyrate, O151), had a greater mean difference in H3K9Me3 and Lap2β expression compared with both DMSO (Control) and SBI-0206965 treated cells ($p<0.01$).

TA minimum period of treatment needed to induce stable CS was then determined. Cortical neurons at day 7 were treated with the SLO small molecules for different periods of time (treated at day 7, day 9, day 10, day 12 and day 13) and cells analyzed at day 14. Expression of H3K9Me3, LaminB2 and Lap2β indicated that 2-4 days of continuous treatment with SLO molecules resulted in the maximum effect of the small molecule cocktail (FIGS. 4B, 4C). This experiment showed that expression of H3k9Me3 and Lap2β at 5- and 7-days post treatment recovered slightly but not to normal condition. Reduction in LaminB2 level was more persistent following SLO treatment and stayed at a lower level compared to the control cells even after 5- and 7-days post treatment (FIGS. 4B, 4C).

In addition to the CS phenotypes analyzed above, neuronal senescence is often accompanied by intracellular protein aggregation. The effect of the top two small molecule combinations was examined on protein aggregation with MG-132-treated cells (a proteasome inhibitor) as a positive control. Proteostat™ staining revealed protein aggregates in cells treated with SSO, SLO and MG-132 conditions which were colocalized by Lamp2 positive autophagosomes (Tukey's multiple comparison MG-132 $p<0.0001$, SLO $p<0.004$, SSO $p<0.035$) (shown in FIGS. 4D, 4E).

Figure 5:
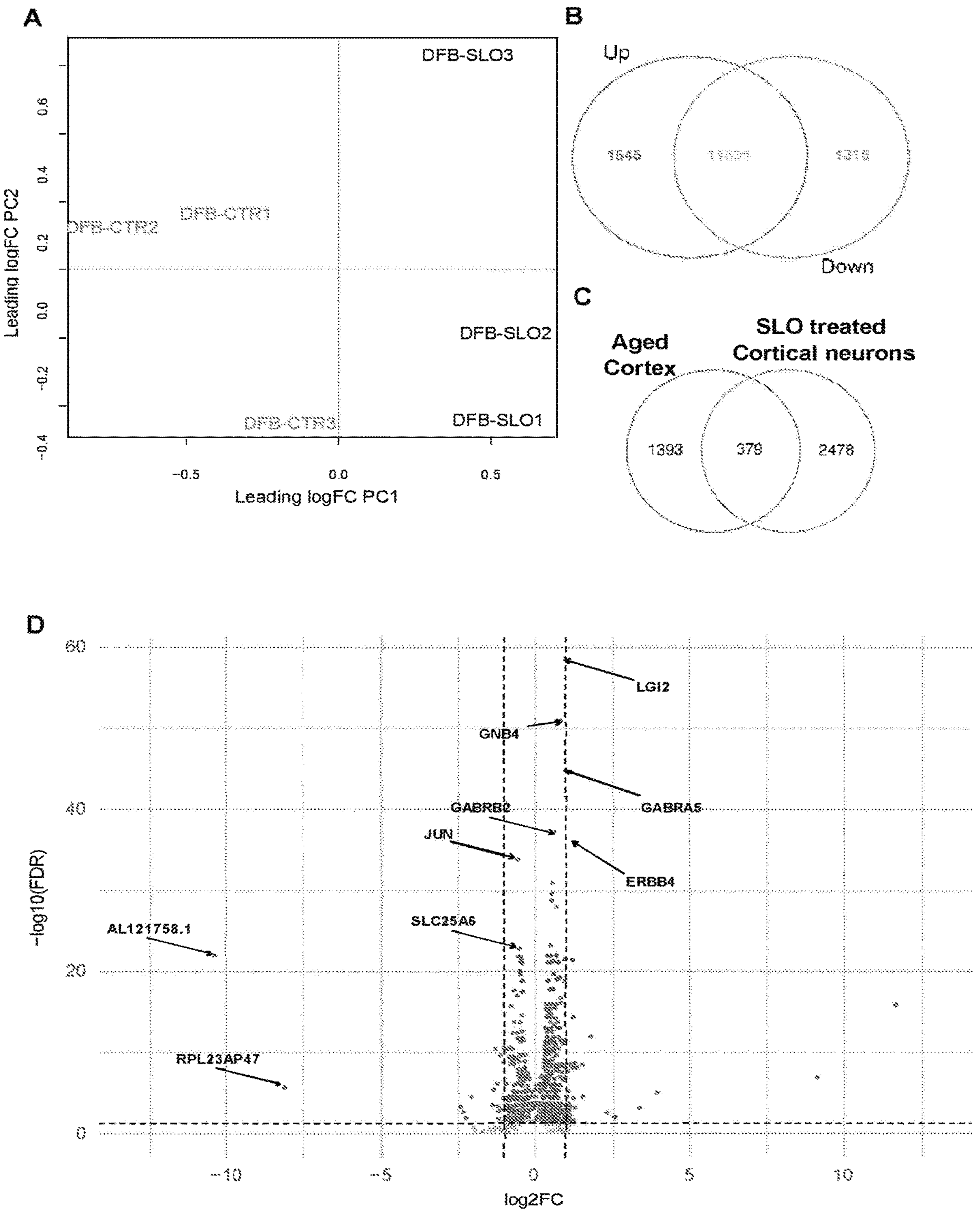
FIGS. 5A-5F. RNA-seq data for SLO treated cortical neurons showed similarities to aged cortex and premature aging pathways. Unsupervised multidimensional scaling (MDS) plot of principle components analysis for control and SLO treated samples (FIG. 5A). Venn diagram for number of transcripts that are differentially expressed in SLO compared to control cortical neurons (FIG. 5B) and comparison of 2860 DEGs in SLO treated cortical neurons with DEGs from aged cortex (compared to young cortex) (FIG. 5C). Smearplot represents each gene with a gray •. Relative to the contrast direction, red • and blue • dots denote up- and down-regulated expression respectively, at an adjusted p-value (FDR) significance threshold of 0.05. The gray dots reflect those genes with no evidence of statistically significant differential expression. The X-axis (log 2 fold change) is the effect size, indicates how much expression has changed with SLO treatment (FIG. 5D). A subset of up to 50 of the most differentially expressed genes with a p-value <0.05 and a log{2}fold-change greater or less than +/−2 are selected. Next, both samples and genes are clustered using Euclidean distances. For genes, an additional elbow function is applied to estimate the number of gene clusters present and colored as red when they are differentially expressed in aged cortex too. Calculated relationships are depicted by dendrograms drawn at the top (samples) and to the left (genes) of the heatmap. The gradation of color is determined by a Z-score that is computed and scaled across rows of genes normalized by TMM. The Z-score of a given expression value is the number of standard-deviations away from the mean of all the expression values for that gene (FIG. 5E). All DEGs with a p-value <0.05 are selected and tested for over- or under-representation of pathways in the gene list. Any significantly enriched WikiPathway pathways are ordered from most to least significant (FIG. 5F).
Figure 5:
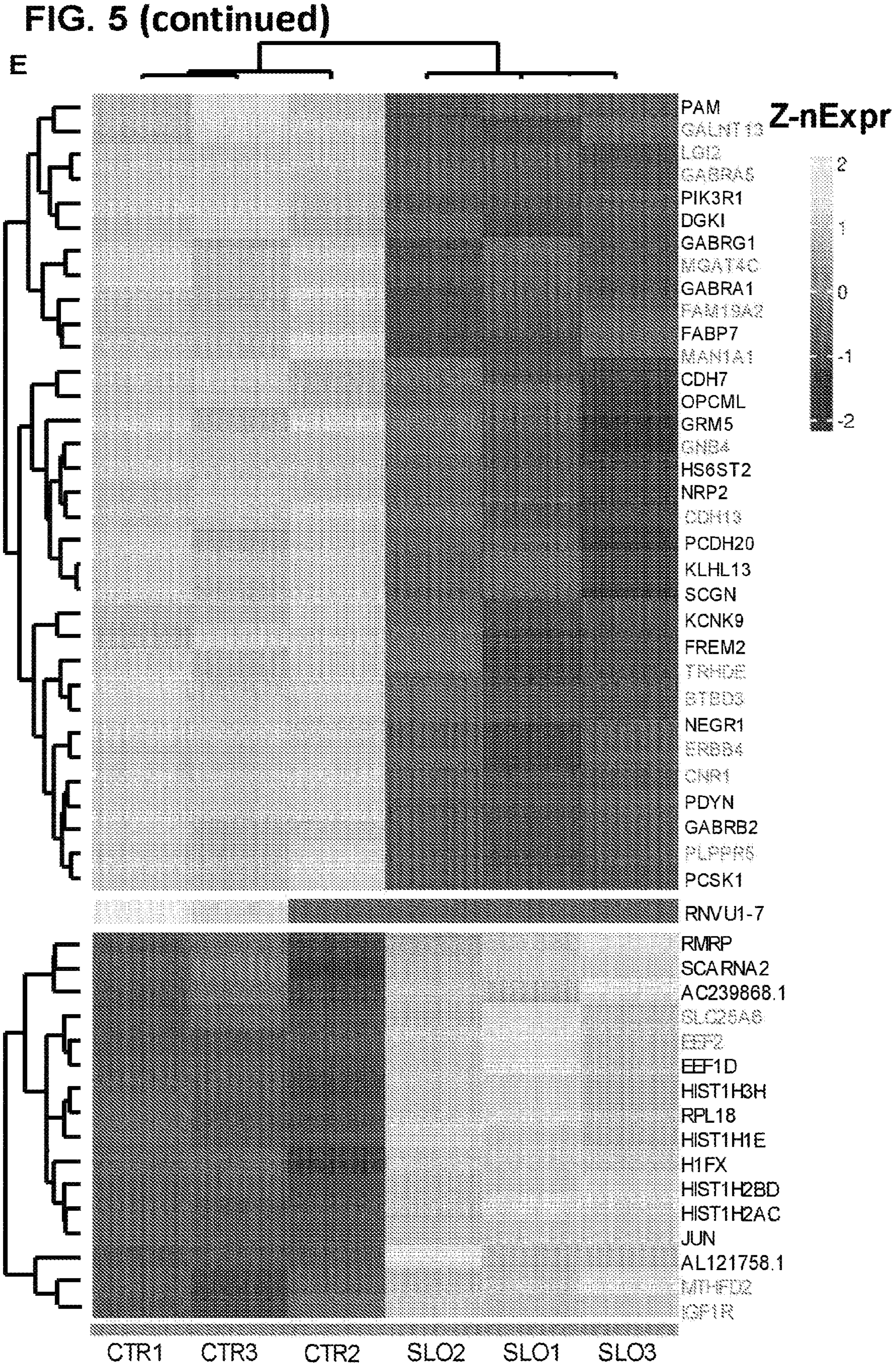

SLO-treated neurons express CS-related transcripts and pathways: To define CS-related changes in SLO-treated neurons, RNA-seq analysis was performed on cortical neurons treated with or without SLO. Principal component analysis based on overall gene expression showed high similarity (clustering) among independently cultured neurons treated with SLO or among those without SLO treatment (controls), but well separated between the SLO-treated and the control groups (FIG. 5A). Comparison between SLO treated neurons and DMSO control neurons resulted in 2860 differentially expressed genes (DEGs) ($FDR<0.05$) with 1315 genes down-regulated and 1545 genes up-regulated upon SLO treatment while 11391 transcripts remained unchanged (FIG. 5B). DEGs were compared from SLO treated cortical neurons with 1772 aging associated genes inferred from brain cortical samples (Chen C Y et al. Proc Natl Acad Sci USA 113(1):206-11 (2016)). Human cortical sample data was derived from comparing 36 young (≤25 years old) to 62 brain samples from aged individuals (≥65 years old). There were 379 of the aging-associated DEGs (22%) that were shared between SLO treated cortical neurons and the aging brain cortical samples (FIG. 5C). These common DEGs included those involved in calcium signaling, GABAergic synapses, neuroactive ligand-receptor interaction, and PI3k/Akt signaling pathways (Table 2, FIG. 5E, highlighted in gray on left). In the DEG list, GABA receptors were also among the most down-regulated genes whereas histone variants were up-regulated (FIGS. 5D, 5E).

Pathway analysis for DEGs in the SLO treated neurons revealed that neurotransmitter receptor signaling and calcium regulation were down-regulated whereas pathways in the protein synthesis and histone modification (especially histone variants) were up-regulated (FIG. 5F).

Premature aging syndromes that are associated with mutations in LMNA gene (which encodes lamin A and lamin C) or WRN gene (WRN RecQ Like Helicase) resemble normal aging in terms of gene expression. Dreesen O et al. Aging (Albany, NY) 3(9):889-95 (2011); Kyng K J et al. *PNAS* 100(21):122259-64 (2003). Over-expression of mutant Lamin A/C (Progerin) in normal neurons caused ageing phenotypes (Miller, 2013). Interestingly, the SLO-treated neurons exhibited an upregulated pathway (WP4320) that shared 12 genes (30% of total genes in the pathway) involved in Hutchinson-Gilford Progeria Syndrome (FIG. 5F). These included MBD3, MTA1, HIST1H3A, H3F3B, HIST1H3J, HIST1H3F, HIST1H3G, HIST1H3H, HIST1H3I, HIST1H3B, HIST2H3D and HIST1H3E, several of which are involved in the histone modification pathway (WP2369). In addition, several members of brain derived neurotrophic factor (BDNF) pathway were both up and downregulated in our RNA-seq data (FIGS. 5E-5F). Up-regulated BDNF responsive transcripts in SLO-treat cells included insulin receptor substrate 1 and 2 (IRS1 and IRS2), pro-apoptotic genes (FOXO3, BAD and BCL2L11), nutrients sensing transcripts (EIF4EBP1, TSC2, EEF2) and downstream kinase molecules (PIK3R2, ELK1, PTPRF, MAPK7, AKT1, MAP2K2, PLCG1, CRTC1 and JUN) and other transcripts (SHC2, RAB3A, DOCK3, RELA, NCK2, RACK1, SH2B1, LINGO1, STAT5B, EGR1, SQSTM1). BDNF pathway associated transcripts that were down regulated in SLO treated cells included AMPA and NMDA receptors (GRIA1, GRIA2, GRIA3, GRIN2B), both trkB and trkC receptors (NTRK2, NTRK3) and their downstream calcium signaling molecules (NFATC4, CAMK2A, CAMK4), MAPK responsive transcripts (MAP2K1, KIDINS220, PRKAA2, PPP2CA) and other transcripts (GABRB3, MEF2C, SHC3, RASGRF1, PIK3R1, CDC42, CDH2, CNR1, SPP1, EIF4E, NSF, PTPN11, DLG1, APC). The transcriptome data further suggested that the SLO-treated neurons resemble those from aged human cortex.

Figure 10:
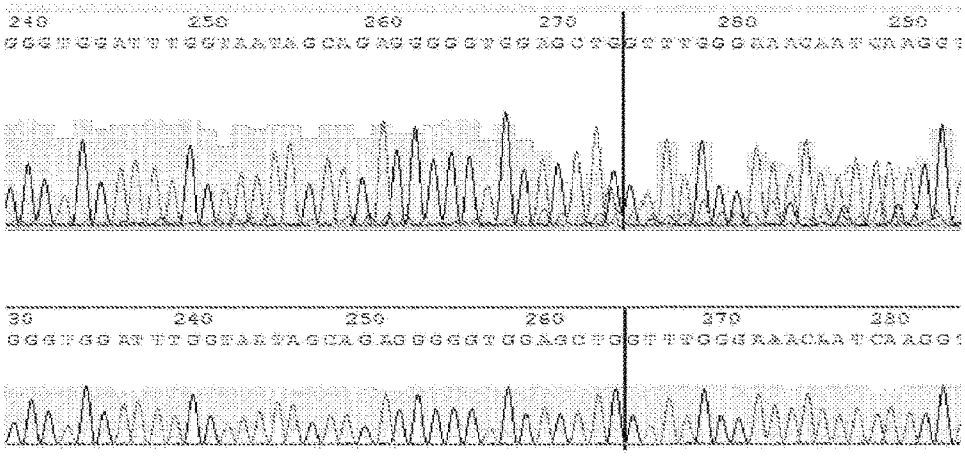
FIGS. 10A-10C (which are related to FIGS. 6A-6H) demonstrate characterization of TDP43 G298S (SEQ ID NO: 1) and TDP43 G298G (SEQ ID NO: 2) iPSCs. Sanger sequencing result for both mutant (FIG. 10A top panel) and corrected (A lower panel) (isogenic control) cell lines. STR analysis for both cell lines were done for selected loci depicted in FIG. 10B, and karyotype analysis for mutant (left) and corrected (right) cell lines (FIG. 10C).
Figure 10:
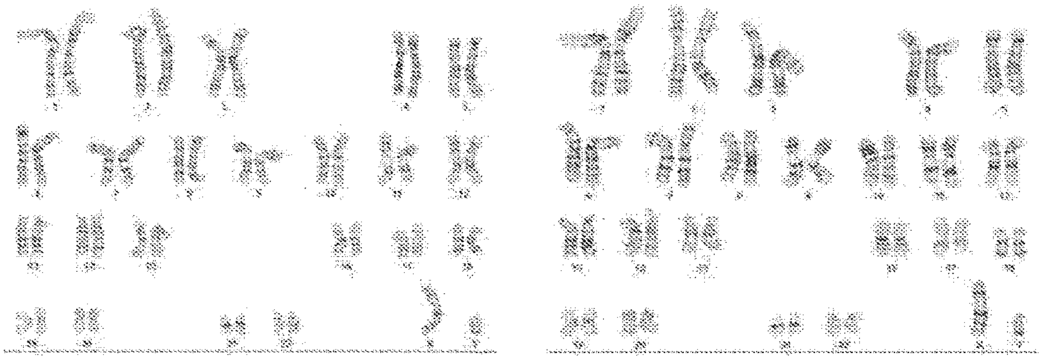

Induction of CS accelerates disease phenotype manifestation in ALS MNs: Neurodegenerative diseases such as amyotrophic lateral sclerosis (ALS) usually manifest symptoms after the fifth decade of life. Induction of CS in ALS iPSC-derived neurons could accelerate the presentation of disease phenotypes, and ALS MNs could respond differently to CS factors and present more changes in senescence read outs. The TARDBP mutant (G298S) iPSC line generated from an ALS patient and its isogenic cell line (G298G) produced by correcting the mutation using CRISPR (FIG. 10) was used to make this determination. Both mutant and corrected iPSCs were differentiated to spinal motor-neurons (MNs) using a protocol disclosed in Chen H et al. *Cell Stem Cell* 14(6):796-809 (2014) and Du Z W et al. *Nat Commun.* 6:6626 (2015) (FIG. 6A) and MNs were treated with the SLO cocktail at day 28 (7 days after maturation) for 4 days. As expected, addition of the small molecules did not significantly alter the percentage of cells expressing cleaved caspase 3 (CC3), even 4 weeks after the removal of the cocktail (control=12±3.3, SLO=10±1.5, SSO=10.7±2.4, MG132=16.4±3.7) (FIG. 6B), suggesting no obvious cytotoxicity.

Figure 6:
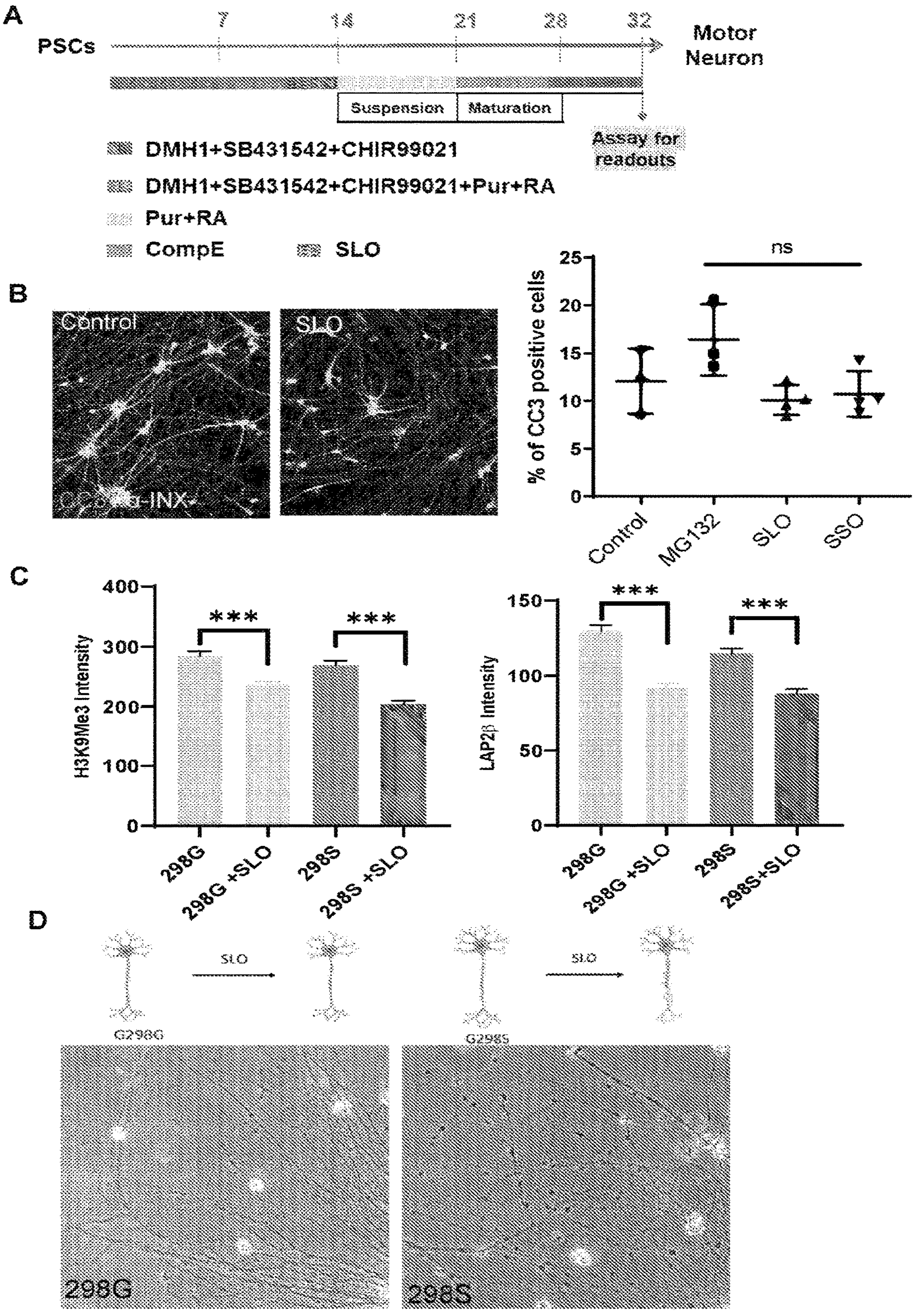
FIGS. 6A-6G demonstrate that Motor-neurons (MNs) derived from TARDBP mutant iPSCs treated with SLO displayed disease phenotype presentation. Differentiation protocol used for generating MNs from TDP-43 G298S mutant and G298G isogenic iPSCs containing molecules used for differentiation (FIG. 6A). Immunostaining for cleaved caspase 3 and alpha internexin proteins in cultured MNs treated with SLO, SSO and MG-132, 32 days post induction (FIG. 6B). Expression result of high content imaging for H3K9M3 and LAP2β in both TDP43 G298G isogenic control and G298S mutant following SLO treatment (Mean of SLO treatment compared to the control group with DMSO) (FIG. 6C). Representative phase contrast image of MN culture from both control and mutant ALS neurons treated with SLO (FIG. 6D). Immunostaining images for alpha Internexin, Proteostat, phosphorylated neurofilament heavy proteins in control MNs and mutant MNs treated with SLO, right panel shows higher magnification merged images of control and mutant MNs treated with SLO (FIG. 6E), and quantification result for phosphorylated neurofilament heavy positive aggregated (FIG. 6F) and Proteostat positive protein aggregations (G) across all groups (FIG. 6G). (ns: not significant, *: $p<0.05$, : $p<0.01$, *:$p<0.001$ one-way ANOVA with Dunnett's multiple comparison test).
Figure 6:
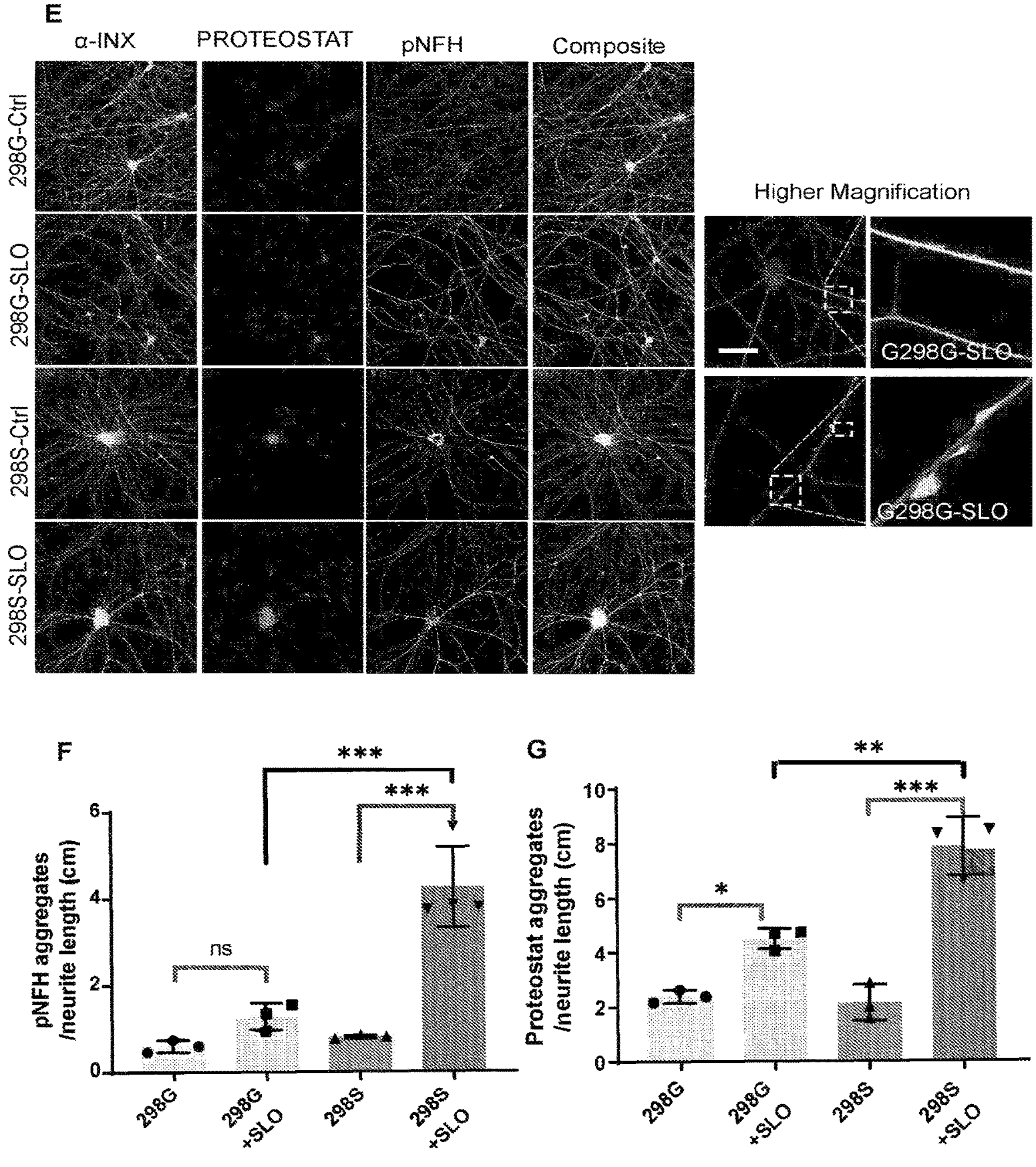

It was then determined whether MNs treated with SLO displayed CS-like phenotypes as was observed in fibroblasts and cortical neurons. Both 298G and 298S MNs showed a reduction in the expression of H3K9Me9 and Lap2β following SLO treatment (FIG. 6C), indicating that SLO treatment induces CS. Both cell lines responded at the same level to the SLO chemicals and difference in H3K9Me3 and lap2p signal intensity was not significant (FIG. 6C). Whether induction of CS accelerated neuronal degeneration was then determined. By day 32, the 298S MNs treated with SLO showed axonal swellings, a sign of axonal degeneration whereas 298G MNs showed relatively intact neurites (FIG. 6D). Proteostat staining was increased in SLO-treated cells, especially in the 298S MNs. Staining for phosphorylated neurofilament (which is a marker for axonal degeneration and turnover) was significantly increased in the SLO-treated 298S than in non-SLO-treated 298S and SLO-treated 298G MNs. Under higher magnification Proteostat-positive aggregates were observed along the axons and were positive for both α-Internexin and phosphorylated neurofilament (FIG. 6E). Quantification of the aggregates showed a significant increase in p-NFH aggregates (1.22±0.31 in G298G compare to 4.26±0.92 in G298S) and Proteostat-positive aggregates (4.49±0.38 in G298G compare to 7.86±1.06 in G298S) in G298S ALS mutant MNs than the G298G isogenic control MNs that were treated with SLO (FIGS. 6F, 6G).

The neurofilament imbalance in SOD1 mutation is one of ALS disease manifestations (3). RT-PCR analysis indicated that three of neurofilament transcripts, including NEFH, NEFM, and alpha-Internexin had less expression in mutant neurons and only NEFL gene had greater expression compared to the isogenic control. When treated with SLO, a reduction in gene expression for all neurofilaments was observed regardless of their genotype, but neurofilaments still had higher expression in the normal genotype except the NEFL. These results confirmed misregulation of neurofilaments in TARDBP mutant MNs. Thus, induction of CS facilitates the presentation of ALS related disease phenotypes.

Significance

Most neurodegenerative diseases are concurrent with aging. Hence, recapitulating CS in stem cell-derived neurons could increase the ability to study disease mechanisms. By using H3K9Me3, HP1γ and Lap2β as readouts and screening for chemicals/pathways that induce CS in neonatal fibroblasts and iPSC derived cortical neurons, cocktails of small molecules that induce CS in the forebrain neurons were developed. This chemical induced senescence (CIS) was validated in motor neurons derived from ALS patient iPSCs. Importantly, CIS enhanced the presentation of disease related phenotypes. This CIS strategy enabled more effective iPSC-based modeling of age-related degenerative diseases.

The in vitro neuronal senescence system, despite the lack of many other cell types that are normally present in the human brain, resembles the aging cortex samples. This is reflected by the substantial overlap of age-related transcripts (22%) between CIS neurons produced as disclosed herein and aged human brain tissues. Chen C Y et al. *PNAS* 113(1):206-11 (2016). These common transcripts are involved in neurexin/neuroligin complexes at synaptic membrane assembly and neurotransmitter release related transcripts from GABA, glutamate and cholinergic systems. Neurexin expression is known to decline with age. Kumar D and Thakur M K, *Age* (Dordr). 37(2):17 (2015); Konar A et al. *Aging Dis.* 7(2):121-9 (2016). Other transcripts like CRTC1 transcription coactivator of CREB1 (Paramanik V and Thakur M K, Arch Ital Biol. 151(1):33-42 (2013)) and BDNF signaling pathway, which show significant changes in our SLO-treated cortical neurons, also contribute to brain aging and neuronal senescence (Boger H A et al. *Genes Brain Behav.* 10(2):186-98 (2011); Silhol M et al. *Neuroscience.* 132(3):613-24 (2005); Tong C W et al. *Dongwuzue Yanjiu* 36(1):48-53 (2015); von Bohlen und Halbach O, *Front* Aging Neurosci. 2 (2010)). Some of molecules that we described as a member of BDNF pathway like as p62 (SQSTM1) has multiple function and well known for its contribution in neurodegeneration (Ma S, et al. *ACS Chem Neurosci.* 10(5):2094-114 (2019)). In addition, CIS neurons produced as disclosed herein shared several histone variants with the progerin effect in the progeria syndrome. Histone variants are one the most affected transcripts during CIS in the cortical neurons. Histone variants exchange, by regulating expression of age related genes (Gevry N et al. *Genes Dev.* 21(15):1869-81 (2007)) and/or chromatin organization (Flex E et al. *Am J Hum Genet.* (2019)), is one of the mechanisms behind CS and ageing. Thus, CIS produced as disclosed herein recapitulated some parts of progerin effects mostly at epigenetic level.

Cellular senescence shares features like mitochondrial dysfunction, DNA damage, and alteration in P16 expression and epigenetic marks for gene silencing (Kim Y et al. *Cell Rep.* 23(9):2250-8 (2018); Madabhushi R et al. *Neuron.* 83(2):266-82 (2014); Rubinsztein D C et al. *Cell* 146(5):682-95 (2011); Satoh A et al. *Nat Rev Neurosci.* 18(6):362-74 (2017)). These alterations ultimately result in age-related changes at the cellular level, including changes in cell size, shape and metabolism, proliferation arrest, and telomere erosion (Petrova N V et al. *Aging Cell* 15(6):999-1017 (2016); Lopez-Otin C et al. *Cell.* 153(6):1194-217 (2013); Hernandez-Segura A et al. *Trends Cell Biol.* 28(6):436-53 (2018)). In mitotic cells like fibroblasts, expression of P16 accompanies proliferation arrest and induces senescence. P16 activation by Palbociclib as disclosed herein was one of the most efficient pathways in CS by blocking CDK4/6 and proliferation of fibroblasts, resulting in senescence (Vijayaraghavan S et al. *Target Oncol.* 13(1):21-38 (2018)). Other pathways implicated in observations with fibroblasts were related to the DNA repair, DNA synthesis and DNA alkylation pathways that are all related to cell division and telomere attrition. Surprisingly none of the sirtuin inhibitors induced senescence in fibroblasts or neurons despite their effects on aging. Satoh A et al. *Nat Rev Neurosci.* 18(6):362-74 (2017); Bonda D J et al. *Lancet Neurol.* 10(3):275-9 (2011); Mazucanti C H et al. *Curr Top Med Chem.* 15(21):2116-38 (2015). This can reflect differences between cell types or insufficient treatment with inhibitors.

In post mitotic cells like neurons, protein quality control, including proteasome and autophagy process, is more important in CS progression. Ihara Y et al. Cold Spring Harb Perspect Med. 2(8) (2012); Scotter E L et al. *J Cell Sci.* 127(6):1263-78 (2014); Pan T et al. *Brain* 131(8):1969-78 (2008); Zhang Y et al. *Rev Neurosci.* 28(8):861-8 (2017). This is reflected herein by showing the powerful CS-inducing effect of autophagy inhibitors. Faulty autophagosomes could not clear impaired mitochondria and unfolded protein debris, leading to lack of mitochondrial turnover and producing more oxidative stress. He L Q et al. *Acta Pharmacol Sin.* 34(5):605-11 (2013); Wyss-Coray T, *Nature* 539(7628):180-6 (2016). Oxidative stress generates ROS and accounts for higher DNA mutations, which is ultimately related to C S. Lo Sardo V. et al. *Nat Biotechnol.* 35(1):69-74 (2017); Campos P B et al. *Front Aging Neurosci.* 6:292 (2014). Similarly, inhibition of DNA glycosylase (OGG1), important in detecting and removing oxidized nucleotides in genomic DNA, was found to exacerbate CS phenotype in neurons but not in fibroblasts. Two of three small molecules in SLO, DNA glycosylase (OGG1) inhibitor (O151) and HIV protease inhibitor (Lopinavir), modulated CS phenotypes in neurons, indicating that base excision repair (BER) pathway (Leandro G S et al. *Mutat Res.* 776:31-9 (2015); Cannard S et al. Cold Spring Harb Perspect Med. 5(10) (2015); Sykora P et al. *Mech Ageing Dev.* 134(10):440-8 (2013)) and proteasome activity are critical pathways for the health of neurons (Bedford L et al. *J Neurosci.* 28(33):8189-98 (2008); Dantuma N P and Bott L C, *Front Mol Neurosci.* 7:70 (2014); van Tijn P et al. *J Cell Sci.* 120 (9):1615-23 (2007); Zheng C et al. *Neurodegener Dis.* 14(4):161-75 (2014)).

One advantage of developing CIS is to enable effective and reliable modeling of age-related diseases using human stem cells. Some aspects of neurodegenerative changes such as ALS can be recapitulated by strictly controlling the neuronal differentiation process, prolonged maturation, and undergoing stress (including culturing under a basal condition without trophic factors and medium changes). Chen H et al. *Cell Stem Cell.* 14(6):796-809 (2014). Such manipulations over a long term adds variables to the system, making stem cell-based disease modeling more difficult. MNs from patients with TARDBP mutations have increased levels of soluble and detergent-resistant TDP-43 and show decreased cell survival, suggesting that this model is representative of ALS pathology (Bilican B et al. *PNAS* 109(15):5803-8 (2012); Fujimori K et al. *Nat Med.* 24 (10):1579-89 (2018)). However, neither increase in insoluble TDP43 nor its mislocalization phenotypes were repeated in a most recent study (Klim J R et al. *Nat Neurosci.* 22(2):167-79 (2019)). Similarly, dopamine neurons from Parkinson' disease (PD) iPSCs exhibited mitochondrial dysfunction and oxidative stress, changes in neurite growth and morphology, synaptic connectivity and lysosomal dysfunction (Sanchez-Danes A et al. EMBO Mol Med. 4(5):380-95 (2012); Reinhardt P et al. *Cell Stem Cell* 12(3):354-67 (2013); Monzio Compagnoni G et al. Stem Cell Reports 11(5):1185-98 (2018); Kouroupi G et al. PNAS 114(18):E3679-E88 (2017)), but hallmark pathology like protein aggregation and Lewis body are rarely observed (Sanchez-Danes, 2012; Reinhardt, 2013; Monzio Compagnoni, 2018; Kouroupi, 2017; Mishima T et al. *Int J Mol Sci.* 19(12) (2018)). These inconsistencies can be due to the different protocols used and the long-term cultures that are necessary to mature the stem cell derived neurons. The methods set forth herein for producing CIS enabled early and consistent presentation of disease relevant phenotypes, including protein aggregation and axonal degeneration in TDP43 mutant MNs. Since these cocktails induce CS in different neuronal types, using CIS as produced using the methods and cell culture components set forth herein can be used to promote phenotypic presentation in other age related diseases using iPSCs, such as PD, AD, and age related macular degeneration.

The CIS method set forth herein induces CS in a short period (after 2-4 days of treatment) without a need of genetic manipulation. It promoted reliable and consistent presentation of disease relevant phenotypes and was not specific to any particular disease. The cocktails were developed by screening a relatively small pool of molecules, suggesting that other molecules, especially those affecting similar pathways, can also induce CS. The methods also enabled faster and consistent presentation of disease phenotypes from iPSC-derived neurons. It is thus useful for establishing drug testing platforms.

Methods

Neuronal differentiation from hPSCs: Human embryonic stem cells H9 (WA09, WiCell), H9-GFP (AAVS1-CAG-eGFP) cells and TARDBP mutant (G298S) and isogenic control induced pluripotent stem cells (iPSCs) were grown on Matrigel with Essential-8 medium (Stemcell Technologies) to 25% confluency. For cortical differentiation, the fifth day cultures of hPSCs were treated with Accutase and the dissociated single cells were cultured in the neural differentiation medium (NDM) (DMDM/F12:Neurobasal 1:1+1× N2 Supplement+1 mM L-Glutamax) with the SMAD inhibitors SB431542 (Stemgent), DMH-1 (Tocris) (both at 2 μM) and Rho kinase inhibitor (Tocris) (overnight) in 25-cm flasks to promote sphere formation over seven days. On day 8, the spheres were patterned to dorsal forebrain (cerebral cortical) progenitors with the smoothened antagonist cyclopamine (Stemgent, 2 μM) and FGF2 (R&D, 10 ng/ml) for seven days. On day 14 neural progenitors were dissociated with Accutase to single cells and plated on Laminin coated plates in the maturation media (DMEM/F12/Neurobasal 50%/50%, 1×B27 Supplement, 1× Non-essential amino acids, 1× Glutamax) supplemented with Compound E (0.1 μM, TOCRIS) for final maturation until assay time. For motor neuron differentiation we used our previous published protocol with no further modification (Du, 2015).

Direct Conversion of Adult Human Fibroblasts into iNs: Primary human dermal fibroblasts (WC-04-05-CO-DG, 72 year-old male, WC-60-07-CO-CMN neonatal male, WC-03-06-CO-DG, 62 year-old female, and WC-59-07-CO-CMN, neonatal female, all from WiCell), were cultured in DMEM containing 15% tetracycline-free fetal bovine serum and 0.1% NEAA (Life Technologies), transduced with lentiviral particles for EtO (Ladewig J et al. *Nat Methods.* 9(6):575-8 (2012)) and XTPNgn2: 2A:Ascl1 (N2A), and expanded in the presence of G418 (200 mg/ml; Life Technologies) and puromycin (1 mg/ml; Sigma Aldrich). A previously published protocol (Mertens, 2015) was followed for iN conversion. Neuron conversion (NC) medium based on DMEM: F12/Neurobasal (1:1) was used for incubating these cells for 3 weeks. NC contained the following supplements: N2 supplement, B27 supplement (both 13; GIBCO), doxycycline (2 mg/ml; Sigma Aldrich), Laminin 1 mg/ml; (Life Technologies), dibutyryl cAMP (500 mg/ml; Sigma Aldrich), human recombinant Noggin (150 ng/ml; R&D), LDN-193189 (0.5 mM; Cayman Chemicals) and A83-1 (0.5 mM; Stemgent), CHIR99021 (3 mM; LC Laboratories) and SB-431542 (10 mM; Cayman Chemicals). Medium was changed every third day. For further maturation, iNs were cultured in DMEM:F12/Neurobasal-based neural maturation media (NM) containing N2, B27, GDNF, BDNF (both 20 ng/ml; R&D), dibutyryl cAMP (500 mg/ml; Sigma Aldrich), doxycycline (2 mg/ml; Sigma-Aldrich), and laminin (1 mg/ml; Life Technologies). Converted neurons in 96 well plates were used for immunostaining without further purification.

Immunofluorescent staining and microscopy: Cells were fixed for 20 minutes with 4% paraformaldehyde in PBS at a room temperature. Samples were blocked with 4% donkey serum and 0.2% Tween20 for one hour. Primary antibodies were diluted in 4% donkey serum and 0.1% Tween20 and applied to samples overnight at 4° C. Samples were washed with PBS, incubated with fluorescein-conjugated secondary antibodies for one hour at room temperature, and counterstained with Hoechst for 20 minutes. Samples were imaged on a Nikon Als confocal microscope (Nikon). For measuring neurite length and swelling, images were processed with Fiji software. First, a threshold was set for images to select all cell processes, then neurites were skeletonized and set the parameters to prune cycle method to shortest branch and end points eliminated to prune ends. Then total brunch length was calculated for labeled skeletons (total branch length in pixel/0,000=branch length in cm) and the total number of aggregates were divided by the branch length.

The following primary antibodies were used:

| Antibody | Species | Catalog No. | Company | Dilution |
|---|---|---|---|---|
| TDP43 | Rabbit | 10782-2-AP | Proteintech Group, Inc. | 1/1000 |
| phospho-TDP43 | Rat | MABN14 | MilliporeSigma | 1/500 |
| H3K9Me3 antibody | Rabbit | ab176916 | abcam | 1/5,000 |
| CHAT antibody | Goat | AB144P | Chemicon | |
| HB9 | Mouse | 81.5C10 | DSHB | 1 to 50 |
| TUBB3 | Rabbit | PRB-435P | Covance | 1:10,000 |
| MAP2 | Mouse | M1406 | Sigma | |
| Lamp-2 | Mouse | NBP2-22217 | Novus Biologicals | 250 |
| Lamin B2 antibody | Mouse | ab8983 | abcam | 500 |
| HP1γ antibody | Mouse | MABE656 | Millipore | 500 |
| LAP2β | Mouse | 611000 | BD Biosciences | 1/500 |
| Lamin A + C antibody | Rabbit | ab133256 | abcam | 1/500 |
| H2A.X | Mouse | 05-636 | Upstate (EMD Millipore) | 1/500 |
| Alpha-Internexin | Rabbit | AB40758 | abcam | 1/500 |
| Cleaved Caspase-3 | Rabbit | 9661S | Cell signaling Technologies | |
| PHOSPHODETECT ™ Anti-Neurofilament H | Mouse | NE1022 | Millipore-Sigma | |
| Proteostat | | ENZ-51023 | Enzo | 1000 |
| SOX1 | Goat | AF3369 | R&D systems | |
| OTX2 | Goat | AF1979 | R&D systems | |
| stab2 antibody | Mouse | ab51502 | abcam | |
| Vimentin antibody | Rabbit | bs-0756R | Biossusa | |
| Vimentin antibody | Mouse | AMF-17b | DSHB | |
| Sox9 Antibody | Rabbit | AB5535 | Chemicon | |
| ERp57 | Rabbit | 15967-1-AP | Proteintech Group, Inc. | |
| MBP | Rabbit | AB980 | Millipore | |
| TBR1 | Rabbit | ab31940 | abcam | |

High-content imaging: For measuring cell population, fluorescence intensity, apoptosis, and intensity of H3K9Me3, Lamin B2, Lap2β, and HP1γ, cells were plated in 96-well imaging plates (18000 cells per well, cell carrier) and treated with different molecules (FIG. 11). After staining, images were analyzed using the high-content cellular analysis system Operetta (Perkin Elmer). A set of 60 fields was collected from each well (total of three wells per treatment) using the 40× objective, resulting in over 10,000 cells being scored per well. In this analysis workflow, nuclei based on default protocol B was first identified and the intensity and morphology properties for each nucleus calculated by gating out nuclei with a roundness of below 0.75 and intensities above 1500 for removing extremely bright nuclei (indicative of dead cells). The signal intensity was calculated for each protein in different channels separately. For quantification of H3K9Me3, Lamin B2, Lap2β intensity in directly reprogrammed neurons, cytoplasm was identified based on the 111-tubulin staining surrounding each selected nucleus and quantified the expression of markers in 111-tubulin positive population. All raw data were exported and analyzed with GraphPad Prism (GraphPad Software).

RNA-seq procedure: Cortical neurons differentiated for 7 days and then treated with SLO for 5 days were collected for RNA-seq analysis. Fibroblast cells from aged and young (neonatal) individuals (all at passage 3) treated for 7 consecutive days with SLO were collected for RNA extraction. All experiments were run three times and RNA was extracted from all samples (3 biological replicates and 3 technical replicates) using the RNeasy Plus Mini kit (Qiagen) following manufacturer's instructions. RNA quality was assessed using an Agilent RNA PicoChip with all samples passing QC. Sample libraries were prepared using poly-A selection using an Illumina TruSeq RNAv2 kit following manufacturer's instructions. Prepared libraries were sequenced for 101-bp single-read and performed on an Illumina HiSeq to a read depth of >25 million reads per sample by the DNA Sequencing Facility in the University of Wisconsin-Madison Biotechnology Center. FastQC was performed on all samples with every sample passing all quality control measurements.

RNA-seq analysis: Differentially expressed genes were identified with a glm using the edgeR package (Robinson M D et al. *Bioinformatics*. 26(1):139-40 (2010)). A subset of up to 50 of the most differentially expressed genes with a p-value <0.05 and a log fold-change greater or less than +/−2 were selected (29). Next, both samples and genes were clustered using Euclidean distances. For genes, an additional elbow function was applied to estimate the number of gene clusters present. Calculated relationships are depicted by dendrograms drawn at the top (samples) and to the left (genes) of the heatmap. The gradation of color is determined by a Z-score that is computed and scaled across rows of genes normalized by TMM. The Z-score of a given expression value is the number of standard-deviations away from the mean of all the expression values for that gene.

The empirical Bayes hierarchical modeling approach EBSeq was used to identify differentially expressed genes across 2 or more conditions. Median normalization technique of DESeq (Anders S and Huber W, *Genome Biol.* 11(10):R106 (2010)) was used to account for differences in sequencing depth. EBSeq calculates the posterior probability (PP) of a gene being in each expression pattern. Genes were declared differentially expressed at a false discovery rate controlled at $100*(1-\alpha)$ % if the posterior probability of P1 (EE) is less than $1-\alpha$. Given this list of DE genes, the genes are further classified into each pattern and sorted by PP.

Pathway Analysis: DEGs from each group were analyzed for differentially regulated pathways using ENRICHR (available at enrichr.org on the World Wide Web) which utilizes several pathway databases for general pathway analysis. The KEGG and Wikipathway databases were used for the analyses. DEGs were defined as >100 TPM and >2-fold change over each of the other groups. Pathways that were statistically significant were highlighted as potential differentially regulated. Only pathways that were found significant in more than one of the three analyses were considered for further evaluation.

qRT-PCR: RNA samples were obtained using the RNeasy Plus Mini kit (Qiagen) following manufacturer's instructions. cDNA libraries were constructed using iScript cDNA Synthesis kit (Bio-Rad) using 500ng of purified RNA from each sample as input following manufacturer's instructions. qRT-PCR was performed on a CFX Connect qPCR machine (Bio-Rad) using iTaq SYBR green supermix (Bio-Rad) and equal amounts of cDNA samples. Results were normalized to GAPDH or 18s rRNA levels using the AACt method.

SA-pf Galactosidase assay: Fibroblasts were fixed using 1× fixation buffer provided in reagents and procedure were performed following manufacturer's instructions. Bright-field mages were acquired using a Nikon microscope and positive cell numbers calculated using the Fiji software. Positive cells were grouped based on their appearance after j-Gal staining using histogram function (quantity of staining) to the high and moderate.

Live and Dead cell staining: For cell toxicity assay, cells were plated in 96 well optical plates at a density of 30,000 cells per well and each 3 wells (experimental replicates) treated with different small molecules for 24 hours. Then cells were washed with PBS and incubate with 1 μM EthD-1 and 1 μM calcein AM for 30 minutes at RT and imaged using Operetta (Perkin Elmer) and analyzed with Harmony software.

Single nucleotide polymorphism (SNP) modification in TADBP locus: To perform single nucleotide polymorphism (SNP) modification, a single-strand oligonucleotide (ssODN) method discussed in Yang H et al. *Cell* 154: 1370-79 (2013) was utilized, wherein this approach was modified to fit within CRISPR workflow published in Chen Y, Cao J et al., *Cell Stem Cell* 17(2):233-44 (2015), as follows. Following sgRNA identification for the site of interest using the design tool available at crispr.mit.edu on the World Wide Web, sgRNA sequences were cloned into the pLentiCRISPR-V1 plasmid from the laboratory of Feng Zhang (Addgene V2 version #52961) following the protocol provided with the plasmid (e.g., Shalem O, Sanjana N E et al. *Science.* 343(6166):84-87 (2014); Sanjana N E et al. *Nat Methods* 11(8):783-4 (2014)). Cells were cultured and electroporated as described in Chen Y, Cao J et al., 2015. Single hESCs ($1\times10^7$ cells) were electroporated with appropriate combination of plasmids in 500 microliters of Electroporation Buffer (KCl 5 mM, $MgCl_2$ 5 mM, HEPES 15 mM, $Na_2HPO_4$ 102.94 mM, $NaH_2PO_4$ 47.06 mM, PH=7.2) using the Gene Pulser Xcell System (Bio-Rad) at 250 V, 500 μF in a 0.4 cm cuvettes (Phenix Research Products). Cells were electroporated in a cocktail of 15 micrograms of the pLentiCRISPRVl-TDP43 sg14 plasmid and 100 microliters of a 10 micromolar ssODN targeting the TDP43 G298S mutant genetic site. This ssODN was non-complementary to the sgRNA sequence and comprised 141 nucleotides, including 70 nucleotides upstream and 70 nucleotides downstream of the targeted indel generation site (Yang et al., 2013). Following electroporation, cells were plated on MEF feeders in 1.0 μM ROCK inhibitor. At 24 and 72 hours post-electroporation, cells were treated with puromycin (0.5 g/ml, Invivogen, ant-pr-1) to select for cells containing the pLentiCRISPRVl-TDP43 sg14 plasmid. After removal of the puromycin at 96 hours, cells were cultured in MEF-conditioned hPSC media until colonies were visible.

For genotyping single-cell generated colonies were manually selected and mechanically disaggregated. Genomic DNA was amplified using Q5 polymerase-based PCR (NEB) and proper codons determined using sanger sequencing. To identify non-specific genome editing, we analyzed suspected off-target sites for genome modification, using the 5 highest-likelihood off target sites predicted by the crispr.mit.edu algorithms.

Electrophysiology: The cultured astrocytes were continuously perfused with artificial cerebrospinal fluid (ACSF) saturated with 95% $O_2$/5% $CO_2$. The composition of ACSF was (in mM) 124 NaCl, 3.5 KCl, 1.5 $CaCl_2$, 1.3 $MgSO_4$, 1.24 $KH_2PO_4$, 18 $NaHCO_3$, 20 glucose, PH 7.4. The electrodes were filled with a solution consisted of (in mM) 140 K-gluconate, 0.1 $CaCl_2$, 2 $MgCl_2$, 1 EGTA, 2 ATP K2, 0.1 GTP Na3, and 10 HEPES, PH 7.25 (290 mOsm) and had a resistance of 4-6 MΩ. Astrocytes were visualized using an Olympus Optical (Tokyo, Japan) BX51WI microscope with differential interference contrast optics at 40×. Voltage and current clamp recordings were obtained at 30° C. using a MultiClamp 700B amplifier (Axon instruments). Signals were filtered at 4 kHz using a Digidata 1322A analog-to-digital converter (Axon instruments). Access resistance was monitored prior to and following recordings and cells with resistances >25 μMΩ at either point were discarded from analyses.

The invention has been described in connection with what are presently considered to be the most practical and preferred embodiments. However, this invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

TABLE 1

Small Molecules and Response in Fibroblasts and Cortical Neurons

| | | Dunnett's multiple comparisons test | Fibroblast cells H3K9Me3 Mean Diff. | H3K9Me3 Summary | H3K9Me3 Adjusted P Value | HP1γ Mean Diff. | HP1γ Summary | HP1γ Adjusted P Value | LAP2β Mean Diff. | LAP2β Summary | LAP2β Adjusted P Value |
|---|---|---|---|---|---|---|---|---|---|---|---|
| 5-AZA-20-DEOXYCYTIDINE | DNA methyltransferase inhibitor | Ctrl vs. Aza | −74.9 | **** | <0.0001 | −3.191 | * | 0.0374 | 0.5946 | ns | 0.9996 |
| Actinomycin D | inhibiting DNA-primed RNA synthesis | Ctrl vs. Act | −43.6 | **** | <0.0001 | 14.37 | **** | 0.0001 | 72.97 | **** | <0.0001 |
| Cisplatin | Topo I, II inhibitor | Ctrl vs. Cis | 69.38 | **** | <0.0001 | 26.48 | **** | 0.0001 | 49.37 | **** | <0.0001 |
| SCR-7 | Ligase V inhibitor | Ctrl vs. Src | 15.34 | * | 0.0148 | 7.523 | **** | 0.0001 | 15.39 | **** | <0.0001 |
| Phosphoramidon disodium salt | metalloendpeptidase inhibitor | Ctrl vs. Phos | 15.65 | ** | 0.01 | −5.096 | **** | 0.0001 | −0.123 | ns | >0.9999 |
| Lopinavir | HIV protease inhibitor | Ctrl vs. Lopi | −204.3 | **** | <0.0001 | −40.53 | **** | 0.0001 | −4.12 | ns | 0.0599 |
| GGTI298 | geranylgeranyltransferase I (GGTase I) inhibitor. | Ctrl vs. GGt | 54.63 | **** | <0.0001 | 9.125 | **** | 0.0001 | −4.369 | * | 0.0424 |
| Sodium Butyrate | histone deacetylase inhibitor I, II | Ctrl vs. Sbu | 174.2 | **** | <0.0001 | 44.47 | **** | 0.0001 | 84.59 | **** | <0.0001 |
| KU-60019 | ATM inhibitor | Ctrl vs. KU | −11.87 | ns | 0.171 | 3.831 | * | 0.0106 | 0.0548 | ns | >0.9999 |
| Lactacystin | irreversible proteasome | Ctrl vs. Lac | −37.32 | **** | <0.0001 | −51.17 | **** | 0.0001 | 113 | **** | <0.0001 |
| Temozolomide | DNA alkylation | Ctrl vs. Temo | 126.2 | **** | <0.0001 | 33.31 | **** | 0.0001 | 34.27 | **** | <0.0001 |
| Rucaparib | PARP1 inhibitor | Ctrl vs. Ruc | 178 | **** | <0.0001 | 56.75 | **** | 0.0001 | 27.12 | **** | <0.0001 |
| SirReal2 | Sirt2 inhibitor | Ctrl vs. Sreal | −55.6 | **** | <0.0001 | 7.083 | **** | 0.0001 | −3.167 | ns | 0.4768 |
| EX-527 | Sirt1 inhibitor | Ctrl vs. Ex | 5.361 | ns | 0.9934 | 11.05 | **** | 0.0001 | 45.33 | **** | <0.0001 |
| Hydroxyurea | DNA synthesis stress inducer | Ctrl vs. Hu | 139.2 | **** | <0.0001 | 55.88 | **** | 0.0001 | 77.56 | **** | <0.0001 |
| Apo866 | NAD biosynthesis inhibitor | Ctrl vs. Apo | 70.37 | **** | <0.0001 | 26.82 | **** | 0.0001 | 44.74 | **** | <0.0001 |
| Palbociclib | CDK4/6 inhibitor | Ctrl vs. Palbo | 176.8 | **** | <0.0001 | 50.32 | **** | 0.0001 | 67.37 | **** | <0.0001 |
| O151 | DNA Glycosylase-1 (OGG1) | Ctrl vs. O151 | −10.03 | ns | 0.4309 | 7.458 | **** | 0.0001 | 0.5596 | ns | 0.9996 |
| Lomeguatrib-O6BTG | MGMT inhibitor | Ctrl vs. O6B | −42.41 | **** | <0.0001 | 23.08 | **** | 0.0001 | −2.701 | ns | 0.7402 |
| Etoposid | Topo II inhibitor | Ctrl vs. Etp | 111.1 | **** | <0.0001 | 48 | **** | 0.0001 | 83.18 | **** | <0.0001 |
| Romidepsin | HDAC1,2 inhibitor | Ctrl vs. Romi | 8.77 | ns | 0.5947 | 10.68 | **** | 0.0001 | 16.03 | **** | <0.0001 |
| SBI-0206965 | Autophagy inhibitor | Ctrl vs. SBI | 102.2 | **** | <0.0001 | 57.81 | **** | 0.0001 | 34.76 | **** | <0.0001 |
| Sirtinol | Sirtuin inhibitors | Ctrl vs. Sir | 25.91 | **** | <0.0001 | 11.05 | **** | 0.0001 | 19.02 | **** | <0.0001 |
| MHY1485 | mTOR activator | Ctrl vs. MHY | 78.56 | **** | <0.0001 | 27.68 | **** | 0.0001 | 6.893 | **** | <0.0001 |
| WZ4003 | AMPK inhibitor | Ctrl vs. WZ | 9.026 | ns | 0.5845 | 16.89 | **** | 0.0001 | 3.661 | ns | 0.2437 |

| | | Dunnett's multiple comparisons test | Cortical Neurons H3K9Me3 Mean Diff. | H3K9Me3 Summary | H3K9Me3 Adjusted P Value | HP1γ Mean Diff. | HP1γ Summary | HP1γ Adjusted P Value | LAP2β Mean Diff. | LAP2β Summary | LAP2β Adjusted P Value | multiple comparisons test |
|---|---|---|---|---|---|---|---|---|---|---|---|---|
| 5-AZA-20-DEOXYCYTIDINE | DNA methyltransferase inhibitor | Ctrl vs. Aza | −66.5 | ns | 0.2666 | 6.29 | * | 0.0329 | −25 | ns | 0.0753 | Ctrl vs. Aza |

TABLE 1-continued

| Small Molecules and Response in Fibroblasts and Cortical Neurons | | | | | | | | | | | | |
|---|---|---|---|---|---|---|---|---|---|---|---|---|
| Actinomycin D | inhibiting DNA-primed RNA synthesis | Ctrl vs. Act | −1078 | **** | <0.0001 | 7.06 | ns | 0.282 | 96 | **** | 0.0001 | Ctrl vs. Act |
| Cisplatin | Topo I, II inhibitor | Ctrl vs. Cis | 41.6 | ns | 0.8073 | −2.84 | ns | 0.705 | 45.3 | **** | 0.0001 | Ctrl vs. Cis |
| SCR-7 | Ligase V inhibitor | Ctrl vs. Src | 275 | **** | <0.0001 | 8.95 | *** | 0.0004 | 95.8 | **** | 0.0001 | Ctrl vs. Src |
| Phosphoramidon disodium salt | metalloendpeptidase inhibitor | Ctrl vs. Phos | 146 | **** | <0.0001 | 12.5 | **** | 0.0001 | −66.1 | **** | 0.0001 | Ctrl vs. Phos |
| Lopinavir | HIV protease inhibitor | Ctrl vs. Lopi | 377 | **** | <0.0001 | 11.3 | **** | 0.0001 | 80.1 | **** | 0.0001 | Ctrl vs. Lopi |
| GGTI298 | geranylgeranyltransferase I (GGTase I) inhibitor. | Ctrl vs. GGt | 117 | ** | 0.0011 | 12.6 | **** | 0.0001 | 9.17 | ns | 0.9931 | Ctrl vs. GGt |
| Sodium Butyrate | histone deacetylase inhibitor I, II | Ctrl vs. Sbu | 194 | **** | <0.0001 | 9.76 | **** | 0.0001 | 54.5 | **** | 0.0001 | Ctrl vs. Sbu |
| KU-60019 | ATM inhibitor | Ctrl vs. KU | 43.8 | ns | 0.9063 | 6.3 | * | 0.0429 | 44.2 | **** | 0.0001 | Ctrl vs. KU |
| Lactacystin | irreversible proteasome | Ctrl vs. Lac | −194 | **** | <0.0001 | −4.64 | ns | 0.1037 | 55.4 | **** | 0.0001 | Ctrl vs. Lac |
| Temozolomide | DNA alkylation | Ctrl vs. Temo | −83.3 | ** | 0.003 | 2.05 | ns | 0.9324 | −62.8 | **** | 0.0001 | Ctrl vs. Temo |
| Rucaparib | PARP1 inhibitor | Ctrl vs. Ruc | 22.2 | ns | 0.9954 | 2.53 | ns | 0.7753 | −28.8 | *** | 0.0003 | Ctrl vs. Ruc |
| SirReal2 | Sirt2 inhibitor | Ctrl vs. Sreal | 135 | **** | <0.0001 | 4.09 | ns | 0.4607 | −1.84 | ns | 0.9997 | Ctrl vs. Sreal |
| EX-527 | Sirt1 inhibitor | Ctrl vs. Ex | 288 | **** | <0.0001 | 6.05 | * | 0.0432 | 47.9 | **** | 0.0001 | Ctrl vs. Ex |
| Hydroxyurea | DNA synthesis stress inducer | Ctrl vs. Hu | 44.4 | ns | 0.5835 | −5.6 | * | 0.0181 | 21.6 | * | 0.0277 | Ctrl vs. Hu |
| Apo866 | NAD biosynthesis inhibitor | Ctrl vs. Apo | −235 | * | 0.0258 | 6.91 | ns | 0.9555 | 435 | **** | 0.0001 | Ctrl vs. Apo |
| Palbociclib | CDK4/6 inhibitor | Ctrl vs. Palbo | 285 | **** | <0.0001 | −3 | ns | 0.467 | 16.7 | ns | 0.1302 | Ctrl vs. Palbo |
| O151 | DNA Glycosylase-1 (OGG1) | Ctrl vs. O151 | 226 | **** | <0.0001 | 9.44 | **** | 0.0001 | 101 | **** | 0.0001 | Ctrl vs. O151 |
| Lomeguatrib-O6BTG | MGMT inhibitor | Ctrl vs. O6B | 131 | **** | <0.0001 | 3.16 | ns | 0.736 | −1.54 | ns | 0.9997 | Ctrl vs. O6B |
| Etoposid | Topo II inhibitor | Ctrl vs. Etp | 300 | **** | <0.0001 | −3 | ns | 0.5298 | 8.57 | ns | 0.9524 | Ctrl vs. Etp |
| Romidepsin | HDAC1,2 inhibitor | Ctrl vs. Romi | 204 | **** | <0.0001 | −14.2 | **** | 0.0001 | 46.6 | **** | 0.0001 | Ctrl vs. Romi |
| SBI-0206965 | Autophagy inhibitor | Ctrl vs. SBI | 551 | **** | <0.0001 | 15.5 | **** | 0.0001 | 62.5 | **** | 0.0001 | Ctrl vs. SBI |
| Sirtinol | Sirtuin inhibitors | Ctrl vs. Sir | 241 | **** | <0.0001 | 3.12 | ns | 0.7233 | 32.4 | *** | 0.0008 | Ctrl vs. Sir |
| MHY1485 | mTOR activator | Ctrl vs. MHY | 90.3 | * | 0.0125 | −5.21 | ns | 0.117 | −17.4 | ns | 0.3601 | Ctrl vs. MHY |
| WZ4003 | AMPK inhibitor | Ctrl vs. WZ | 229 | **** | <0.0001 | −10.3 | **** | 0.0001 | 19.2 | ns | 0.2525 | Ctrl vs. WZ |

TABLE 1-continued

Small Molecules and Response in Fibroblasts and Cortical Neurons

| comparisons test | H3K9Me3 Mean Diff. | H3K9Me3 Summary | H3K9Me3 Adjusted P Value | HP1γ | LAP2β Mean Diff. | LAP2β Summary | LAP2β P Value | multiple |
|---|---|---|---|---|---|---|---|---|
| SBI vs. Ctrl | −458.4 | **** | <0.0001 | | −232.9 | **** | <0.0001 | SBI vs. Ctrl |
| SBI vs. SBI, SCR | 373.7 | **** | <0.0001 | | 173.4 | **** | <0.0001 | SBI vs. SBI, SCR |
| SBI vs. SBI, O151 | 65.25 | ns | 0.9762 | | 148.1 | **** | <0.0001 | SBI vs. SBI, O151 |
| SBI vs. SBI, SBU | 48.59 | ns | 0.9872 | | 153.7 | **** | <0.0001 | SBI vs. SBI, SBU |
| SBI vs. SBI, LOPI | 186.1 | **** | <0.0001 | | 293.7 | **** | <0.0001 | SBI vs. SBI, LOPI |
| SBI vs. LOPI, SCR | 299.4 | **** | <0.0001 | | 192.4 | **** | <0.0001 | SBI vs. LOPI, SCR |
| SBI vs. LOPI, O151 | 338.7 | **** | <0.0001 | | 173.4 | **** | <0.0001 | SBI vs. LOPI, O151 |
| SBI vs. LOPI, SBU | 174.9 | * | 0.0302 | | 152.7 | **** | <0.0001 | SBI vs. LOPI, SBU |
| SBI vs. O151, SCR | 60.03 | ns | 0.8451 | | 110.5 | **** | <0.0001 | SBI vs. O151, SCR |
| SBI vs. SCR, SBU | 274.3 | **** | <0.0001 | | 258.1 | **** | <0.0001 | SBI vs. SCR, SBU |
| SBI vs. O151, SBU | −252.7 | **** | <0.0001 | | 99.18 | **** | <0.0001 | SBI vs. O151, SBU |
| SBI vs. SBI, LOPI, SCR | −113.6 | ns | 0.366 | | 132.8 | **** | <0.0001 | SBI vs. SBI, LOPI, SCR |
| SBI vs. SBI, LOPI, O151 | 1235 | **** | <0.0001 | | 231.2 | **** | <0.0001 | SBI vs. SBI, LOPI, O151 |
| SBI vs. SBI, LOPI, SBU | 154.6 | ns | 0.355 | | 152.7 | **** | <0.0001 | SBI vs. SBI, LOPI, SBU |

TABLE 1-continued

| Small Molecules and Response in Fibroblasts and Cortical Neurons | | | | | | | | | | |
|---|---|---|---|---|---|---|---|---|---|---|
| | SBI vs. LOPI, O151, SCR | 96.19 | ns | 0.737 | | 111.5 | **** | <0.0001 | SBI vs. LOPI, O151, SCR |
| | SBI vs. LOPI, SCR, SBU | 341.6 | **** | <0.0001 | | 103.3 | **** | <0.0001 | SBI vs. SCR, LOPI, SBU |
| | | Fibroblast cells | | | | | | | |
| | | H3K9Me3 | | | HP1γ | LAP2β | | | |
| | SBI vs. O151, SCR, SBU SBI vs. SBI, O151, SCR SBI vs. SBI, O151, SBU SBI vs. SBI, SCR, SBU | | | | | | | | |
| | | Cortical Neurons | | | | | | | |
| | | H3K9Me3 | | | HP1γ | LAP2β | | | |
| | SBI vs. O151, SCR, SBU | −1237 | **** | <0.0001 | | 74.31 | **** | <0.0001 | SBI vs. O151, SCR, SBU |
| | SBI vs. SBI, O151, SCR | 199.8 | **** | <0.0001 | | 157 | **** | <0.0001 | SBI vs. SBI, O151, SCR |
| | SBI vs. SBI, O151, SBU | 1608 | **** | <0.0001 | | 319.3 | **** | <0.0001 | SBI vs. SBI, O151, SBU |
| | SBI vs. SBI, SCR, SBU | −743.8 | **** | <0.0001 | | 75.74 | **** | <0.0001 | SBI vs. SBI, SCR, SBU |

TABLE 2

Common Genes

| Category | Term | Count | % | PValue | Genes | List Total | Pop Hits | Pop Total | Fold Enric | Bonferroni | Benjamini | FDR |
|---|---|---|---|---|---|---|---|---|---|---|---|---|
| KEGG_PATHWAY | hsa04723:Retrograde endocannabinoid signaling | 11 | 0.018083 | 8.81E−05 | SLC32A1, ADCY2, GABRB3, GABRA4, CNR1, GABRA5, GNB4, GRIA4, GNG4, PLCB1, PRKCB | 157 | 101 | 6879 | 4.771962 | 0.017211 | 0.017211 | 0.110125 |
| KEGG_PATHWAY | hsa04727:GABAergic synapse | 10 | 0.016439 | 1.19E−04 | SLC32A1, ADCY2, SLC6A1, GABRB3, GABRA4, GABRA5, GNB4, GNG4, GAD1, PRKCB | 157 | 85 | 6879 | 5.15474 | 0.023165 | 0.01165 | 0.148639 |
| KEGG_PATHWAY | hsa05032:Morphine addiction | 9 | 0.014795 | 0.001009 | SLC32A1, PDE7B, ADCY2, GABRB3, GABRA4, GABRA5, GNB4, GNG4, PRKCB | 157 | 91 | 6879 | 4.33338 | 0.180334 | 0.064137 | 1.254156 |
| KEGG_PATHWAY | hsa05033:Nicotine addiction | 6 | 0.009863 | 0.00195 | SLC32A1, GRIN2B, GABRB3, GABRA4, GABRA5, GRIA4 | 157 | 40 | 6879 | 6.572293 | 0.319212 | 0.091651 | 2.410788 |
| KEGG_PATHWAY | hsa04713:Circadian entrainment | 8 | 0.013151 | 0.005617 | ADCY2, GRIN2B, GNB4, GRIA4, GNG4, PLCB1, RASD1, PRKCB | 157 | 95 | 6879 | 3.689708 | 0.670317 | 0.199025 | 6.800166 |
| KEGG_PATHWAY | hsa04360:Axon guidance | 9 | 0.014795 | 0.008027 | SEMA5A, EPHA5, SEMA6B, ROBO1, PLXNB1, PLXNB2, SEMA4B, ROBO2, EPHA3 | 157 | 127 | 6879 | 3.10502 | 0.795595 | 0.232494 | 9.58528 |
| KEGG_PATHWAY | hsa04728:Dopaminergic synapse | 9 | 0.014795 | 0.008401 | GNAL, GRIN2B, PPP1R1B, GNB4, GRIA4, GNG4, PLCB1, PPP2R2C, PRKCB | 157 | 128 | 6879 | 3.080762 | 0.810253 | 0.211354 | 10.01126 |
| KEGG_PATHWAY | hsa04725:Cholinergic synapse | 8 | 0.013151 | 0.012798 | ADCY2, CAMK4, CHRM2, BCL2, GNB4, GNG4, PLCB1, PRKCB | 157 | 111 | 6879 | 3.157858 | 0.920938 | 0.271808 | 14.87493 |
| KEGG_PATHWAY | hsa04724:Glutamatergic synapse | 8 | 0.013151 | 0.014661 | GRM3, ADCY2, GRIN2B, GNB4, GRIA4, GNG4, PLCB1, PRKCB | 157 | 114 | 6879 | 3.074757 | 0.945508 | 0.276243 | 16.86203 |

TABLE 2-continued

| Common Genes | | | | | | | | | | | | |
|---|---|---|---|---|---|---|---|---|---|---|---|---|
| Category | Term | Count | % | PValue | Genes | List Total | Pop Hits | Pop Total | Fold Enric | Bonferroni | Benjamini | FDR |
| KEGG_PATHWAY | hsa04020:Calcium signaling pathway | 10 | 0.016439 | 0.020221 | ORAI2, GNAL, ATP2B2, ADCY2, CAMK4, ERBB4, CHRM2, PLCB1, PRKCB, HTR2A | 157 | 179 | 6879 | 2.447781 | 0.982125 | 0.331311 | 22.54035 |
| KEGG_PATHWAY | hsa04080:Neuroactive ligand-receptor interaction | 13 | 0.021371 | 0.023132 | PARD3, GABRA4, GABRB3, GLRA3, GABRA5, GLRA2, GRIA4, NPY1R, GRM3, GRNI2B, CHRM2 ,CNR1, HTR2A | 157 | 277 | 6879 | 2.056313 | 0.880053 | 0.342382 | 25.36864 |
| KEGG_PATHWAY | hsa04010:MAPK signaling pathway | 12 | 0.019727 | 0.028423 | MEF2C, DUSP3, RASGRF1, RASGRP1, GNA12, PTPRR, CACNG4, ELK1, FGF13, MAPK8IP1, FGF12, PRKCB | 157 | 253 | 6879 | 2.078195 | 0.996588 | 0.377106 | 30.269 |
| KEGG_PATHWAY | hsa04014:Ras signaling pathway | 11 | 0.018083 | 0.032347 | GRIN2B, RASGRF1, RASGRP1, ELK1, FGF13, GNB4, FGF12, BAD, GNG4, RALGDS, PRKCB | 157 | 226 | 6879 | 2.132602 | 0.998463 | 0.392423 | 33.70872 |
| KEGG_PATHWAY | hsa04921:Oxytocin signaling pathway | 8 | 0.013151 | 0.053815 | MEF2C, ADCY2, CAMK4, CACNG4, ELK1, PRKAA2, PLCB1, PRKCB | 157 | 150 | 6879 | 2.336815 | 0.999981 | 0.540853 | 49.92368 |
| KEGG_PATHWAY | hsa05031:Amphetamine addiction | 5 | 0.008219 | 0.062162 | GRIN2B, CAMK4, PPP1R1B, GRIA4, PRKCB | 157 | 66 | 6879 | 3.31934 | 0.999997 | 0.569528 | 55.17553 |
| KEGG_PATHWAY | hsa00564:Glycerophospholipid metabolism | 6 | 0.009863 | 0.064117 | PLD3, CDIPT, LPCAT1, DGKG, LYPLA1, ETNK2 | 157 | 95 | 6879 | 2.767281 | 0.999998 | 0.55775 | 56.32956 |
| KEGG_PATHWAY | hsa04024:cAMP signaling pathway | 9 | 0.014795 | 0.080423 | ATP2B2, ADCY2, GRIN2B, CAMK4, CHRM2, PPP1R1B, GRIA4, BAD, NPY1R | 157 | 198 | 6879 | 1.991604 | 1 | 0.621515 | 64.94559 |

TABLE 2-continued

| Common Genes | | | | | | | | | | | | |
|---|---|---|---|---|---|---|---|---|---|---|---|---|
| Category | Term | Count | % | PValue | Genes | List Total | Pop Hits | Pop Total | Fold Enric | Bonferroni | Benjamini | FDR |
| KEGG_PATHWAY | hsa04151:PI3K-Akt signaling pathway | 13 | 0.021371 | 0.091667 | SGK1, CHRM2, BCL2, COL6A1, RELN, FGF13, GNB4, BAD, FGF12, PRKAA2, GNG4, PPP2R2C, SPP1 | 157 | 345 | 6879 | 1.651011 | 1 | 0.650846 | 69.94324 |
| KEGG_PATHWAY | hsa04510:Focal adhesion | 9 | 0.014795 | 0.095773 | RASGRF1, BCL2, COL6A1, ELK1, RELN, BAD, ZYX, SPP1, PRKCB | 157 | 206 | 6879 | 1.91426 | 1 | 0.647899 | 71.59852 |
| KEGG_PATHWAY | hsa00510:N-Glycan biosynthesis | | 0.006576 | 0.099097 | MGAT4B, ST6GAL2, MGAT4C, MANIA1 | 157 | 49 | 6879 | 3.576758 | 1 | 0.642251 | 72.8767 |

We claim:

1. An in vitro method for inducing cellular senescence in human neurons, the method comprising (a) contacting the human neurons in vitro with a composition comprising one or more of SBI-0206965, Lopinavir, O151, sodium butyrate, or SCR-7; and (b) culturing the contacted neurons in the presence of the culture medium of (a) for about two to about four days to generate a population of chemically induced senescent (CIS) neurons.

2. The method of claim 1, where the CIS neurons express senescence associated biomarker β-galactosidase and exhibit decreased expression of one or more of Histone 3 lysine 9 trimethylation (H3k9Me3), Lamina-associated polypeptide 2β (Lap2β), and Heterochromatin protein 1γ (HP1γ) relative to control neurons.

3. The method of claim 1, wherein the neurons are human pluripotent stem cell (hPSC)-derived neurons, primary neurons, or induced neurons (iNs).

4. The method of claim 3, wherein the hPSC-derived neurons derived from human embryonic stem cells (ESCs) or human induced pluripotent stem cells (iPSCs).

5. The method of claim 4, wherein the human iPSCs are obtained by reprogramming a somatic cell of an individual having a neurodegenerative disease, whereby the CIS neurons exhibit one or more morphological features characteristic of the neurodegenerative disease.

6. The method of claim 5, wherein the neurodegenerative disease is Amyotrophic lateral sclerosis (ALS), Alzheimer's disease (AD), Parkinson's disease (PD), or age-related macular degeneration.

7. The method of claim 5, wherein the neurodegenerative disease is Amyotrophic lateral sclerosis (ALS) and the morphological features include axonal swelling, axonal degeneration, reduced expression of Histone 3 lysine 9 trimethylation (H3K9Me9) and Lamina-associated polypeptide 2β (Lap2β), increased expression of phosphorylated neurofilament, and increased protein aggregation relative to control neurons.

8. The method of claim 1, wherein the composition is a neuron maturation medium comprising N2, B27, GDNF, BDNF, dibutyryl cAMP, doxycycline, and laminin.

* * * * *

SEQUENCE LISTING

```
<160> NUMBER OF SEQ ID NOS: 2

<210> SEQ ID NO 1
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 1

gggtggattt ggtaatagca gagggggtgg agctggtttg ggaaacaatc aaggt          55


<210> SEQ ID NO 2
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 2

gggtggattt ggtaatagca gagggggtgg agctggtttg ggaaacaatc aaggt          55
```